United States Patent [19]
Kilgannon et al.

[11] Patent Number: 5,773,293
[45] Date of Patent: Jun. 30, 1998

[54] ANTI-ICAM-4 ANTIBODIES AND HYBRIDOMAS

[75] Inventors: Patrick D. Kilgannon, Bothell; W. Michael Gallatin, Mercer Island, both of Wash.

[73] Assignee: ICOS Corporation, Bothell, Wash.

[21] Appl. No.: 485,604

[22] Filed: Jun. 7, 1995

Related U.S. Application Data

[63] Continuation-in-part of Ser. No. 245,295, May 18, 1994, Pat. No. 5,700,658, which is a continuation-in-part of Ser. No. 102,852, Aug. 5, 1993, abandoned, which is a continuation-in-part of Ser. No. 9,266, Jan. 22, 1993, abandoned, which is a continuation-in-part of Ser. No. 894,061, Jun. 5, 1992, abandoned, which is a continuation-in-part of Ser. No. 889,724, May 26, 1992, abandoned, which is a continuation-in-part of Ser. No. 827,689, Jan. 27, 1992, abandoned.

[51] Int. Cl.$^6$ .............................. C12N 5/12; C07K 16/00; C12P 21/08
[52] U.S. Cl. ................... 435/334; 435/70.21; 530/388.1; 530/388.22
[58] Field of Search ............................ 530/387.1, 387.9, 530/388.1, 388.15, 389.1, 388.22; 435/70.1, 70.2, 70.21, 240.26, 240.27, 334

[56] References Cited

FOREIGN PATENT DOCUMENTS

| 468257 A | 1/1992 | European Pat. Off. . |
|---|---|---|
| WO 89/02922 | 4/1989 | WIPO . |
| WO 90/13300 | 11/1990 | WIPO . |
| WO 91/10683 | 7/1991 | WIPO . |
| WO 91/16928 | 11/1991 | WIPO . |
| WO 92/04034 | 3/1992 | WIPO . |
| WO 92/06199 | 4/1992 | WIPO . |
| WO 93/14776 | 8/1993 | WIPO . |

OTHER PUBLICATIONS

Bailly et al, Proc. Natl. Acad. Sci. 91:5306–5310, Jun. 1994.
Bailly et al., Eur. J. Immunol, 25:3316–3320, 1995.
Goding, "The Production of Monoclonal Antibodies" In Monoclonal Antibodies, 1983 by Academic Press Inc. pp. 56–97.
Ashkenazi, et al., *Proc.Natl.Acad.Sci.* (*USA*) 88:10535–10539 (1991) Protection against endotoxic shock by tumor necrosis factor receptor immunoadhesin.
Capecchi, *Science* 244:1288–1292 (1989) "Altering the genome by the homologous recombination".
Capon, et al., *Nature* 337:525–531 (1989) "Designing CD4 immunoadhesins for AIDS therapy".
de Fourgerolles, et al., *J.Exp.Med.* 175:185–190 (1992) "Intercellular adhesion molecule 3, a third adhesion counter–receptor for lymphocyte function associated molecule 1 on resting lymphocytes".
Dustin, et al., *J.Immunol.* 137:245–254 (1986) "Induction by IL–1 and interferon–γ: tissue distribution, biochemistry, and function of a natural adherence molecule (ICAM–1)".
Edwards, *Curr.Opin.Ther.Pat.* 1: 1627–1630 (1991) "Cell adhesion molecules as a target for therapy".
Frohman, *PCR Protocols*, Innis (ed), pp. 28–38 (1990) "RACE: rapid amplification of cDNA ends".
Imamura, et al., *Neurosci.Letts.* 119:118–121 (1990) "Variations by layers and developmental changes in expression of telencephalin".
Kita, et al., *Biochem.Biophys.Acta* 1131:108–110 (1992) "Sequence and expressino of rt ICAM–1".
Mori, et al., *Proc.Natl.Acad.Sci.* (*USA*) 84:3921–3925 (1987) "Telencephalon–specific antigen identified by monoclonal antibody".
Newmann, et al., *Science* 247:1219–1222 (1990) "PECAM–1 (CD31) cloning and relation to adhesion molecules of the immunoglobulin gene superfamily".
Oka, et al., *Neuroscience* 35:93–103 (1990) "Mammalian telencephalic neurons express a segment–specific membrane glycoprotein, telencephalin".
Sonderegger et al., *J.Cell.Biol.* 119:1387–1394 (1992) "Regulation of axonal growth in the vertebrate nervous system by interactions between glycoproteins belonging to two subgroups of the immunoglobulin superfamily".
Springer, *Nature* 346:425–434 (1990) "Adhesion receptors of the immune system".
Staunton, et al., *Nature* 339:61–64 (1989) "Functional cloning of ICAM–2, a cell adhesion ligand for LFA–1 homologous to ICAM–1".
Vonderheide, et al., *J.Cell.Biol* 125:215–222 (1994) "Residues within a conserved amino acid motif of domains 1 and 4 of VCAM–1 ar required for binding to VLA–4".
Xu, et al., *J.Immunol.* 149:2560–2565 (1992) "Isolation, characterization, and expression of mouse ICAM–2 complementary and genomic DNA".
Yoshihara, et al., *Neurosci.Res.* 10:83–105 (1991) "Immunoglobulin superfamily molecules in the nervous system".
Yoshihiro, et al., *Neuron* 12:543–553 (1994) An ICAM–related neuronal glycoprotein, telencephalin, with brain segment–specific expression.
Yoshihiro, et al., *Neuroscience* Supp. 18, p. S83 (1994) "Primary structure of telencephalon–specific neuronal adhesion molecule telencephalin".
Yoshihiro, et al., *Soc.Neurosci.Abstr.* 19 (1–3) p. 646 (1993) "Telencephanlin, a brian segment–specific dendritic glycoprotein, is a novel member of immunoglobulin superfamily".

*Primary Examiner*—Paula K. Hutzell
*Assistant Examiner*—Patricia A. Duffy
*Attorney, Agent, or Firm*—Marshall, O'Toole, Gerstein, Murray & Borun

[57] ABSTRACT

DNA sequences encoding a novel intercellular adhesion molecule polypeptide (designated "ICAM-4") and variants thereof are disclosed along with methods and materials for production of the same by recombinant procedures. Antibody molecules that bind to ICAM-4, and uses thereof, are also disclosed.

6 Claims, No Drawings

5,773,293

SEQUENCE LISTING ( 1 ) GENERAL INFORMATION:

( i i i ) NUMBER OF SEQUENCES: 32

( 2 ) INFORMATION FOR SEQ ID NO:1:

( i ) SEQUENCE CHARACTERISTICS:
( A ) LENGTH: 2988 base pairs
( B ) TYPE: nucleic acid
( C ) STRANDEDNESS: single ( D ) TOPOLOGY: linear ( i i ) MOLECULE TYPE: cDNA ( i x ) FEATURE:
    ( A ) NAME/KEY: CDS
    ( B ) LOCATION: 61..2814

( x i ) SEQUENCE DESCRIPTION: SEQ ID NO:1:

```
AATTCGATCA CTCGCGCTCC CCTCGCCTTC TGCGCTCTCC CCTCCCTGGC AGCGGCGGCA        60

ATG CCG GGG CCT TCA CCA GGG CTG CGC CGA ACG CTC CTC GGC CTC TGG        108
Met Pro Gly Pro Ser Pro Gly Leu Arg Arg Thr Leu Leu Gly Leu Trp
 1               5                   10                  15

GCT GCC CTG GGC CTG GGG ATC CTA GGC ATC TCA GCG GTC GCG CTA GAA        156
Ala Ala Leu Gly Leu Gly Ile Leu Gly Ile Ser Ala Val Ala Leu Glu
            20                  25                  30

CCT TTC TGG GCG GAC CTT CAG CCC CGC GTG GCG CTC GTG GAG CGC GGG        204
Pro Phe Trp Ala Asp Leu Gln Pro Arg Val Ala Leu Val Glu Arg Gly
        35                  40                  45

GGC TCG CTG TGG CTC AAC TGC AGC ACT AAC TGT CCG AGG CCG GAG CGC        252
Gly Ser Leu Trp Leu Asn Cys Ser Thr Asn Cys Pro Arg Pro Glu Arg
    50                  55                  60

GGT GGC CTG GAG ACC TCG CTA CGC CGA AAC GGG ACC CAG AGG GGT CTG        300
Gly Gly Leu Glu Thr Ser Leu Arg Arg Asn Gly Thr Gln Arg Gly Leu
65                  70                  75                  80

CGC TGG CTG GCT CGA CAG CTG GTG GAC ATC CGA GAG CCT GAA ACC CAG        348
Arg Trp Leu Ala Arg Gln Leu Val Asp Ile Arg Glu Pro Glu Thr Gln
                85                  90                  95

CCG GTC TGC TTC TTC CGC TGC GCG CGC CGC ACA CTC CAA GCG CGT GGG        396
Pro Val Cys Phe Phe Arg Cys Ala Arg Arg Thr Leu Gln Ala Arg Gly
            100                 105                 110

CTC ATC CGA ACT TTC CAG CGA CCG GAT CGG GTA GAG CTA GTG CCT CTG        444
Leu Ile Arg Thr Phe Gln Arg Pro Asp Arg Val Glu Leu Val Pro Leu
        115                 120                 125

CCT CCT TGG CAG CCT GTA GGT GAG AAC TTC ACC TTG AGC TGC AGG GTC        492
Pro Pro Trp Gln Pro Val Gly Glu Asn Phe Thr Leu Ser Cys Arg Val
    130                 135                 140

CCG GGG GCA GGA CCC CGA GCG AGC CTC ACA TTG ACC TTG CTG CGA GGC        540
Pro Gly Ala Gly Pro Arg Ala Ser Leu Thr Leu Thr Leu Leu Arg Gly
145                 150                 155                 160

GGC CAG GAG CTG ATT CGC CGA AGT TTC GTA GGC GAG CCA CCC CGA GCT        588
Gly Gln Glu Leu Ile Arg Arg Ser Phe Val Gly Glu Pro Pro Arg Ala
                165                 170                 175

CGG GGT GCG ATG CTC ACC GCC ACG GTC CTG GCG CGC AGA GAG GAT CAC        636
Arg Gly Ala Met Leu Thr Ala Thr Val Leu Ala Arg Arg Glu Asp His
            180                 185                 190

AGG GCC AAT TTC TCA TGC CTC GCG GAG CTT GAC CTG CGG CCA CAC GGC        684
Arg Ala Asn Phe Ser Cys Leu Ala Glu Leu Asp Leu Arg Pro His Gly
        195                 200                 205

TTG GGA CTG TTT GCA AAC AGC TCA GCC CCC AGA CAG CTC CGC ACG TTT        732
Leu Gly Leu Phe Ala Asn Ser Ser Ala Pro Arg Gln Leu Arg Thr Phe
    210                 215                 220

GCC ATG CCT CCA CTT TCC CCG AGC CTT ATT GCC CCA CGA TTC TTA GAA        780
Ala Met Pro Pro Leu Ser Pro Ser Leu Ile Ala Pro Arg Phe Leu Glu
225                 230                 235                 240

GTG GGC TCA GAA AGG CCG GTG ACT TGC ACT TTG GAT GGA CTG TTT CCT        828
Val Gly Ser Glu Arg Pro Val Thr Cys Thr Leu Asp Gly Leu Phe Pro
                245                 250                 255

GCC CCA GAA GCC GGG GTT TAC CTC TCT CTG GGA GAT CAG AGG CTT CAT        876
Ala Pro Glu Ala Gly Val Tyr Leu Ser Leu Gly Asp Gln Arg Leu His
            260                 265                 270
```

| | | | | | | | | | | | | | | | | |
|---|---|---|---|---|---|---|---|---|---|---|---|---|---|---|---|---|
| CCT | AAT | GTG | ACC | CTC | GAC | GGG | GAG | AGC | CTT | GTG | GCC | ACT | GCC | ACA | GCT | 924 |
| Pro | Asn | Val | Thr | Leu | Asp | Gly | Glu | Ser | Leu | Val | Ala | Thr | Ala | Thr | Ala | |
| | | 275 | | | | 280 | | | | | 285 | | | | | |
| ACA | GCA | AGT | GAA | GAA | CAG | GAA | GGC | ACC | AAA | CAG | CTG | ATG | TGC | ATC | GTG | 972 |
| Thr | Ala | Ser | Glu | Glu | Gln | Glu | Gly | Thr | Lys | Gln | Leu | Met | Cys | Ile | Val | |
| | 290 | | | | | 295 | | | | | 300 | | | | | |
| ACC | CTC | GGG | GGC | GAA | AGC | AGG | GAG | ACC | CAG | GAA | AAC | CTG | ACT | GTC | TAC | 1020 |
| Thr | Leu | Gly | Gly | Glu | Ser | Arg | Glu | Thr | Gln | Glu | Asn | Leu | Thr | Val | Tyr | |
| 305 | | | | | 310 | | | | | 315 | | | | | 320 | |
| AGC | TTC | CCG | GCT | CCT | CTT | CTG | ACT | TTA | AGT | GAG | CCA | GAA | GCC | CCC | GAG | 1068 |
| Ser | Phe | Pro | Ala | Pro | Leu | Leu | Thr | Leu | Ser | Glu | Pro | Glu | Ala | Pro | Glu | |
| | | | | 325 | | | | | 330 | | | | | 335 | | |
| GGA | AAG | ATG | GTG | ACC | GTA | AGC | TGC | TGG | GCA | GGG | GCC | CGA | GCC | CTT | GTC | 1116 |
| Gly | Lys | Met | Val | Thr | Val | Ser | Cys | Trp | Ala | Gly | Ala | Arg | Ala | Leu | Val | |
| | | | 340 | | | | 345 | | | | | 350 | | | | |
| ACC | TTG | GAG | GGA | ATT | CCA | GCT | GCG | GTC | CCT | GGG | CAG | CCC | GCT | GAG | CTC | 1164 |
| Thr | Leu | Glu | Gly | Ile | Pro | Ala | Ala | Val | Pro | Gly | Gln | Pro | Ala | Glu | Leu | |
| | | 355 | | | | 360 | | | | | 365 | | | | | |
| CAG | TTA | AAT | GTC | ACA | AAG | AAT | GAC | GAC | AAG | CGG | GGC | TTC | TTC | TGC | GAC | 1212 |
| Gln | Leu | Asn | Val | Thr | Lys | Asn | Asp | Asp | Lys | Arg | Gly | Phe | Phe | Cys | Asp | |
| | 370 | | | | | 375 | | | | | 380 | | | | | |
| GCT | GCC | CTC | GAT | GTG | GAC | GGG | GAA | ACT | CTG | AGA | AAG | AAC | CAG | AGC | TCT | 1260 |
| Ala | Ala | Leu | Asp | Val | Asp | Gly | Glu | Thr | Leu | Arg | Lys | Asn | Gln | Ser | Ser | |
| 385 | | | | | 390 | | | | | 395 | | | | | 400 | |
| GAG | CTT | CGT | GTT | CTG | TAC | GCA | CCT | CGG | CTG | GAT | GAC | TTG | GAC | TGT | CCC | 1308 |
| Glu | Leu | Arg | Val | Leu | Tyr | Ala | Pro | Arg | Leu | Asp | Asp | Leu | Asp | Cys | Pro | |
| | | | | 405 | | | | | 410 | | | | | 415 | | |
| AGG | AGC | TGG | ACG | TGG | CCA | GAG | GGT | CCA | GAG | CAG | ACC | CTC | CAC | TGC | GAG | 1356 |
| Arg | Ser | Trp | Thr | Trp | Pro | Glu | Gly | Pro | Glu | Gln | Thr | Leu | His | Cys | Glu | |
| | | | 420 | | | | 425 | | | | | 430 | | | | |
| GCC | CGT | GGA | AAC | CCT | GAG | CCC | TCC | GTG | CAC | TGT | GCA | AGG | CCT | GAC | GGT | 1404 |
| Ala | Arg | Gly | Asn | Pro | Glu | Pro | Ser | Val | His | Cys | Ala | Arg | Pro | Asp | Gly | |
| | | 435 | | | | 440 | | | | | 445 | | | | | |
| GGG | GCG | GTG | CTA | GCG | CTG | GGC | CTG | TTG | GGT | CCA | GTG | ACC | CGT | GCC | CTC | 1452 |
| Gly | Ala | Val | Leu | Ala | Leu | Gly | Leu | Leu | Gly | Pro | Val | Thr | Arg | Ala | Leu | |
| | 450 | | | | | 455 | | | | | 460 | | | | | |
| GCG | GGC | ACT | TAC | CGA | TGT | ACA | GCA | ATC | AAT | GGG | CAA | GGC | CAG | GCG | GTC | 1500 |
| Ala | Gly | Thr | Tyr | Arg | Cys | Thr | Ala | Ile | Asn | Gly | Gln | Gly | Gln | Ala | Val | |
| 465 | | | | | 470 | | | | | 475 | | | | | 480 | |
| AAG | GAT | GTG | ACC | CTG | ACT | GTG | GAA | TAT | GCC | CCA | GCG | CTG | GAC | AGT | GTA | 1548 |
| Lys | Asp | Val | Thr | Leu | Thr | Val | Glu | Tyr | Ala | Pro | Ala | Leu | Asp | Ser | Val | |
| | | | | 485 | | | | | 490 | | | | | 495 | | |
| GGC | TGC | CCA | GAA | CGT | ATT | ACT | TGG | CTG | GAG | GGG | ACA | GAG | GCA | TCG | CTT | 1596 |
| Gly | Cys | Pro | Glu | Arg | Ile | Thr | Trp | Leu | Glu | Gly | Thr | Glu | Ala | Ser | Leu | |
| | | | 500 | | | | 505 | | | | | 510 | | | | |
| AGC | TGT | GTG | GCA | CAC | GGG | GTC | CCA | CCA | CCT | AGC | GTG | AGC | TGT | GTG | CGC | 1644 |
| Ser | Cys | Val | Ala | His | Gly | Val | Pro | Pro | Pro | Ser | Val | Ser | Cys | Val | Arg | |
| | | 515 | | | | 520 | | | | | 525 | | | | | |
| TCT | GGA | AAG | GAG | GAA | GTC | ATG | GAA | GGG | CCC | CTG | CGT | GTG | GCC | CGG | GAG | 1692 |
| Ser | Gly | Lys | Glu | Glu | Val | Met | Glu | Gly | Pro | Leu | Arg | Val | Ala | Arg | Glu | |
| | 530 | | | | | 535 | | | | | 540 | | | | | |
| CAC | GCT | GGC | ACT | TAC | CGA | TGC | GAA | GCC | ATC | AAC | GCC | AGG | GGA | TCA | GCG | 1740 |
| His | Ala | Gly | Thr | Tyr | Arg | Cys | Glu | Ala | Ile | Asn | Ala | Arg | Gly | Ser | Ala | |
| 545 | | | | | 550 | | | | | 555 | | | | | 560 | |
| GCC | AAA | AAT | GTG | GCT | GTC | ACG | GTG | GAA | TAT | GGT | CCC | AGT | TTT | GAG | GAG | 1788 |
| Ala | Lys | Asn | Val | Ala | Val | Thr | Val | Glu | Tyr | Gly | Pro | Ser | Phe | Glu | Glu | |
| | | | | 565 | | | | | 570 | | | | | 575 | | |
| TTG | GGC | TGC | CCC | AGC | AAC | TGG | ACT | TGG | GTA | GAA | GGA | TCT | GGA | AAA | CTG | 1836 |
| Leu | Gly | Cys | Pro | Ser | Asn | Trp | Thr | Trp | Val | Glu | Gly | Ser | Gly | Lys | Leu | |
| | | | 580 | | | | 585 | | | | | 590 | | | | |

| | | | | | | | | | | | | | | | | |
|---|---|---|---|---|---|---|---|---|---|---|---|---|---|---|---|---|
| TTT | TCC | TGT | GAA | GTT | GAT | GGG | AAG | CCG | GAA | CCA | CGC | GTG | GAG | TGC | GTG | 1884 |
| Phe | Ser | Cys | Glu | Val | Asp | Gly | Lys | Pro | Glu | Pro | Arg | Val | Glu | Cys | Val | |
| | | 595 | | | | | 600 | | | | | 605 | | | | |
| GGC | TCG | GAG | GGT | GCA | AGC | GAA | GGG | GTA | GTG | TTG | CCC | CTG | GTG | TCC | TCG | 1932 |
| Gly | Ser | Glu | Gly | Ala | Ser | Glu | Gly | Val | Val | Leu | Pro | Leu | Val | Ser | Ser | |
| | | 610 | | | | | 615 | | | | | 620 | | | | |
| AAC | TCT | GGT | TCC | AGA | AAC | TCT | ATG | ACT | CCT | GGT | AAC | CTG | TCA | CCG | GGT | 1980 |
| Asn | Ser | Gly | Ser | Arg | Asn | Ser | Met | Thr | Pro | Gly | Asn | Leu | Ser | Pro | Gly | |
| 625 | | | | | 630 | | | | | 635 | | | | | 640 | |
| ATT | TAC | CTC | TGC | AAC | GCC | ACC | AAC | CGG | CAT | GGC | TCC | ACA | GTC | AAA | ACA | 2028 |
| Ile | Tyr | Leu | Cys | Asn | Ala | Thr | Asn | Arg | His | Gly | Ser | Thr | Val | Lys | Thr | |
| | | | | 645 | | | | | 650 | | | | | 655 | | |
| GTC | GTC | GTG | AGC | GCG | GAA | TCA | CCG | CCA | CAG | ATG | GAT | GAA | TCC | AGT | TGC | 2076 |
| Val | Val | Val | Ser | Ala | Glu | Ser | Pro | Pro | Gln | Met | Asp | Glu | Ser | Ser | Cys | |
| | | | 660 | | | | | 665 | | | | | 670 | | | |
| CCG | AGT | CAC | CAG | ACA | TGG | CTG | GAA | GGA | GCC | GAG | GCT | ACT | GCG | CTG | GCC | 2124 |
| Pro | Ser | His | Gln | Thr | Trp | Leu | Glu | Gly | Ala | Glu | Ala | Thr | Ala | Leu | Ala | |
| | | 675 | | | | | 680 | | | | | 685 | | | | |
| TGC | AGT | GCC | AGA | GGC | CGC | CCC | TCT | CCA | CGC | GTG | CGC | TGT | TCC | AGG | GAA | 2172 |
| Cys | Ser | Ala | Arg | Gly | Arg | Pro | Ser | Pro | Arg | Val | Arg | Cys | Ser | Arg | Glu | |
| | | 690 | | | | | 695 | | | | | 700 | | | | |
| GGT | GCA | GCC | AGG | CTG | GAG | AGG | CTA | CAG | GTG | TCC | CGA | GAG | GAT | GCG | GGG | 2220 |
| Gly | Ala | Ala | Arg | Leu | Glu | Arg | Leu | Gln | Val | Ser | Arg | Glu | Asp | Ala | Gly | |
| 705 | | | | | 710 | | | | | 715 | | | | | 720 | |
| ACC | TAC | CTG | TGT | GTG | GCT | ACC | AAC | GCG | CAT | GGC | ACG | GAT | TCA | CGG | ACC | 2268 |
| Thr | Tyr | Leu | Cys | Val | Ala | Thr | Asn | Ala | His | Gly | Thr | Asp | Ser | Arg | Thr | |
| | | | | 725 | | | | | 730 | | | | | 735 | | |
| GTC | ACT | GTG | GGT | GTG | GAA | TAC | CGG | CCT | GTG | GTG | GCT | GAG | CTG | GCA | GCC | 2316 |
| Val | Thr | Val | Gly | Val | Glu | Tyr | Arg | Pro | Val | Val | Ala | Glu | Leu | Ala | Ala | |
| | | | 740 | | | | | 745 | | | | | 750 | | | |
| TCG | CCC | CCA | AGC | GTG | CGG | CCT | GGC | GGA | AAC | TTC | ACT | CTG | ACC | TGC | CGT | 2364 |
| Ser | Pro | Pro | Ser | Val | Arg | Pro | Gly | Gly | Asn | Phe | Thr | Leu | Thr | Cys | Arg | |
| | | 755 | | | | | 760 | | | | | 765 | | | | |
| GCA | GAG | GCC | TGG | CCT | CCA | GCC | CAG | ATC | AGC | TGG | CGC | GCG | CCC | CCG | GGA | 2412 |
| Ala | Glu | Ala | Trp | Pro | Pro | Ala | Gln | Ile | Ser | Trp | Arg | Ala | Pro | Pro | Gly | |
| | 770 | | | | | 775 | | | | | 780 | | | | | |
| GCT | CTC | AAC | CTC | GGT | CTC | TCC | AGC | AAC | AAC | AGC | ACG | CTG | AGC | GTG | GCG | 2460 |
| Ala | Leu | Asn | Leu | Gly | Leu | Ser | Ser | Asn | Asn | Ser | Thr | Leu | Ser | Val | Ala | |
| 785 | | | | | 790 | | | | | 795 | | | | | 800 | |
| GGT | GCC | ATG | GGC | AGC | CAT | GGT | GGC | GAG | TAT | GAG | TGC | GCA | GCC | ACC | AAT | 2508 |
| Gly | Ala | Met | Gly | Ser | His | Gly | Gly | Glu | Tyr | Glu | Cys | Ala | Ala | Thr | Asn | |
| | | | | 805 | | | | | 810 | | | | | 815 | | |
| GCG | CAT | GGG | CGC | CAC | GCA | CGG | CGC | ATC | ACG | GTG | CGC | GTG | GCC | GGT | CCA | 2556 |
| Ala | His | Gly | Arg | His | Ala | Arg | Arg | Ile | Thr | Val | Arg | Val | Ala | Gly | Pro | |
| | | | 820 | | | | | 825 | | | | | 830 | | | |
| TGG | CTG | TGG | GTC | GCT | GTG | GGC | GGT | GCG | GCA | GGG | GCG | GCG | CTG | CTG | | 2604 |
| Trp | Leu | Trp | Val | Ala | Val | Gly | Gly | Ala | Ala | Gly | Gly | Ala | Ala | Leu | Leu | |
| | | 835 | | | | | 840 | | | | | 845 | | | | |
| GCC | GCA | GGG | GCC | GGC | CTG | GCC | TTC | TAC | GTG | CAG | TCC | ACC | GCT | TGC | AAG | 2652 |
| Ala | Ala | Gly | Ala | Gly | Leu | Ala | Phe | Tyr | Val | Gln | Ser | Thr | Ala | Cys | Lys | |
| | 850 | | | | | 855 | | | | | 860 | | | | | |
| AAG | GGA | GAG | TAC | AAC | GTC | CAG | GAG | GCT | GAG | AGC | TCA | GGC | GAG | GCG | GTG | 2700 |
| Lys | Gly | Glu | Tyr | Asn | Val | Gln | Glu | Ala | Glu | Ser | Ser | Gly | Glu | Ala | Val | |
| 865 | | | | | 870 | | | | | 875 | | | | | 880 | |
| TGT | CTC | AAT | GGC | GCG | GGC | GGG | ACA | CCG | GGT | GCA | GAA | GGC | GGA | GCA | GAG | 2748 |
| Cys | Leu | Asn | Gly | Ala | Gly | Gly | Thr | Pro | Gly | Ala | Glu | Gly | Gly | Ala | Glu | |
| | | | | 885 | | | | | 890 | | | | | 895 | | |
| ACC | CCC | GGC | ACT | GCC | GAG | TCA | CCT | GCA | GAT | GGC | GAG | GTT | TTC | GCC | ATC | 2796 |
| Thr | Pro | Gly | Thr | Ala | Glu | Ser | Pro | Ala | Asp | Gly | Glu | Val | Phe | Ala | Ile | |
| | | | 900 | | | | | 905 | | | | | 910 | | | |

```
CAG CTG ACA TCT TCC TGAGCCTGTA TCCAGCTCCC CCAGGGGCCT CGAAAGCACA         2851
Gln Leu Thr Ser Ser
        915

GGGGTGGACG TATGTATTGT TCACTCTCTA TTTATTCAAC TCCAGGGGCG TCGTCCCCGT       2911

TTTCTACCCA TTCCCTTAAT AAAGTTTTTA TAGGAGAAAA AAAAAAAAA AAAAAAAAA         2971

AAAAAAAAAA AAAAAA                                                       2988
```

(2) INFORMATION FOR SEQ ID NO:2:

(i) SEQUENCE CHARACTERISTICS:
        (A) LENGTH: 917 amino acids
        (B) TYPE: amino acid
        (D) TOPOLOGY: linear (ii) MOLECULE TYPE: protein (xi) SEQUENCE DESCRIPTION: SEQ ID NO:2:

```
Met Pro Gly Pro Ser Pro Gly Leu Arg Arg Thr Leu Leu Gly Leu Trp
  1               5                  10                  15

Ala Ala Leu Gly Leu Gly Ile Leu Gly Ile Ser Ala Val Ala Leu Glu
             20                  25                  30

Pro Phe Trp Ala Asp Leu Gln Pro Arg Val Ala Leu Val Glu Arg Gly
         35                  40                  45

Gly Ser Leu Trp Leu Asn Cys Ser Thr Asn Cys Pro Arg Pro Glu Arg
     50                  55                  60

Gly Gly Leu Glu Thr Ser Leu Arg Arg Asn Gly Thr Gln Arg Gly Leu
 65                  70                  75                  80

Arg Trp Leu Ala Arg Gln Leu Val Asp Ile Arg Glu Pro Glu Thr Gln
                 85                  90                  95

Pro Val Cys Phe Phe Arg Cys Ala Arg Arg Thr Leu Gln Ala Arg Gly
                100                 105                 110

Leu Ile Arg Thr Phe Gln Arg Pro Asp Arg Val Glu Leu Val Pro Leu
            115                 120                 125

Pro Pro Trp Gln Pro Val Gly Glu Asn Phe Thr Leu Ser Cys Arg Val
        130                 135                 140

Pro Gly Ala Gly Pro Arg Ala Ser Leu Thr Leu Thr Leu Leu Arg Gly
145                 150                 155                 160

Gly Gln Glu Leu Ile Arg Arg Ser Phe Val Gly Glu Pro Pro Arg Ala
                165                 170                 175

Arg Gly Ala Met Leu Thr Ala Thr Val Leu Ala Arg Arg Glu Asp His
                180                 185                 190

Arg Ala Asn Phe Ser Cys Leu Ala Glu Leu Asp Leu Arg Pro His Gly
            195                 200                 205

Leu Gly Leu Phe Ala Asn Ser Ser Ala Pro Arg Gln Leu Arg Thr Phe
        210                 215                 220

Ala Met Pro Pro Leu Ser Pro Ser Leu Ile Ala Pro Arg Phe Leu Glu
225                 230                 235                 240

Val Gly Ser Glu Arg Pro Val Thr Cys Thr Leu Asp Gly Leu Phe Pro
                245                 250                 255

Ala Pro Glu Ala Gly Val Tyr Leu Ser Leu Gly Asp Gln Arg Leu His
            260                 265                 270

Pro Asn Val Thr Leu Asp Gly Glu Ser Leu Val Ala Thr Ala Thr Ala
            275                 280                 285

Thr Ala Ser Glu Glu Gln Glu Gly Thr Lys Gln Leu Met Cys Ile Val
            290                 295                 300

Thr Leu Gly Gly Glu Ser Arg Glu Thr Gln Glu Asn Leu Thr Val Tyr
```

-continued

```
              305                     310                     315                     320
Ser   Phe   Pro   Ala   Pro   Leu   Leu   Thr   Leu   Ser   Glu   Pro   Glu   Ala   Pro   Glu
                        325                     330                     335
Gly   Lys   Met   Val   Thr   Val   Ser   Cys   Trp   Ala   Gly   Ala   Arg   Ala   Leu   Val
                        340                     345                     350
Thr   Leu   Glu   Gly   Ile   Pro   Ala   Ala   Val   Pro   Gly   Gln   Pro   Ala   Glu   Leu
            355                     360                     365
Gln   Leu   Asn   Val   Thr   Lys   Asn   Asp   Asp   Lys   Arg   Gly   Phe   Phe   Cys   Asp
            370                     375                     380
Ala   Ala   Leu   Asp   Val   Asp   Gly   Glu   Thr   Leu   Arg   Lys   Asn   Gln   Ser   Ser
385                     390                     395                     400
Glu   Leu   Arg   Val   Leu   Tyr   Ala   Pro   Arg   Leu   Asp   Asp   Leu   Asp   Cys   Pro
                        405                     410                     415
Arg   Ser   Trp   Thr   Trp   Pro   Glu   Gly   Pro   Glu   Gln   Thr   Leu   His   Cys   Glu
                  420                     425                     430
Ala   Arg   Gly   Asn   Pro   Glu   Pro   Ser   Val   His   Cys   Ala   Arg   Pro   Asp   Gly
                  435                     440                     445
Gly   Ala   Val   Leu   Ala   Leu   Gly   Leu   Leu   Gly   Pro   Val   Thr   Arg   Ala   Leu
            450                     455                     460
Ala   Gly   Thr   Tyr   Arg   Cys   Thr   Ala   Ile   Asn   Gly   Gln   Gly   Gln   Ala   Val
465                     470                     475                     480
Lys   Asp   Val   Thr   Leu   Thr   Val   Glu   Tyr   Ala   Pro   Ala   Leu   Asp   Ser   Val
                        485                     490                     495
Gly   Cys   Pro   Glu   Arg   Ile   Thr   Trp   Leu   Glu   Gly   Thr   Glu   Ala   Ser   Leu
                  500                     505                     510
Ser   Cys   Val   Ala   His   Gly   Val   Pro   Pro   Ser   Val   Ser   Cys   Val   Arg
                  515                     520                     525
Ser   Gly   Lys   Glu   Glu   Val   Met   Glu   Gly   Pro   Leu   Arg   Val   Ala   Arg   Glu
            530                     535                     540
His   Ala   Gly   Thr   Tyr   Arg   Cys   Glu   Ala   Ile   Asn   Ala   Arg   Gly   Ser   Ala
545                     550                     555                     560
Ala   Lys   Asn   Val   Ala   Val   Thr   Val   Glu   Tyr   Gly   Pro   Ser   Phe   Glu   Glu
                        565                     570                     575
Leu   Gly   Cys   Pro   Ser   Asn   Trp   Thr   Trp   Val   Glu   Gly   Ser   Gly   Lys   Leu
                  580                     585                     590
Phe   Ser   Cys   Glu   Val   Asp   Gly   Lys   Pro   Glu   Pro   Arg   Val   Glu   Cys   Val
                  595                     600                     605
Gly   Ser   Glu   Gly   Ala   Ser   Glu   Gly   Val   Val   Leu   Pro   Leu   Val   Ser   Ser
      610                     615                     620
Asn   Ser   Gly   Ser   Arg   Asn   Ser   Met   Thr   Pro   Gly   Asn   Leu   Ser   Pro   Gly
625                     630                     635                     640
Ile   Tyr   Leu   Cys   Asn   Ala   Thr   Asn   Arg   His   Gly   Ser   Thr   Val   Lys   Thr
                  645                     650                     655
Val   Val   Val   Ser   Ala   Glu   Ser   Pro   Pro   Gln   Met   Asp   Glu   Ser   Ser   Cys
                  660                     665                     670
Pro   Ser   His   Gln   Thr   Trp   Leu   Glu   Gly   Ala   Glu   Ala   Thr   Ala   Leu   Ala
                  675                     680                     685
Cys   Ser   Ala   Arg   Gly   Arg   Pro   Ser   Pro   Arg   Val   Arg   Cys   Ser   Arg   Glu
            690                     695                     700
Gly   Ala   Ala   Arg   Leu   Glu   Arg   Leu   Gln   Val   Ser   Arg   Glu   Asp   Ala   Gly
705                     710                     715                     720
Thr   Tyr   Leu   Cys   Val   Ala   Thr   Asn   Ala   His   Gly   Thr   Asp   Ser   Arg   Thr
                        725                     730                     735
```

```
Val  Thr  Val  Gly  Val  Glu  Tyr  Arg  Pro  Val  Val  Ala  Glu  Leu  Ala  Ala
               740                     745                    750

Ser  Pro  Pro  Ser  Val  Arg  Pro  Gly  Asn  Phe  Thr  Leu  Thr  Cys  Arg
          755                     760                    765

Ala  Glu  Ala  Trp  Pro  Pro  Ala  Gln  Ile  Ser  Trp  Arg  Ala  Pro  Pro  Gly
     770                     775                    780

Ala  Leu  Asn  Leu  Gly  Leu  Ser  Ser  Asn  Asn  Ser  Thr  Leu  Ser  Val  Ala
785                 790                     795                         800

Gly  Ala  Met  Gly  Ser  His  Gly  Gly  Glu  Tyr  Glu  Cys  Ala  Ala  Thr  Asn
                805                     810                         815

Ala  His  Gly  Arg  His  Ala  Arg  Arg  Ile  Thr  Val  Arg  Val  Ala  Gly  Pro
               820                     825                    830

Trp  Leu  Trp  Val  Ala  Val  Gly  Gly  Ala  Ala  Gly  Gly  Ala  Ala  Leu  Leu
          835                     840                    845

Ala  Ala  Gly  Ala  Gly  Leu  Ala  Phe  Tyr  Val  Gln  Ser  Thr  Ala  Cys  Lys
          850                     855                    860

Lys  Gly  Glu  Tyr  Asn  Val  Gln  Glu  Ala  Glu  Ser  Ser  Gly  Glu  Ala  Val
865                      870                     875                         880

Cys  Leu  Asn  Gly  Ala  Gly  Gly  Thr  Pro  Gly  Ala  Glu  Gly  Gly  Ala  Glu
                    885                     890                         895

Thr  Pro  Gly  Thr  Ala  Glu  Ser  Pro  Ala  Asp  Gly  Glu  Val  Phe  Ala  Ile
               900                     905                    910

Gln  Leu  Thr  Ser  Ser
               915
```

( 2 ) INFORMATION FOR SEQ ID NO:3:

( i ) SEQUENCE CHARACTERISTICS:
        ( A ) LENGTH: 315 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..315

( x i ) SEQUENCE DESCRIPTION: SEQ ID NO:3:

```
CCG  GAT  CGG  GTA  GAG  CTA  GTG  CCT  CTG  CCT  CCT  TGG  CAG  CCT  GTA  GGT      48
Pro  Asp  Arg  Val  Glu  Leu  Val  Pro  Leu  Pro  Pro  Trp  Gln  Pro  Val  Gly
  1                 5                    10                    15

GAG  AAC  TTC  ACC  TTG  AGC  TGC  AGG  GTC  CCG  GGG  GCA  GGA  CCC  CGA  GCG      96
Glu  Asn  Phe  Thr  Leu  Ser  Cys  Arg  Val  Pro  Gly  Ala  Gly  Pro  Arg  Ala
               20                    25                    30

AGC  CTC  ACA  TTG  ACC  TTG  CTG  CGA  GGC  GGA  CAG  GAG  CTG  ATT  CGC  CGA     144
Ser  Leu  Thr  Leu  Thr  Leu  Leu  Arg  Gly  Gly  Gln  Glu  Leu  Ile  Arg  Arg
          35                    40                    45

AGT  TTC  GTA  GGC  GAG  CCA  CCC  CGA  GCT  CGG  TGT  GCG  ATG  CTC  ACC  GCC     192
Ser  Phe  Val  Gly  Glu  Pro  Pro  Arg  Ala  Arg  Cys  Ala  Met  Leu  Thr  Ala
     50                    55                    60

ACG  GTC  CTG  GCG  CGC  AGA  GAG  GAT  CAC  AGG  GAC  AAT  TTC  TCA  TGC  CTC     240
Thr  Val  Leu  Ala  Arg  Arg  Glu  Asp  His  Arg  Asp  Asn  Phe  Ser  Cys  Leu
65                    70                    75                         80

GCG  GAG  CTT  GAC  CTG  CGG  ACA  CAC  GGC  TTG  GGA  CTG  TTT  GCA  AAC  AGC     288
Ala  Glu  Leu  Asp  Leu  Arg  Thr  His  Gly  Leu  Gly  Leu  Phe  Ala  Asn  Ser
                    85                    90                         95

TCA  GCC  CCC  AGA  CAG  CTC  CGC  ACG  TTT                                         315
Ser  Ala  Pro  Arg  Gln  Leu  Arg  Thr  Phe
               100                    105
```

( 2 ) INFORMATION FOR SEQ ID NO:4:

( i ) SEQUENCE CHARACTERISTICS:
        ( A ) LENGTH: 1781 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 16..1659

( x i ) SEQUENCE DESCRIPTION: SEQ ID NO:4:

```
CAGCTCTCTG TCAGA ATG GCC ACC ATG GTA CCA TCC GTG TTG TGG CCC AGG            51
               Met Ala Thr Met Val Pro Ser Val Leu Trp Pro Arg
                 1               5                      10

GCC TGC TGG ACT CTG CTG GTC TGC TGT CTG CTG ACC CCA GGT GTC CAG             99
Ala Cys Trp Thr Leu Leu Val Cys Cys Leu Leu Thr Pro Gly Val Gln
            15                  20                  25

GGG CAG GAG TTC CTT TTG CGG GTG GAG CCC CAG AAC CCT GTG CTC TCT            147
Gly Gln Glu Phe Leu Leu Arg Val Glu Pro Gln Asn Pro Val Leu Ser
        30                  35                  40

GCT GGA GGG TCC CTG TTT GTG AAC TGC AGT ACT GAT TGT CCC AGC TCT            195
Ala Gly Gly Ser Leu Phe Val Asn Cys Ser Thr Asp Cys Pro Ser Ser
45                  50                  55                  60

GAG AAA ATC GCC TTG GAG ACG TCC CTA TCA AAG GAG CTG GTG GCC AGT            243
Glu Lys Ile Ala Leu Glu Thr Ser Leu Ser Lys Glu Leu Val Ala Ser
                65                  70                  75

GGC ATG GGC TGG GCA GCC TTC AAT CTC AGC AAC GTG ACT GGC AAC AGT            291
Gly Met Gly Trp Ala Ala Phe Asn Leu Ser Asn Val Thr Gly Asn Ser
            80                  85                  90

CGG ATC CTC TGC TCA GTG TAC TGC AAT GGC TCC CAG ATA ACA GGC TCC            339
Arg Ile Leu Cys Ser Val Tyr Cys Asn Gly Ser Gln Ile Thr Gly Ser
        95                  100                 105

TCT AAC ATC ACC GTG TAC GGG CTC CCG GAG CGT GTG GAG CTG GCA CCC            387
Ser Asn Ile Thr Val Tyr Gly Leu Pro Glu Arg Val Glu Leu Ala Pro
    110                 115                 120

CTG CCT CCT TGG CAG CCG GTG GGC CAG AAC TTC ACC CTG CGC TGC CAA            435
Leu Pro Pro Trp Gln Pro Val Gly Gln Asn Phe Thr Leu Arg Cys Gln
125                 130                 135                 140

GTG GAG GGT GGG TCG CCC CGG ACC AGC CTC ACG GTG GTG CTG CTT CGC            483
Val Glu Gly Gly Ser Pro Arg Thr Ser Leu Thr Val Val Leu Leu Arg
                145                 150                 155

TGG GAG GAG GAG CTG AGC CGG CAG CCC GCA GTG GAG GAG CCA GCG GAG            531
Trp Glu Glu Glu Leu Ser Arg Gln Pro Ala Val Glu Glu Pro Ala Glu
            160                 165                 170

GTC ACT GCC ACT GTG CTG GCC AGC AGA GAC GAC CAC GGA GCC CCT TTC            579
Val Thr Ala Thr Val Leu Ala Ser Arg Asp Asp His Gly Ala Pro Phe
        175                 180                 185

TCA TGC CGC ACA GAA CTG GAC ATG CAG CCC CAG GGG CTG GGA CTG TTC            627
Ser Cys Arg Thr Glu Leu Asp Met Gln Pro Gln Gly Leu Gly Leu Phe
    190                 195                 200

GTG AAC ACC TCA GCC CCC CGC CAG CTC CGA ACC TTT GTC CTG CCC GTG            675
Val Asn Thr Ser Ala Pro Arg Gln Leu Arg Thr Phe Val Leu Pro Val
205                 210                 215                 220

ACC CCC CCG CGC CTC GTG GCC CCC CGG TTC TTG GAG GTG GAA ACG TCG            723
Thr Pro Pro Arg Leu Val Ala Pro Arg Phe Leu Glu Val Glu Thr Ser
                225                 230                 235

TGG CCG GTG GAC TGC ACC CTA GAC GGG CTT TTT CCA GCC TCA GAG GCC            771
Trp Pro Val Asp Cys Thr Leu Asp Gly Leu Phe Pro Ala Ser Glu Ala
```

```
                      240                        245                        250
CAG  GTC  TAC  CTG  GCG  CTG  GGG  GAC  CAG  ATG  CTG  AAT  GCG  ACA  GTC  ATG      819
Gln  Val  Tyr  Leu  Ala  Leu  Gly  Asp  Gln  Met  Leu  Asn  Ala  Thr  Val  Met
          255                       260                       265

AAC  CAC  GGG  GAC  ACG  CTA  ACG  GCC  ACA  GCC  ACA  GCC  ACG  GCG  CGC  GCG      867
Asn  His  Gly  Asp  Thr  Leu  Thr  Ala  Thr  Ala  Thr  Ala  Thr  Ala  Arg  Ala
     270                       275                                 280

GAT  CAG  GAG  GGT  GCC  CGG  GAG  ATC  GTC  TGC  AAC  GTG  ACC  CTA  GGG  GGC      915
Asp  Gln  Glu  Gly  Ala  Arg  Glu  Ile  Val  Cys  Asn  Val  Thr  Leu  Gly  Gly
285                           290                       295                       300

GAG  AGA  CGG  GAG  GCC  CGG  GAG  AAC  TTG  ACG  GTC  TTT  AGC  TTC  CTA  GGA      963
Glu  Arg  Arg  Glu  Ala  Arg  Glu  Asn  Leu  Thr  Val  Phe  Ser  Phe  Leu  Gly
                              305                       310                       315

CCC  ATT  GTG  AAC  CTC  AGC  GAG  CCC  ACC  GCC  CAT  GAG  GGG  TCC  ACA  GTG     1011
Pro  Ile  Val  Asn  Leu  Ser  Glu  Pro  Thr  Ala  His  Glu  Gly  Ser  Thr  Val
               320                       325                       330

ACC  GTG  AGT  TGC  ATG  GCT  GGG  GCT  CGA  GTC  CAG  GTC  ACG  CTG  GAC  GGA     1059
Thr  Val  Ser  Cys  Met  Ala  Gly  Ala  Arg  Val  Gln  Val  Thr  Leu  Asp  Gly
               335                       340                       345

GTT  CCG  GCC  GCG  GCC  CCG  GGG  CAG  ACA  GCT  CAA  CTT  CAG  CTA  AAT  GCT     1107
Val  Pro  Ala  Ala  Ala  Pro  Gly  Gln  Thr  Ala  Gln  Leu  Gln  Leu  Asn  Ala
350                           355                       360

ACC  GAG  AGT  GAC  GAC  GGA  CGC  AGC  TTC  TTC  TGC  AGT  GCC  ACT  CTC  GAG     1155
Thr  Glu  Ser  Asp  Asp  Gly  Arg  Ser  Phe  Phe  Cys  Ser  Ala  Thr  Leu  Glu
365                           370                       375                       380

GTG  GAC  GGC  GAG  TTC  TTG  CAC  AGG  AAC  AGT  AGC  GTC  CAG  CTG  CGA  GTC     1203
Val  Asp  Gly  Glu  Phe  Leu  His  Arg  Asn  Ser  Ser  Val  Gln  Leu  Arg  Val
                              385                       390                       395

CTG  TAT  GGT  CCC  AAA  ATT  GAC  CGA  GCC  ACA  TGC  CCC  CAG  CAC  TTG  AAA     1251
Leu  Tyr  Gly  Pro  Lys  Ile  Asp  Arg  Ala  Thr  Cys  Pro  Gln  His  Leu  Lys
               400                       405                       410

TGG  AAA  GAT  AAA  ACG  AGA  CAC  GTC  CTG  CAG  TGC  CAA  GCC  AGG  GGC  AAC     1299
Trp  Lys  Asp  Lys  Thr  Arg  His  Val  Leu  Gln  Cys  Gln  Ala  Arg  Gly  Asn
               415                       420                       425

CCG  TAC  CCC  GAG  CTG  CGG  TGT  TTG  AAG  GAA  GGC  TCC  AGC  CGG  GAG  GTG     1347
Pro  Tyr  Pro  Glu  Leu  Arg  Cys  Leu  Lys  Glu  Gly  Ser  Ser  Arg  Glu  Val
     430                       435                       440

CCG  GTG  GGG  ATC  CCG  TTC  TTC  GTC  AAC  GTA  ACA  CAT  AAT  GGT  ACT  TAT     1395
Pro  Val  Gly  Ile  Pro  Phe  Phe  Val  Asn  Val  Thr  His  Asn  Gly  Thr  Tyr
445                           450                       455                       460

CAG  TGC  CAA  GCG  TCC  AGC  TCA  CGA  GGC  AAA  TAC  ACC  CTG  GTC  GTG  GTG     1443
Gln  Cys  Gln  Ala  Ser  Ser  Ser  Arg  Gly  Lys  Tyr  Thr  Leu  Val  Val  Val
               465                       470                       475

ATG  GAC  ATT  GAG  GCT  GGG  AGC  TCC  CAC  TTT  GTC  CCC  GTC  TTC  GTG  GCG     1491
Met  Asp  Ile  Glu  Ala  Gly  Ser  Ser  His  Phe  Val  Pro  Val  Phe  Val  Ala
               480                       485                       490

GTG  TTA  CTG  ACC  CTG  GGC  GTG  GTG  ACT  ATC  GTA  CTG  GCC  TTA  ATG  TAC     1539
Val  Leu  Leu  Thr  Leu  Gly  Val  Val  Thr  Ile  Val  Leu  Ala  Leu  Met  Tyr
               495                       500                       505

GTC  TTC  AGG  GAG  CAC  CAA  CGG  AGC  GGC  AGT  TAC  CAT  GTT  AGG  GAG  GAG     1587
Val  Phe  Arg  Glu  His  Gln  Arg  Ser  Gly  Ser  Tyr  His  Val  Arg  Glu  Glu
     510                       515                       520

AGC  ACC  TAT  CTG  CCC  CTC  ACG  TCT  ATG  CAG  CCG  ACA  GAA  GCA  ATG  GGG     1635
Ser  Thr  Tyr  Leu  Pro  Leu  Thr  Ser  Met  Gln  Pro  Thr  Glu  Ala  Met  Gly
525                           530                       535                       540

GAA  GAA  CCG  TCC  AGA  GCT  GAG  TGACGCTGGG ATCCGGGATC AAAGTTGGCG                 1686
Glu  Glu  Pro  Ser  Arg  Ala  Glu
                    545

GGGGCTTGGC TGTGCCCTCA GATTCCGCAC CAATAAAGCC TTCAAACTCC CAAAAAAAAA                  1746
```

| AAAAAAAAA | AAAAAAAAA | AAAAAAAAA | AAAAA | | 1781 |

(2) INFORMATION FOR SEQ ID NO:5:

(i) SEQUENCE CHARACTERISTICS:
        (A) LENGTH: 4900 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

| CCGAACGCTC | CTCGGCCTCT | GGTCTNCTCT | GGNCCTGGGG | ATCCTAGGCA | TCTCAGGTAA | 60 |
| GAAGAGCCCG | CCCGTGGAGC | NAGGTGGATA | AGGCGGGGGC | GGAATTGAAG | GACCAGAGAG | 120 |
| GGCGGCCCGG | GTGTCCCCCT | CCAGGCTCCG | CCCTCTTCTA | GCTTCCACG | CTTCTGTCAC | 180 |
| CACCTGGAGN | TCGGGGCTTC | TCCCCGTCCT | TCCTCCACCC | CAACACACCT | CAATCTTTCA | 240 |
| GANCTGAACC | CAGCACCTTT | TCTGGANTNG | GGGNNTTGCA | CCTAACCTGT | CTCAGGAGAN | 300 |
| ACTGTGGCTC | TCCTGTCCTC | TCCTGCTCTG | TNATGCCCTA | TGGTTCACAG | ACTGGCATCA | 360 |
| TCCCTATTCA | TGATCCTCAA | AGACNCCATC | TCCTCAACTG | TCATAACTCA | GAGCTCTATT | 420 |
| CCCCCTCCAC | CTGGAGCCCT | GGAAACCGGC | TTTCTAGGGC | TTTTCTCCGC | GGTTCTTTCC | 480 |
| CGGAGTTCAG | CGTTGTGGCT | TTTTGTCCAA | GTTACTCAAG | TTTGGGGACA | ATCTCCTTTA | 540 |
| AGCCTTTGAC | TCAGTCTCAT | TTCCACTTTG | CTTTTGCCCC | AAGCCTCTGT | GTCTCTCCCC | 600 |
| CATTTCCTGA | CGATCTGTCA | GAGTCTTAAG | AGTGATTTGG | TTCCCCATCC | CCCTCCAAC | 660 |
| TGGAGTCTCC | TCCTCACTAT | TGATGTGTGC | ATCTGAGACC | CCCATCCCCG | CACCGAGTTT | 720 |
| CCCCATCTCT | GTCAGTAAAG | AGCAAGGCTT | CCAGAGACAA | CCCTCTAATA | GCGCGTCAGT | 780 |
| CCCGAATCTT | GAGTGGGATG | CGGGACTCCC | GTGCTATTTC | TTGGCGGAGG | TCTTTCCTGG | 840 |
| TCCTTATGGA | CACCCCTGGT | TTGGGATATG | GGGGCCGCTA | AGATTTCAGA | GATGGGGTCC | 900 |
| CTAGGCTGAG | NCCGCGTTTT | CCCGGGCAGC | GGTCGCGCTA | GAACCTTTCT | GGGCGGACCT | 960 |
| TCAGCCCCGC | GTGGCGCTCG | TGGAGCGCGG | GGGCTCGCTG | TGGCTCAACT | GCAGCACTAA | 1020 |
| CTGTCCGAGG | CCGGAGCGCG | GTGGCCTGGA | GACCTCGCTA | CGCCGAAACG | GGACCCAGAG | 1080 |
| GGGTCTGNAC | TGNCTGGCTC | GACAGCTGGT | GGACATCCGA | GANCCTGAAA | CCCAGCCGGT | 1140 |
| CTGCTTCTTC | CNCTGCGCGC | GCCGCACACT | CCAAGCGCGT | GGGCTCATCC | GAACTTTCCG | 1200 |
| TGAGTTCAGG | GTGGGCACNC | CCCTTGGGTC | TCTGGACCTC | CCCCTCAAGC | TCCTCCCACC | 1260 |
| CGCCCTCTGA | TCCTCCTGCT | TGTTCTGAAA | GTACTACAGC | TGGCTAGAGC | GGAGTTTTTG | 1320 |
| GTCCCTTGCA | GAGCGACCGG | ATCGGGTAGA | GCTAGTGCCT | CTGCCTCCTT | GGCAGCCTGT | 1380 |
| AGGTGAGAAC | TTCACCTTGA | GCTGCAGGGT | CCCGGGGCA | GGACCCCGAG | CGAGCCTCAC | 1440 |
| ATTGACCTTG | CTGCGAGGCG | GCCAGGAGCT | GATTCGCCGA | AGTTTCGTAG | GCGAGCCACC | 1500 |
| CCGAGCTCGG | GGTGCGATGC | TCACCGCCAC | GGTCCTGGCG | CGCAGAGAGG | ATCACAGGGC | 1560 |
| CAATTTCTCA | TGCCTCGCGG | AGCTTGACCT | GCGNCCACAC | GGCTTGGGAC | TGTTTGCANA | 1620 |
| CAGCTCAGCC | CCCAGACAGC | TCCGCACGTT | TGGTGAGTGT | GGACCCTAAC | TGACAGATTT | 1680 |
| TAAGAAGTTT | AGGGCAGCCA | GGCGTGGTGG | CATGGTGTCG | TAGGCCCTAA | GTCCCAGCCC | 1740 |
| AAGCAGANCT | AAGNCGGATC | TCTTGTGAAT | TAAAGTCTA | GCTCGTCTAC | ATAACGAGGN | 1800 |
| CTGCATAGTT | AAATCCCCA | AAAGTCTAAG | CAGCTAGCCC | TTACTTCCAA | CACAAGTACT | 1860 |
| AGCTTAAGTA | CTTTCTCCTG | TGAGCTTTTT | CCTTTATGTA | TTTACTCGTT | GAGAGAAAAA | 1920 |
| GAGAGTGTGT | GTACGTGCCT | TTATGCACAT | GCCGCAGTGC | TTGTATGGAA | GTTAAAGAAT | 1980 |

```
AAGGAGGCGT TCTGCCCTTC CATCCTGTGG GTCCTAGGGG TGGTATTAGC TCCTCAGGCT      2040
TTGTTAGTNA CAAGCGCCTA GGCTTGGGGA GCCATCTCGC CCGCTCCTCT GTATCTTTAG      2100
GGTGAAACCA GACAATGCAT GCAAATTGGT TGATCAACAC TGAATGTTTA GTTCGTAAAT      2160
TCAAGCTCTG TTCTTTGTCT TCCTCAGCCA TGCCTCCACT TTCCCCCGAG CCTTATTGCC      2220
CCACGATTCT TAGAAGTGGG CTCAGAAAGG CCGGTGACKT GCACTTTGGA TGGACTGTTT      2280
CCTGCCCCAG AAGCCGGGGT TTACTTCTCT CTGGGAGATC AGAGGCTTCA TCCTAATGTG      2340
ACCCTCGACG GGGAGAGCCT TGTGGCCACT GCCACAGCTA CAGCAAGTGA AGAACAGGAA      2400
GGCACCAAAC AGCTGATGTG CATCGTGACC CTCGGGGGCG AAAGCAGGGA GACCCAGGAA      2460
AACCTGACTG TCTACAGTAA GGGGAATCCA ACAAGACCTT CAATAGCTCA GACTGGGGCT      2520
GGGGCTGGGT CTGGGTCTGG GGCCAGAGTC TCACAAAGGC GGAGCCTATA AGTGGGCGG      2580
GACCTCCACA CCAGAACAAG CCGGGCGGGA GAGTTCCAGG GCAGGAGCAG ATAGAAGTTG      2640
GAAATTAATA GATTGGGTTG AGTTCCCTGA GTGGGAGTG AACCCCACCC AATTCTCTGT      2700
CCCCAGGCTT CCCGGCTCCT CTTCTGACTT TAAGTGAGCC AGAAGCCCCC GAGGGAAAGA      2760
TGGTGACCGT AAGCTGCTGG GCAGGGGCCC GAGCCCTTGT CACCTTGGAG GGAATTCCAA      2820
GGACCCTCTT ACCGGCCCCA TCTTTAACCT TATCGTATCC CCTCTGCCTC ATGCCCGCAG      2880
ACGCACCTCG GCTGGATGAC TTGGACTGTC CAGGAGCTG GACGTGGCCA GAGGGTCCAG       2940
AGCAGACCCT CCACTGCGAG GCCCGTGGAA ACCCTGAGCC CTCCGTGCAC TGTGCAAGGC      3000
CTGACGGTGG GGCGGTGCTA GCGCTGGGCC TGTTGGGTCC AGTGACCCGT GCCCTCGCGG      3060
GCACTTACCG ATGTACAGCA ATCAATGGGC AAGGCCAGGC GGTCAAGGAT GTGACCCTGA      3120
CTGTGGAATG TGAGTAGGGG GAGGTGGGCA TGCTTATCCC TTTAAGGTCA CGGAGTGTAC      3180
TGGGAGACTG GCTATACGGA AAGGAAAGAA GCCTAGGTTC AGCAGGGATT GGGAAAACAC      3240
TGAAGGAAAG TGGTGTGGTG TTTACAAACT TAACGGTGGT AACTGGGCAC GGTCTGGCAA      3300
AAACAGACAG CCAAGAGAGT GTGCCTGGGA AGCTGCAATG GGGGCTTTGT GGGAATTGGT      3360
CAACAGCACC CTGAGATCTC AGGAAGGGG CCTGAAGTTA TCTCCAGAAC CCATGTGAAG       3420
GCAGGAAGAG AGAACGCCCA CCTTTTCCTG CTCCCCCCAA CCCCCCCCCA CATATCACAC      3480
GGAGTATATA AATAAATAAA ATGGCTCCTG CCGGAGGGAG TGAGAAGCTG TCTCCTGCAG      3540
GCTCAGAGCA GTGGTAGTGC ATGCCTTTAA TCCCAGCACT CGGTAGGCAA AGGCAGGCAG      3600
ATCTCTGTGA ATGTGGGGCC AGCCTGGTCT GTACAGAGAA ATCCTGTCTC AAAACAAACC      3660
AGCAAAGAAA CAAAACCAAA ATCAATTCCA GATGCCCCAG CGCTGGACAG TGTAGGCTGC      3720
CCANGACGTA TTACTTGNCT GGAGGGGACA GAGGCATCGC TTAGCTGTGT GGCACACGGG      3780
GTCCCACCAC CTAGCGTGAG CTGTGTGCGC TCTGGAAAGG AGGAAGTCAT GGAAGGGCCC      3840
CTGCGTGTGG CCCGGGAGCA CGCTGGCACT TACCGATGCG AAGCCATCAA CGCCAGGGA      3900
TCAGCGGNCA AAAATGTGGC TGTCACGGTG GAATGTGAGT AGGGGTGGCT ACGGAAATGT      3960
CCACACCTGC GTCCTCTGTC CTCAGTGTGA ACTCCTATTT CCCTGCTTCC TAGATGGTCC      4020
CAGTTNTGAG GAGTTGGGCT GCCCCAGCAA CTGGACTTGG GTAGAAGGAT CTGGAAAACT      4080
GTTTTCCTGT GAAGTTGATG GGAAGCCGGA ACCACGCGTG GAGTGCGTGG GCTCGGAGGG      4140
TGCAAGCGAA GGGGTAGTGT TGCCCCTGGT GTCCTCGAAC TCTGGTTCCA GAAACTCTAT      4200
GACTCCTGGT AACCTGTCAC CGGGTATTTA CCTCTGCAAC GCCACCAACC GGCATGGCTC      4260
CACAGTCAAA ACAGTCGTCG TGAGCGCGGA ATGTGAGCAG GGGCCCAGGT GGGCGGAGAG      4320
TACCGGGTGT CCCAGGATCT TTTCTTTCCC TGATGCCCCT CCTTATGGTG GCTGATCTGC      4380
```

| | | | | | |
|---|---|---|---|---|---|
| AGCACCGCCA | CAGATGGATG | AATCCAGTTG | CCCGAGTCAC | CAGACATGGC | TGGAAGGAGC | 4440 |
| CGAGGCTACT | GCGCTGGCCT | GCAGTGACAG | GGGNCGCCCC | TCTCCACGCG | TGCGCTGTTC | 4500 |
| CAGGGAAGGT | GCAGCCAGGC | TGGAGAGGCT | ACAGGTGTCC | CGAGAGGATG | CGGGGACCTA | 4560 |
| CCTGTGTGTG | GCTACCAACG | CGCATGGCAC | GGATTCACGG | ACCGTCACTG | TGGGTGTGGA | 4620 |
| ATGTGAGTGA | GGACAGCGCT | GAATGAAGAC | GACTCAGACC | GCCAGAAAAG | TGCCTTGAGG | 4680 |
| CCTGGGATGT | ATGATCCAGT | GGGTAGAGTG | CTCAATTAGC | ACTCACTAAA | ATGTATATTC | 4740 |
| TATTCCTAAT | ACTCTTTAAT | TTTANCCTTT | GGGAGGCAGA | GACAGGCAGA | TCTCTGTTCC | 4800 |
| GGGATAACCT | GCTCTCTGTC | TAGGACAGCT | TGGTCTACAG | AGGGGNTACA | GGCCCCCCCT | 4860 |
| CCCAAGATTG | NATAGCAACC | CTCTGGCTCC | CTGTCTCTCT | | | 4900 |

( 2 ) INFORMATION FOR SEQ ID NO:6:

( i ) SEQUENCE CHARACTERISTICS:
        ( A ) LENGTH: 1295 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

| | | | | | |
|---|---|---|---|---|---|
| NGAATTCCGG | CGGATCGGGT | AGAGCTAGTG | CCTCTGCCTC | CTTGGCAGCC | TGTAGGTGAG | 60 |
| AACTTCACCT | TGAGCTGCAG | GGTCCCGGGG | GCAGGACCCC | GAGCGAGCCT | CACATTGACC | 120 |
| TTGCTGCGAG | GCGGCCAGGA | GCTGATTCGC | CGAAGTTTCG | TAGGCGAGCC | ACCCCGAGCT | 180 |
| CGGGGTGCGA | TGCTCACCGC | CACGGTCCTG | GCGCGCAGAG | AGGATCACAG | GCCAATTTC | 240 |
| TCATGCCTCG | CGGAGCTTGA | CCTGCGGCCA | CACGGCTTGG | GACTGTTTGC | AAACAGCTCA | 300 |
| GCCCCAGAC | AGCTCCGCAC | GTTTGCCATG | CCTCCACTTT | CCCCGAGCCT | TATTGCCCCA | 360 |
| CGATTCTTAG | AAGTGGGCTC | AGAAAGGCCG | GTGACTTGCA | CTTTGGATGG | ACTGTTTCCT | 420 |
| GCCCCAGAAG | CCGGGGTTTA | CCTCTCTCTG | GGAGATCAGA | GGCTTCATCC | TAATGTGACC | 480 |
| CTCGACGGGG | AGAGCCTTGT | GGCCACTGCC | ACAGCTACAG | CAAGTGAAGA | ACAGGAAGGC | 540 |
| ACCAAACAGC | TGATGTGCAT | CGTGACCCTC | GGGGCGAAA | GCAGGGAGAC | CCAGGAAAAC | 600 |
| CTGACTGTCT | ACAGCTTCCC | GGCTCCTCTT | CTGACTTTAA | GTGAGCCAGA | AGCCCCGAG | 660 |
| GGAAAGATGG | TGACCGTAAG | CTGCTGGGCA | GGGGCCCGAG | CCCTTGTCAC | CTTGGAGGGA | 720 |
| ATTCCAAGGA | CCCTCTTACC | GGCCCCATCT | TTAACCTTAT | CGTATCCCCT | CTGCCTCATG | 780 |
| CCCGCAGACG | CACCTCGGCT | GGATGACTTG | GACTGTCCCA | GGAGCTGGAC | GTGGCCAGAG | 840 |
| GGTCCAGAGC | AGACCCTCCA | CTGCGAGGCC | CGTGGAAACC | CTGAGCCCTC | CGTGCACTGT | 900 |
| GCAAGGCCTG | ACGGTGGGGC | GGTGCTAGCG | CTGGGCCTGT | TGGGTCCAGT | GACCCGTGCC | 960 |
| CTCGCGGGCA | CTTACCGATG | TACAGCAATC | AATGGGCAAG | GCCAGGCGGT | CAAGGATGTG | 1020 |
| ACCCTGACTG | TGGAATATGC | CCCAGCGCTG | GACAGTGTAG | GCTGCCCAGA | ACGTATTACT | 1080 |
| TGGCTGGAGG | GGACAGAGGC | ATCGCTTAGC | TGTGTGGCAC | ACGGGGTCCC | ACCACCTAGC | 1140 |
| GTGAGCTGTG | TGCGCTCTGG | AAAGGAGGAA | GTCATGGAAG | GGCCCCTGCG | TTTTGGCCGG | 1200 |
| GAGCACGCTG | GCACTTACCG | ATGCGAAGCC | ATCAACGCCA | GGGATCAGC | GGCCAAAAAT | 1260 |
| GTGGCTGTCA | CGGTGGAATA | TGGTCCCCGG | AATTC | | | 1295 |

( 2 ) INFORMATION FOR SEQ ID NO:7:

( i ) SEQUENCE CHARACTERISTICS:

(A) LENGTH: 2214 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:7:

| | | | | | | |
|---|---|---|---|---|---|---|
| CGAATCTTGA | GTGGGATGCG | GGACTCCCGT | GCTATTTCTT | GGCGGAGGTC | TTTCCTGGTC | 60 |
| CTTATGGACA | CCCCTGGTTT | GGGATATGGG | GGCCGCTAAG | ATTTCAGAGA | TGGGGTCCCT | 120 |
| AGGCTGAGCC | CGCGTTTTCC | CGGGCAGCGG | TCGCGCTAGA | ACCTTTCTGG | GCGGACCTTC | 180 |
| AGCCCCGCGT | GGCGCTCGTG | GAGCGCGGGG | GCTCGCTGTG | GCTCAACTGC | AGCACTAACT | 240 |
| GTCCGAGGCC | GGAGCGCGGT | GGYCTGGAGA | CCTCGCTACG | CCGAAACGGG | ACCCAGAGGG | 300 |
| GTCTGCGCTG | GCTGGCTCGA | CAGMTGGTGG | ACATCCGAGA | GCCTGAAACC | CAGTCGGTCT | 360 |
| GCTTCTTCCG | CTGGGCGCGC | CGCACACTCC | AAGNGAGTGG | GCTCATCCGA | ACTTTCCAGC | 420 |
| GACCGGATCG | GGTAGAGCTA | GTGCCTCTGN | CTCCTTGGCA | GCCTGTAGGT | GAGAACTTCA | 480 |
| CCTTGAGCTG | CAGGGTCCCG | GGGGCAGGAC | CCCGAGCGAG | CCTCACATTG | ACCTTGCTGC | 540 |
| GAGGCGGCCA | GGAGCTGATT | CGCCGAAGTT | TCGTAGGCGA | GCCACCCCGA | GCTCGGGGTG | 600 |
| CGATGCTCAC | CGCCACGGTC | CTGGCGCGCA | GAGAGGATCA | CAGGGCCAAT | TTCTCATGCC | 660 |
| TCGCGGAGCT | TGACCTGCGG | ACACACGGCT | TGGGACTGTT | TGCAAACAGC | TCAGCCCCCA | 720 |
| GACAGCTCCG | CACGTTTGGC | ATGCCTCCAC | TTTCCCCGAG | CCTTATTGNC | CCACGATTCT | 780 |
| TAGAAGTGGG | CTCAGAAAGG | CCGGTGACTT | GCACTTTGGA | TGGACTGTTT | CCTGCCCCAG | 840 |
| AAGCCGGGGT | TTACCTCTCT | CTGGGAGATC | AGAGGCTTCA | TCCTAATGTG | ACCCTCGACG | 900 |
| GGGAGAGCCT | TGTGGCCACT | GNCACAGMTA | CAGCAAGTGA | AGAACAGGAA | GGCACCAAAC | 960 |
| AGCTGATGTG | CATCGTGACC | CTCGGGGGCG | AAAGCAGGGA | GACCCAGGAA | AACCTGACTG | 1020 |
| TCTACAGCTT | CCCGGCTCCT | CTTCTGACTT | TAAGTGAGCC | AGAAGCCCCC | GAGGGAAAGA | 1080 |
| TGGTGACCGT | AAGCTGCTGG | GCAGGGGCCC | GAGCCCTTGT | CACCTTGGAG | GGAATTCCAG | 1140 |
| CTGCGGTCCC | TGGGCAGCCC | GCTGAGCTCC | AGTTAAATGT | CACAAAGAAT | GACGACAAGC | 1200 |
| GGGGCTTCTT | CTGCGACGCT | GCCCTCGATG | TGGACGGGGA | AACTCTGAGA | AAGAACCAGA | 1260 |
| GCTCTGAGCT | TCGTGTTCTG | TACGCACCTC | GGCTGGATGA | CTTGGACTGT | CCCAGGAGCT | 1320 |
| GGACGTGGCC | AGAGGGTCCA | GAGCAGACCC | TCCACTGCGA | GGCCCGTGGA | AACCCTGAGC | 1380 |
| CCTCCGTGCA | CTGTGCAAGG | CCTGACGGTG | GGGCGGTGCT | AGCGCTGGGC | CTGTTGGGTC | 1440 |
| CAGTGACCCG | TGCCCTCGCG | GGAACTTACC | GATGTACAGC | AATCAATGGG | CAAGGCCAGG | 1500 |
| CGGTCAAGGA | TGTGACCCTG | ACTGTGGAAT | ATGCCCAGC | GCTGGACAGT | GTAGGCTGCC | 1560 |
| CAGAACGTAT | TACTTGGCTG | GAGGGGACAG | AGGCATCGCT | TAGCTGTGTG | GCACACGGGG | 1620 |
| TCCCACCACC | TAGCGTGAGC | TGTGTGCGCT | CTGGAAAGGA | GGAAGTCATG | GAAGGGCCCC | 1680 |
| TGCGTGTGGC | CCGGGAGCAC | GCTGGCACTT | ACCGATGCGA | AGCCATCAAC | GNCAGGGGAT | 1740 |
| CAGCGGWCAA | AAATGTGGCT | GTCACGGTGG | AATATGGTCC | CAGTTTGGAG | GAGTTGGGCT | 1800 |
| GCCCCAGYAA | CTGGACTTGG | GTAGAAGGAT | CTGGAAAACT | GTTTTCCTGT | GAAGTTGATG | 1860 |
| GGAAGCCGGA | ACCACGCGTG | GAGTGCGTGG | GCTCGGAGGG | TGCAAGCGAA | GGGGTAGTGT | 1920 |
| TGCCCCTGGT | GTCCTCGAAC | TCTGGTTCCA | GAAACTCTAT | GACTCCTGGT | AACCTGTCAC | 1980 |
| CGGGTATTTA | CCTCTGCAAC | GCCACCAACC | GGMATGGNTC | CACAGTCAAA | ACAGTCGTCG | 2040 |
| TGAGCGCGGA | ATCACCGCCA | CAGATGGATG | AATCCAGTTG | CCCGAGTCAC | CAGACATGGN | 2100 |
| TGGAAGGAGC | CGAGGNTACT | GCGCTGGCCT | GCAGTGCCAG | AGGNCGCCCC | TCTCCACGCG | 2160 |

TGCGCTGTTC CAGGGAAGGT GCAGMCAGGC TGGAGAGGNT ACAGGTGTCC CGAG 2214

(2) INFORMATION FOR SEQ ID NO:8:

(i) SEQUENCE CHARACTERISTICS:
    (A) LENGTH: 5077 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:8:

| | | | | | |
|---|---|---|---|---|---|
| CCGAACGCTC | CTCGGCCTCT | GGTCTNCTCT | GGNCCTGGGG | ATCCTAGGCA | TCTCAGGTAA | 60 |
| GAAGAGCCCG | CCCGTGGAGC | NAGGTGGATA | AGGCGGGGGC | GGAATTGAAG | GACCAGAGAG | 120 |
| GGCGGCCCGG | GTGTCCCCCT | CCAGGCTCCG | CCCTCTTCTA | GCTTCCCACG | CTTCTGTCAC | 180 |
| CACCTGGAGN | TCGGGGCTTC | TCCCCGTCCT | TCCTCCACCC | CAACACACCT | CAATCTTTCA | 240 |
| GANCTGAACC | CAGCACCTTT | TCTGGANTNG | GGGNNTTGCA | CCTAACCTGT | CTCAGGAGAN | 300 |
| ACTGTGGCTC | TCCTGTCCTC | TCCTGCTCTG | TNATGCCCTA | TGGTTCACAG | ACTGGCATCA | 360 |
| TCCCTATTCA | TGATCCTCAA | AGACNCCATC | TCCTCAACTG | TCATAACTCA | GAGCTCTATT | 420 |
| CCCCCTCCAC | CTGGAGCCCT | GGAAACCGGC | TTTCTAGGGC | TTTTCTCCGC | GGTTCTTTCC | 480 |
| CGGAGTTCAG | CGTTGTGGCT | TTTTGTCCAA | GTTACTCAAG | TTTGGGGACA | ATCTCCTTTA | 540 |
| AGCCTTTGAC | TCAGTCTCAT | TTCCACTTTG | CTTTTGCCCC | AAGCCTCTGT | GTCTCTCCCC | 600 |
| CATTTCCTGA | CGATCTGTCA | GAGTCTTAAG | AGTGATTTGG | TTCCCCATCC | CCCTCCAAC | 660 |
| TGGAGTCTCC | TCCTCACTAT | TGATGTGTGC | ATCTGAGACC | CCCATCCCCG | CACCGAGTTT | 720 |
| CCCCATCTCT | GTCAGTAAAG | AGCAAGGCTT | CCAGAGACAA | CCCTCTAATA | GCGCGTCAGT | 780 |
| CCCGAATCTT | GAGTGGGATG | CGGGACTCCC | GTGCTATTTC | TTGGCGGAGG | TCTTTCCTGG | 840 |
| TCCTTATGGA | CACCCCTGGT | TTGGGATATG | GGGGCCGCTA | AGATTTCAGA | GATGGGTCC | 900 |
| CTAGGCTGAG | NCCGCGTTTT | CCCGGGCAGC | GGTCGCGCTA | GAACCTTTCT | GGGCGGACCT | 960 |
| TCAGCCCCGC | GTGGCGCTCG | TGGAGCGCGG | GGGCTCGCTG | TGGCTCAACT | GCAGCACTAA | 1020 |
| CTGTCCGAGG | CCGGAGCGCG | GTGGCCTGGA | GACCTCGCTA | CGCCGAAACG | GGACCCAGAG | 1080 |
| GGGTCTGNAC | TGNCTGGCTC | GACAGCTGGT | GGACATCCGA | GANCCTGAAA | CCCAGCCGGT | 1140 |
| CTGCTTCTTC | CNCTGCGCGC | GCCGCACACT | CCAAGCGCGT | GGGCTCATCC | GAACTTTCCG | 1200 |
| TGAGTTCAGG | GTGGGCACNC | CCCTTGGGTC | TCTGGACCTC | CCCCTCAAGC | TCCTCCCACC | 1260 |
| CGCCCTCTGA | TCCTCCTGCT | TGTTCTGAAA | GTACTACAGC | TGGCTAGAGC | GGAGTTTTG | 1320 |
| GTCCCTTGCA | GAGCGACCGG | ATCGGGTAGA | GCTAGTGCCT | CTGCCTCCTT | GGCAGCCTGT | 1380 |
| AGGTGAGAAC | TTCACCTTGA | GCTGCAGGGT | CCCGGGGCA | GGACCCCGAG | CGAGCCTCAC | 1440 |
| ATTGACCTTG | CTGCGAGGCG | GCCAGGAGCT | GATTCGCCGA | AGTTTCGTAG | GCGAGCCACC | 1500 |
| CCGAGCTCGG | GGTGCGATGC | TCACCGCCAC | GGTCCTGGCG | CGCAGAGAGG | ATCACAGGGC | 1560 |
| CAATTTCTCA | TGCCTCGCGG | AGCTTGACCT | GCGNCCACAC | GGCTTGGGAC | TGTTTGCANA | 1620 |
| CAGCTCAGCC | CCCAGACAGC | TCCGCACGTT | TGGTGAGTGT | GGACCCTAAC | TGACAGATTT | 1680 |
| TAAGAAGTTT | AGGGCAGCCA | GGCGTGGTGG | CATGGTGTCG | TAGGCCCTAA | GTCCCAGCCC | 1740 |
| AAGCAGANCT | AAGNCGGATC | TCTTGTGAAT | TAAAAGTCTA | GCTCGTCTAC | ATAACGAGGN | 1800 |
| CTGCATAGTT | AAATCCCCCA | AAAGTCTAAG | CAGCTAGCCC | TTACTTCCAA | CACAAGTACT | 1860 |
| AGCTTAAGTA | CTTTCTCCTG | TGAGCTTTTT | CCTTTATGTA | TTTACTCGTT | GAGAGAAAAA | 1920 |

```
GAGAGTGTGT  GTACGTGCCT  TTATGCACAT  GCCGCAGTGC  TTGTATGGAA  GTTAAAGAAT    1980
AAGGAGGCGT  TCTGCCCTTC  CATCCTGTGG  GTCCTAGGGG  TGGTATTAGC  TCCTCAGGCT    2040
TTGTTAGTNA  CAAGCGCCTA  GGCTTGGGGA  GCCATCTCGC  CCGCTCCTCT  GTATCTTTAG    2100
GGTGAAACCA  GACAATGCAT  GCAAATTGGT  TGATCAACAC  TGAATGTTTA  GTTCGTAAAT    2160
TCAAGCTCTG  TTCTTTGTCT  TCCTCAGCCA  TGCCTCCACT  TTCCCCCGAG  CCTTATTGCC    2220
CCACGATTCT  TAGAAGTGGG  CTCAGAAAGG  CCGGTGACKT  GCACTTTGGA  TGGACTGTTT    2280
CCTGCCCCAG  AAGCCGGGGT  TTACTTCTCT  CTGGGAGATC  AGAGGCTTCA  TCCTAATGTG    2340
ACCCTCGACG  GGGAGAGCCT  TGTGGCCACT  GCCACAGCTA  CAGCAAGTGA  AGAACAGGAA    2400
GGCACCAAAC  AGCTGATGTG  CATCGTGACC  CTCGGGGGCG  AAAGCAGGGA  GACCCAGGAA    2460
AACCTGACTG  TCTACAGTAA  GGGGAATCCA  ACAAGACCTT  CAATAGCTCA  GACTGGGGCT    2520
GGGGCTGGGT  CTGGGTCTGG  GGCCAGAGTC  TCACAAAGGC  GGAGCCTATA  AAGTGGGCGG    2580
GACCTCCACA  CCAGAACAAG  CCGGGCGGGA  GAGTTCCAGG  GCAGGAGCAG  ATAGAAGTTG    2640
GAAATTAATA  GATTGGGTTG  AGTTCCCTGA  GTGGGGAGTG  AACCCCACCC  AATTCTCTGT    2700
CCCCAGGCTT  CCCGGCTCCT  CTTCTGACTT  TAAGTGAGCC  AGAAGCCCCC  GAGGGAAAGA    2760
TGGTGACCGT  AAGCTGCTGG  GCAGGGGCCC  GAGCCCTTGT  CACCTTGGAG  GGAATTCCAG    2820
CTGCGGTCCC  TGGGCAGCCC  GCTGAGCTCC  AGTTAAATGT  CACAAAGAAT  GACGACAAGC    2880
GGGGCTTCTT  CTGCGACGCT  GCCCTCGATG  TGGACGGGGA  AACTCTGAGA  AAGAACCAGA    2940
GCTCTGAGCT  TCGTGTTCTG  TGTGAGTGGA  TGTTCACTTT  ATCTCTGTGA  ATTCCAAGGA    3000
CCCTCTTACC  GGCCCCATCT  TTAACCTTAT  CGTATCCCCT  CTGCCTCATG  CCCGCAGACG    3060
CACCTCGGCT  GGATGACTTG  GACTGTCCCA  GGAGCTGGAC  GTGGCCAGAG  GTCCAGAGC     3120
AGACCCTCCA  CTGCGAGGCC  CGTGGAAACC  CTGAGCCCTC  CGTGCACTGT  GCAAGGCCTG    3180
ACGGTGGGGC  GGTGCTAGCG  CTGGGCCTGT  TGGGTCCAGT  GACCCGTGCC  CTCGCGGGCA    3240
CTTACCGATG  TACAGCAATC  AATGGGCAAG  GCCAGGCGGT  CAAGGATGTG  ACCCTGACTG    3300
TGGAATGTGA  GTAGGGGGAG  GTGGGCATGC  TTATCCCTTT  AAGGTCACGG  AGTGTACTGG    3360
GAGACTGGCT  ATACGGAAAG  GAAAGAAGCC  TAGGTTCAGC  AGGGATTGGG  AAAACACTGA    3420
AGGAAAGTGG  TGTGGTGTTT  ACAAACTTAA  CGGTGGTAAC  TGGGCACGGT  CTGGCAAAAA    3480
CAGACAGCCA  AGAGAGTGTG  CCTGGGAAGC  TGCAATGGGG  GCTTTGTGGG  AATTGGTCAA    3540
CAGCACCCTG  AGATCTCAGG  AAAGGGGCCT  GAAGTTATCT  CCAGAACCCA  TGTGAAGGCA    3600
GGAAGAGAGA  ACGCCCACCT  TTTCCTGCTC  CCCCCAACCC  CCCCCCACAT  ATCACACGGA    3660
GTATATAAAT  AAATAAAATG  GCTCCTGCCG  GAGGGAGTGA  GAAGCTGTCT  CCTGCAGGCT    3720
CAGAGCAGTG  GTAGTGCATG  CCTTTAATCC  CAGCACTCGG  TAGGCAAAGG  CAGGCAGATC    3780
TCTGTGAATG  TGGGGCCAGC  CTGGTCTGTA  CAGAGAAATC  CTGTCTCAAA  ACAAACCAGC    3840
AAAGAAACAA  AACCAAAATC  AATTCCAGAT  GCCCCAGCGC  TGGACAGTGT  AGGCTGCCCA    3900
NGACGTATTA  CTTGNCTGGA  GGGGACAGAG  GCATCGCTTA  GCTGTGTGGC  ACACGGGTC     3960
CCACCACCTA  GCGTGAGCTG  TGTGCGCTCT  GGAAAGGAGG  AAGTCATGGA  AGGGCCCTG     4020
CGTGTGGCCC  GGGAGCACGC  TGGCACTTAC  CGATGCGAAG  CCATCAACGC  CAGGGGATCA    4080
GCGGNCAAAA  ATGTGGCTGT  CACGGTGGAA  TGTGAGTAGG  GGTGGCTACG  GAAATGTCCA    4140
CACCTGCGTC  CTCTGTCCTC  AGTGTGAACT  CCTATTTCCC  TGCTTCCTAG  ATGGTCCCAG    4200
TTNTGAGGAG  TTGGGCTGCC  CCAGCAACTG  GACTTGGGTA  GAAGGATCTG  GAAAACTGTT    4260
TTCCTGTGAA  GTTGATGGGA  AGCCGGAACC  ACGCGTGGAG  TGCGTGGGCT  CGGAGGGTGC    4320
```

| | | | | | | |
|---|---|---|---|---|---|---|
| AAGCGAAGGG | GTAGTGTTGC | CCCTGGTGTC | CTCGAACTCT | GGTTCCAGAA | ACTCTATGAC | 4380 |
| TCCTGGTAAC | CTGTCACCGG | GTATTTACCT | CTGCAACGCC | ACCAACCGGC | ATGGCTCCAC | 4440 |
| AGTCAAAACA | GTCGTCGTGA | GCGCGGAATG | TGAGCAGGGG | CCCAGGTGGG | CGGAGAGTAC | 4500 |
| CGGGTGTCCC | AGGATCTTTT | CTTTCCCTGA | TGCCCTCCT | TATGGTGGCT | GATCTGCAGC | 4560 |
| ACCGCCACAG | ATGGATGAAT | CCAGTTGCCC | GAGTCACCAG | ACATGGCTGG | AAGGAGCCGA | 4620 |
| GGCTACTGCG | CTGGCCTGCA | GTGACAGGGG | NCGCCCTCT | CCACGCGTGC | GCTGTTCCAG | 4680 |
| GGAAGGTGCA | GCCAGGCTGG | AGAGGCTACA | GGTGTCCCGA | GAGGATGCGG | GGACCTACCT | 4740 |
| GTGTGTGGCT | ACCAACGCGC | ATGGCACGGA | TTCACGGACC | GTCACTGTGG | GTGTGGAATG | 4800 |
| TGAGTGAGGA | CAGCGCTGAA | TGAAGACGAC | TCAGACCGCC | AGAAAAGTGC | CTTGAGGCCT | 4860 |
| GGGATGTATG | ATCCAGTGGG | TAGAGTGCTC | AATTAGCACT | CACTAAAATG | TATATTCTAT | 4920 |
| TCCTAATACT | CTTTAATTTT | ANCCTTTGGG | AGGCAGAGAC | AGGCAGATCT | CTGTTCCGGG | 4980 |
| ATAACCTGCT | CTCTGTCTAG | GACAGCTTGG | TCTACAGAGG | GGNTACAGGC | CCCCCCTCCC | 5040 |
| AAGATTGNAT | AGCAACCCTC | TGGCTCCCTG | TCTCTCT | | | 5077 |

( 2 ) INFORMATION FOR SEQ ID NO:9:

( i ) SEQUENCE CHARACTERISTICS:
        ( A ) LENGTH: 1472 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

| | | | | | | |
|---|---|---|---|---|---|---|
| NGAATTCCGG | CGGATCGGGT | AGAGCTAGTG | CCTCTGCCTC | CTTGGCAGCC | TGTAGGTGAG | 60 |
| AACTTCACCT | TGAGCTGCAG | GGTCCCGGGG | GCAGGACCCC | GAGCGAGCCT | CACATTGACC | 120 |
| TTGCTGCGAG | GCGGCCAGGA | GCTGATTCGC | CGAAGTTTCG | TAGGCGAGCC | ACCCCGAGCT | 180 |
| CGGGGTGCGA | TGCTCACCGC | CACGGTCCTG | GCGCGCAGAG | AGGATCACAG | GGCCAATTTC | 240 |
| TCATGCCTCG | CGGAGCTTGA | CCTGCGGCCA | CACGGCTTGG | GACTGTTTGC | AAACAGCTCA | 300 |
| GCCCCCAGAC | AGCTCCGCAC | GTTTGCCATG | CCTCCACTTT | CCCCGAGCCT | TATTGCCCCA | 360 |
| CGATTCTTAG | AAGTGGGCTC | AGAAAGGCCG | GTGACTTGCA | CTTTGGATGG | ACTGTTTCCT | 420 |
| GCCCCAGAAG | CCGGGGTTTA | CCTCTCTCTG | GGAGATCAGA | GGCTTCATCC | TAATGTGACC | 480 |
| CTCGACGGGG | AGAGCCTTGT | GGCCACTGCC | ACAGCTACAG | CAAGTGAAGA | ACAGGAAGGC | 540 |
| ACCAAACAGC | TGATGTGCAT | CGTGACCCTC | GGGGGCGAAA | GCAGGGAGAC | CCAGGAAAAC | 600 |
| CTGACTGTCT | ACAGCTTCCC | GGCTCCTCTT | CTGACTTTAA | GTGAGCCAGA | AGCCCCCGAG | 660 |
| GGAAAGATGG | TGACCGTAAG | CTGCTGGGCA | GGGGCCCGAG | CCCTTGTCAC | CTTGGAGGGA | 720 |
| ATTCCAGCTG | CGGTCCCTGG | GCAGCCCGCT | GAGCTCCAGT | TAAATGTCAC | AAAGAATGAC | 780 |
| GACAAGCGGG | GCTTCTTCTG | CGACGCTGCC | CTCGATGTGG | ACGGGGAAAC | TCTGAGAAAG | 840 |
| AACCAGAGCT | CTGAGCTTCG | TGTTCTGTGT | GAGTGGATGT | TCACTTTATC | TCTGTGAATT | 900 |
| CCAAGGACCC | TCTTACCGGC | CCCATCTTTA | ACCTTATCGT | ATCCCTCTG | CCTCATGCCC | 960 |
| GCAGACGCAC | CTCGGCTGGA | TGACTTGGAC | TGTCCCAGGA | GCTGGACGTG | GCCAGAGGGT | 1020 |
| CCAGAGCAGA | CCCTCCACTG | CGAGGCCCGT | GGAAACCCTG | AGCCCTCCGT | GCACTGTGCA | 1080 |
| AGGCCTGACG | GTGGGGCGGT | GCTAGCGCTG | GGCCTGTTGG | GTCCAGTGAC | CCGTGCCCTC | 1140 |
| GCGGGCACTT | ACCGATGTAC | AGCAATCAAT | GGGCAAGGCC | AGGCGGTCAA | GGATGTGACC | 1200 |
| CTGACTGTGG | AATATGCCCC | AGCGCTGGAC | AGTGTAGGCT | GCCCAGAACG | TATTACTTGG | 1260 |

| | | | | | |
|---|---|---|---|---|---|
| CTGGAGGGGA | CAGAGGCATC | GCTTAGCTGT | GTGGCACACG | GGGTCCCACC | ACCTAGCGTG | 1320 |
| AGCTGTGTGC | GCTCTGGAAA | GGAGGAAGTC | ATGGAAGGGC | CCCTGCGTTT | TGGCCGGGAG | 1380 |
| CACGCTGGCA | CTTACCGATG | CGAAGCCATC | AACGCCAGGG | GATCAGCGGC | CAAAAATGTG | 1440 |
| GCTGTCACGG | TGGAATATGG | TCCCCGGAAT | TC | | | 1472 |

( 2 ) INFORMATION FOR SEQ ID NO:10:

( i ) SEQUENCE CHARACTERISTICS:
        ( A ) LENGTH: 2550 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:10:

| | | | | | |
|---|---|---|---|---|---|
| CCTCTGCCTC | CTTGGCAGCC | TGTAGGTGAG | AACTTCACCT | TGAGCTGCAG | GGTCCCGGGG | 60 |
| GCAGGACCCC | GAGCGAGCCT | CACATTGACC | TTGCTGCGAG | GCGGCCAGGA | GCTGATTCGC | 120 |
| CGAAGTTTCG | TAGGCGAGCC | ACCCCGAGCT | CGGGGTGCGA | TGCTCACCGC | CACGGTCCTG | 180 |
| GCGCGCAGAG | AGGATCACAG | GGCCAATTTC | TCATGCCTCG | CGGAGCTTGA | CCTGCGGCCA | 240 |
| CACGGCTTGG | GACTGTTTGC | AAACAGCTCA | GCCCCAGAC | AGCTCCGCAC | GTTTGCCATG | 300 |
| CCTCCACTTT | CCCCGAGCCT | TATTGCCCCA | CGATTCTTAG | AAGTGGGCTC | AGAAAGGCCG | 360 |
| GTGACTTGCA | CTTTGGATGG | ACTGTTTCCT | GCCCCAGAAG | CCGGGGTTTA | CCTCTCTCTG | 420 |
| GGAGATCAGA | GGCTTCATCC | TAATGTGACC | CTCGACGGGG | AGAGCCTTGT | GGCCACTGCC | 480 |
| ACAGCTACAG | CAAGTGAAGA | ACAGGAAGGC | ACCAAACAGC | TGATGTGCAT | CGTGACCCTC | 540 |
| GGGGGCGAAA | GCAGGGAGAC | CCAGGAAAAC | CTGACTGTCT | ACAGCTTCCC | GGCTCCTCTT | 600 |
| CTGACTTTAA | GTGAGCCAGA | AGCCCCCGAG | GGAAAGATGG | TGACCGTAAG | CTGCTGGGCA | 660 |
| GGGGCCCGAG | CCCTTGTCAC | CTTGGAGGGA | ATTCCAGCTG | CGGTCCCTGG | GCAGCCGCT | 720 |
| GAGCTCCAGT | TAAATGTCAC | AAAGAATGAC | GACAAGCGGG | GCTTCTTCTG | CGACGCTGCC | 780 |
| CTCGATGTGG | ACGGGGAAAC | TCTGAGAAAG | AACCAGAGCT | CTGAGCTTCG | TGTTCTGTAC | 840 |
| GCACCTCGGC | TGGATGACTT | GGACTGTCCC | AGGAGCTGGA | CGTGGCCAGA | GGGTCCAGAG | 900 |
| CAGACCCTCC | ACTGCGAGGC | CCGTGGAAAC | CCTGAGCCCT | CCGTGCACTG | TGCAAGGCCT | 960 |
| GACGGTGGGG | CGGTGCTAGC | GCTGGGCCTG | TTGGGTCCAG | TGACCCGTGC | CCTCGCGGGC | 1020 |
| ACTTACCGAT | GTACAGCAAT | CAATGGGCAA | GGCCAGGCGG | TCAAGGATGT | GACCCTGACT | 1080 |
| GTGGAATATG | CCCCAGCGCT | GGACAGTGTA | GGCTGCCCAG | AACGTATTAC | TTGGCTGGAG | 1140 |
| GGGACAGAGG | CATCGCTTAG | CTGTGTGGCA | CACGGGGTCC | CACCACCTAG | CGTGAGCTGT | 1200 |
| GTGCGCTCTG | GAAAGGAGGA | AGTCATGGAA | GGGCCCCTGC | GTGTGGCCCG | GGAGCACGCT | 1260 |
| GGCACTTACC | GATGCGAAGC | CATCAACGCC | AGGGGATCAG | CGGCCAAAAA | TGTGGCTGTC | 1320 |
| ACGGTGGAAT | ATGGTCCCAG | TTTTGAGGAG | TTGGGCTGCC | CAGCAACTG | GACTTGGGTA | 1380 |
| GAAGGATCTG | GAAAACTGTT | TTCCTGTGAA | GTTGATGGGA | AGCCGGAACC | ACGCGTGGAG | 1440 |
| TGCGTGGGCT | CGGAGGGTGC | AAGCGAAGGG | GTAGTGTTGC | CCCTGGTGTC | CTCGAACTCT | 1500 |
| GGTTCCAGAA | ACTCTATGAC | TCCTGGTAAC | CTGTCACCGG | GTATTTACCT | CTGCAACGCC | 1560 |
| ACCAACCGGC | ATGGCTCCAC | AGTCAAAACA | GTCGTCGTGA | GCGCGGAATC | ACCGCCACAG | 1620 |
| ATGGATGAAT | CCAGTTGCCC | GAGTCACCAG | ACATGGCTGG | AAGGAGCCGA | GGCTACTGCG | 1680 |
| CTGGCCTGCA | GTGCCAGAGG | CCGCCCCTCT | CCACGCGTGC | GCTGTTCCAG | GGAAGGTGCA | 1740 |

| | | | | | |
|---|---|---|---|---|---|
| GCCAGGCTGG | AGAGGCTACA | GGTGTCCCGA | GAGGATGCGG | GGACCTACCT | GTGTGTGGCT | 1800 |
| ACCAACGCGC | ATGGCACGGA | TTCACGGACC | GTCACTGTGG | GTGTGGAATA | CCGGCCTGTG | 1860 |
| GTGGCTGAGC | TGGCAGCCTC | GCCCCCAAGC | GTGCGGCCTG | GCGGAAACTT | CACTCTGACC | 1920 |
| TGCCGTGCAG | AGGCCTGGCC | TCCAGCCCAG | ATCAGCTGGC | GCGCGCCCCC | GGGAGCTCTC | 1980 |
| AACCTCGGTC | TCTCCAGCAA | CAACAGCACG | CTGAGCGTGG | CGGGTGCCAT | GGGCAGCCAT | 2040 |
| GGTGGCGAGT | ATGAGTGCGC | AGCCACCAAT | GCGCATGGGC | GCCACGCACG | GCGCATCACG | 2100 |
| GTGCGCGTGG | CCGGTCCATG | GCTGTGGGTC | GCTGTGGGCG | GTGCGGCAGG | GGGCGCGGCG | 2160 |
| CTGCTGGCCG | CAGGGGCCGG | CCTGGCCTTC | TACGTGCAGT | CCACCGCTTG | CAAGAAGGGA | 2220 |
| GAGTACAACG | TCCAGGAGGC | TGAGAGCTCA | GGCGAGGCGG | TGTGTCTCAA | TGGCGCGGGC | 2280 |
| GGGACACCGG | GTGCAGAAGG | CGGAGCAGAG | ACCCCCGGCA | CTGCCGAGTC | ACCTGCAGAT | 2340 |
| GGCGAGGTTT | TCGCCATCCA | GCTGACATCT | TCCTGAGCCT | GTATCCAGCT | CCCCCAGGGG | 2400 |
| CCTCGAAAGC | ACAGGGGTGG | ACGTATGTAT | TGTTCACTCT | CTATTTATTC | AACTCCAGGG | 2460 |
| GCGTCGTCCC | CGTTTTCTAC | CCATTCCCTT | AATAAAGTTT | TTATAGGAGA | AAAAAAAAA | 2520 |
| AAAAAAAAAA | AAAAAAAAAA | AAAAAAAAA | | | | 2550 |

( 2 ) INFORMATION FOR SEQ ID NO:11:

( i ) SEQUENCE CHARACTERISTICS:
        ( A ) LENGTH: 222 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

| | | | | | |
|---|---|---|---|---|---|
| AATTCGATCA | CTCGCGCTCC | CCTCGCCTTC | TGCGCTCTCC | CCTCCCTGGC | AGCGGCGGCA | 60 |
| ATGCCGGGGC | CTTCACCAGG | GCTGCGCCGA | ACGCTCCTCG | GCCTCTGGGC | TGCCCTGGGC | 120 |
| CTGGGGATCC | TAGGCATCTC | AGCGGTCGCG | CTAGAACCTT | TCTGGGCGGA | CCTTCAGCCC | 180 |
| CGCGTGGCGC | TCGTGGAGCG | CGGGGGCTCG | CTGTGGCTCA | AC | | 222 |

( 2 ) INFORMATION FOR SEQ ID NO:12:

( i ) SEQUENCE CHARACTERISTICS:
        ( A ) LENGTH: 292 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:12:

| | | | | | |
|---|---|---|---|---|---|
| TGTGGAGCTG | GCACCCCTGC | CTCCTTGGCA | GCCGGTGGGC | CAGAACTTCA | CCCTGCGCTG | 60 |
| CCAAGTGGAG | GGTGGGTCGC | CCCGGACCAG | CCTCACGGTG | GTGCTGCTTC | GCTGGGAGGA | 120 |
| GGAGCTGAGC | CGGCAGCCCG | CAGTGGAGGA | GCCAGCGGAG | GTCACTGCCA | CTGTGCTGGC | 180 |
| CAGCAGAGAC | GACCACGGAG | CCCCTTTCTC | ATGCCGCACA | GAACTGGACA | TGCAGCCCCA | 240 |
| GGGGCTGGGA | CTGTTCGTGA | ACACCTCAGC | CCCCCGCCAG | CTCCGAACCT | TT | 292 |

( 2 ) INFORMATION FOR SEQ ID NO:13:

( i ) SEQUENCE CHARACTERISTICS:
        ( A ) LENGTH: 105 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:13:

```
Pro  Asp  Arg  Val  Glu  Leu  Val  Pro  Leu  Pro  Pro  Trp  Gln  Pro  Val  Gly
 1              5                        10                        15

Glu  Asn  Phe  Thr  Leu  Ser  Cys  Arg  Val  Pro  Gly  Ala  Gly  Pro  Arg  Ala
               20                       25                   30

Ser  Leu  Thr  Leu  Thr  Leu  Leu  Arg  Gly  Gly  Gln  Glu  Leu  Ile  Arg  Arg
              35                        40                       45

Ser  Phe  Val  Gly  Glu  Pro  Pro  Arg  Ala  Arg  Cys  Ala  Met  Leu  Thr  Ala
      50                       55                       60

Thr  Val  Leu  Ala  Arg  Arg  Glu  Asp  His  Arg  Asp  Asn  Phe  Ser  Cys  Leu
 65                  70                       75                            80

Ala  Glu  Leu  Asp  Leu  Arg  Thr  His  Gly  Leu  Gly  Leu  Phe  Ala  Asn  Ser
                    85                       90                      95

Ser  Ala  Pro  Arg  Gln  Leu  Arg  Thr  Phe
               100                      105
```

( 2 ) INFORMATION FOR SEQ ID NO:14:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:14:

GAACTCGAGG CCATGCCTCC ACTTTCC                              27

( 2 ) INFORMATION FOR SEQ ID NO:15:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:15:

CCATAAGCTT TATTCCACCG TGACAGCCAC                        30

( 2 ) INFORMATION FOR SEQ ID NO:16:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:16:

AACGTGCGGA GCTGTCTG                                          18

( 2 ) INFORMATION FOR SEQ ID NO:17:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear -continued (i i) MOLECULE TYPE: cDNA (x i) SEQUENCE DESCRIPTION: SEQ ID NO:17:

ACGGAATTCG AAGCCATCAA CGCCAGG 27

(2) INFORMATION FOR SEQ ID NO:18:

(i) SEQUENCE CHARACTERISTICS:
(A) LENGTH: 27 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:18:

CATGAATTCC GAATCTTGAG TGGGATG 27

(2) INFORMATION FOR SEQ ID NO:19:

(i) SEQUENCE CHARACTERISTICS:
(A) LENGTH: 27 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:19:

ATAGAATTCC TCGGGACACC TGTAGCC 27

(2) INFORMATION FOR SEQ ID NO:20:

(i) SEQUENCE CHARACTERISTICS:
(A) LENGTH: 18 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:20:

CARGGTGACA AGGGCTCG 18

(2) INFORMATION FOR SEQ ID NO:21:

(i) SEQUENCE CHARACTERISTICS:
(A) LENGTH: 27 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:21:

TATGAATTCA GTTGAGCCAC AGCGAGC 27

(2) INFORMATION FOR SEQ ID NO:22:

(i) SEQUENCE CHARACTERISTICS:
(A) LENGTH: 24 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:22:

CCGGGTCCTA GAGGTGGACA CGCA 24

( 2 ) INFORMATION FOR SEQ ID NO:23:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:23:

| | | | |
|---|---|---|---|
| TGCAGTGTCT CCTGGCTCTG GTTC | | | 24 |

( 2 ) INFORMATION FOR SEQ ID NO:24:

( i ) SEQUENCE CHARACTERISTICS:
        ( A ) LENGTH: 992 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:24:

```
GCGAAAACCG  GGAGACCCGG  GAGAACGTGA  CCATCTACAG  CTTCCCGGCA  CCACTCCTGA    60
CCCTGAGCGA  ACCCAGCGTC  TCCGAGGGGC  AGATGGTGAC  AGTAACCTGC  GCAGCTGGGG   120
CCCAAGCTCT  GGTCACACTG  GAGGGAGTTC  CAGCCGCGGT  CCCGGGGCAG  CCCGCCCAGC   180
TTCAGCTAAA  TGCCACCGAG  AACGACGACA  GACGCAGCTT  CTTCTGCGAC  GCCACCCTCG   240
ATGTGGACGG  GGAGACCCTG  ATCAAGAACA  GGAGCGCAGA  GCTTCGTGTC  CTATACGCTC   300
CCCGGCTAGA  CGATTCGGAC  TGCCCCAGGA  GTTGGACGTG  GCCCGAGGGC  CCAGAGCAGA   360
CGCTGCGCTG  CGAGGCCCGC  GGGAACCCAG  AACCCTCAGT  GCACTGTGCG  CGCTCCGACG   420
GCGGGGCCGT  GCTGGCTCTG  GGCCTGCTGG  GTCCAGTCAC  TCGGGCGCTC  TCAGGCACTT   480
ACCGCTGCAA  GGCGGCCAAT  GATCAAGGCG  AGGCGGTCAA  GGACGTAACG  CTAACGGTGG   540
AGTACGCACC  AGCGCTGGAC  AGCGTGGGCT  GCCCAGAACG  CATTACTTGG  CTGGAGGGAA   600
CAGAAGCCTC  GCTGAGCTGT  GTGGCGCACG  GGTACCGCC   GCCTGATGTG  ATCTGCGTGC   660
GCTCTGGAGA  ACTCGGGGCC  GTCATCGAGG  GGCTGTTGCG  TGTGGCCCGG  GAGCATGCGG   720
GCACTTACCG  CTGCGAAGCC  ACCAACCCTC  GGGGCTCTGC  GGCCAAAAAT  GTGGCCGTCA   780
CGGTGGAATA  TGGCCCCAGG  TTTGAGGAGC  CGAGCTGCCC  CAGCAATTGG  ACATGGGTGG   840
AAGGATCTGG  GCGCCTGTTT  TCCTGTGAGG  TCGATGGGAA  GCCACAGCCA  AGCGTGAAGT   900
GCGTGGGCTC  CGGGGCACCC  ACTGAGGGGG  TGCTGCTGCC  GCTGGCACCC  CCAGACCCTA   960
GTCCCAGAGC  TCCCAGAATC  CCTAGAGTCC  TG                                  992
```

( 2 ) INFORMATION FOR SEQ ID NO:25:

( i ) SEQUENCE CHARACTERISTICS:
        ( A ) LENGTH: 2775 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:25:

```
GCAGCCTCGC  GTGGCGTTCG  TGGAGCGCGG  GGGCTCGCTG  TGGCTGAATT  GCAGCACCAA    60
CTGCCCTCGG  CCGGAGCGCG  GTGGCCTGGA  GACCTCGCTG  CGCCGAAACG  GGACCCAGAG   120
```

| | | | | | |
|---|---|---|---|---|---|
| GGGTTTGCGT | TGGTTGGCGC | GGCAGCTGGT | GGACATTCGC | GAGCCGGAGA | CTCAGCCCGT | 180
| CTGCTTCTTC | CGCTGCGCGC | GGCGCACACT | ACAGGCGCGT | GGGCTCATTC | GCACTTTCCA | 240
| GCGACCAGAT | CGCGTAGAGC | TGATGCCGCT | GCCTCCCTGG | CAGCCGGTGG | GCGAGAACTT | 300
| CACCCTGAGC | TGTAGGGTCC | CCGGCGCCGG | GCCCCGTGCG | AGCCTCACGC | TGACCCTGCT | 360
| GCGGGGCGCC | CAGGAGCTGA | TCCGCCGCAG | CTTCGCCGGT | GAACCACCCC | GAGCGCGGGG | 420
| CGCGGTGCTC | ACAGCCACGG | TACTGGCTCG | GAGGGAGGAC | CATGGAGCCA | ATTTCTCGTG | 480
| TCGCGCCGAG | CTGGACCTGC | GGCCGCACGG | ACTGGGACTG | TTTGAAAACA | GCTCGGCCCC | 540
| CAGAGAGCTC | CGAACCTTCT | CCCTGTCTCC | GGATGCCCCG | CGCCTCGCTG | CTCCCCGGCT | 600
| CTTGGAAGTT | GGCTCGGAAA | GGCCCGTGAG | CTGCACTCTG | GACGGACTGT | TCCAGCCTC | 660
| AGAGGCCAGG | GTCTACCTCG | CACTGGGGGA | CCAGAATCTG | AGTCCTGATG | TCACCCTCGA | 720
| AGGGGACGCA | TTCGTGGCCA | CTGCCACAGC | CACAGCTAGC | GCAGAGCAGG | AGGGTGCCAG | 780
| GCAGCTGGTC | TGCAACGTCA | CCCTGGGGGG | CGAAAACCGG | GAGACCCGGG | AGAACGTGAC | 840
| CATCTACAGC | TTCCCGGCAC | CACTCCTGAC | CCTGAGCGAA | CCCAGCGTCT | CCGAGGGGCA | 900
| GATGGTGACA | GTAACCTGCG | CAGCTGGGGC | CCAAGCTCTG | GTCACACTGG | AGGGAGTTCC | 960
| AGCCGCGGTC | CCGGGGCAGC | CCGCCCAGCT | TCAGCTAAAT | GCCACCGAGA | ACGACGACAG | 1020
| ACGCAGCTTC | TTCTGCGACG | CCACCCTCGA | TGTGGACGGG | GAGACCCTGA | TCAAGAACAG | 1080
| GAGCGCAGAG | CTTCGTGTCC | TATACGCTCC | CCGGCTAGAC | GATTCGGACT | GCCCCAGGAG | 1140
| TTGGACGTGG | CCCGAGGGCC | CAGAGCAGAC | GCTGCGCTGC | GAGGCCCGCG | GAACCCAGA | 1200
| ACCCTCAGTG | CACTGTGCGC | GCTCCGACGG | CGGGGCCGTG | CTGGCTCTGG | GCCTGCTGGG | 1260
| TCCAGTCACT | CGGGCGCTCT | CAGGCACTTA | CCGCTGCAAG | GCGGCCAATG | ATCAAGGCGA | 1320
| GGCGGTCAAG | GACGTAACGC | TAACGGTGGA | GTACGCACCA | GCGCTGGACA | GCGTGGGCTG | 1380
| CCCAGAACGC | ATTACTTGGC | TGGAGGGAAC | AGAAGCCTCG | CTGAGCTGTG | TGGCGCACGG | 1440
| GGTACCGCCG | CCTGATGTGA | TCTGCGTGCG | CTCTGGAGAA | CTCGGGGCCG | TCATCGAGGG | 1500
| GCTGTTGCGT | GTGGCCCGGG | AGCATGCGGG | CACTTACCGC | TGCGAAGCCA | CCAACCCTCG | 1560
| GGGCTCTGCG | GCCAAAAATG | TGGCCGTCAC | GGTGGAATAT | GGCCCCAGGT | TTGAGGAGCC | 1620
| GAGCTGCCCC | AGCAATTGGA | CATGGGTGGA | AGGATCTGGG | CGCCTGTTTT | CCTGTGAGGT | 1680
| CGATGGGAAG | CCACAGCCAA | GCGTGAAGTG | CGTGGGCTCC | GGGGGCACCA | CTGAGGGGT | 1740
| GCTGCTGCCG | CTGGCACCCC | CAGACCCTAG | TCCCAGAGCT | CCCAGAATCC | CTAGAGTCCT | 1800
| GGCACCCGGT | ATCTACGTCT | GCAACGCCAC | CAACCGCCAC | GGCTCCGTGG | CCAAAACAGT | 1860
| CGTCGTGAGC | GCGGAGTCGC | CACCGGAGAT | GGATGAATCT | ACCTGCCCAA | GTCACCAGAC | 1920
| GTGGCTGGAA | GGGGCTGAGG | CTTCCGCGCT | GGCCTGCGCC | GCCCGGGGTC | GCCCTTCCCC | 1980
| AGGAGTGCGC | TGCTCTCGGG | AAGGCATCCC | ATGGCCTGAG | CAGCAGCGCG | TGTCCCGAGA | 2040
| GGACGCGGGC | ACTTACCACT | GTGTGGCCAC | CAATGCGCAT | GGCACGGACT | CCCGGACCGT | 2100
| CACTGTGGGC | GTGGAATACC | GGCCAGTGGT | GGCCGAACTT | GCTGCCTCGC | CCCCTGGAGG | 2160
| CGTGCGCCCA | GGAGGAAACT | TCACGTTGAC | CTGCCGCGCG | GAGGCCTGGC | CTCCAGCCCA | 2220
| GATCAGCTGG | CGCGCGCCCC | CGAGGGCCCT | CAACATCGGC | CTGTCGAGCA | ACAACAGCAC | 2280
| ACTGAGCGTG | GCAGGCGCCA | TGGGAAGCCA | CGGCGGCGAG | TACGAGTGCG | CACGCACCAA | 2340
| CGCGCACGGG | CGCCACGCGC | GGCGCATCAC | GGTGCGCGTG | GCCGGTCCGT | GGCTATGGGT | 2400
| CGCCGTGGGC | GGCGCGGCGG | GGGGCGCGG | GCTGCTGGCC | GCGGGGCCG | GCCTGGCCTT | 2460
| CTACGTGCAG | TCCACCGCCT | GCAAGAAGGG | CGAGTACAAC | GTGCAGGAGG | CCGAGAGCTC | 2520

| | | | | | |
|---|---|---|---|---|---|
| AGGCGAGGCC | GTGTGTCTGA | ACGGAGCGGG | CGGCGGCGCT | GGCGGGGCGG | CAGGCGCGGA | 2580
| GGGCGGACCC | GAGGCGGCGG | GGGGCGCGGC | CGAGTCGCCG | GCGGAGGGCG | AGGTCTTCGC | 2640
| CATACAGCTG | ACATCGGCGT | GAGCCCGCTC | CCCTCTCCGC | GGGCCGGGAC | GCCCCCCAGA | 2700
| CTCACACGGG | GGCTTATTTA | TTGCTTTATT | TATTTACTTA | TTCATTTATT | TATGTATTCA | 2760
| ACTCCAAGGG | AATTC | | | | | 2775

( 2 ) INFORMATION FOR SEQ ID NO:26:

( i ) SEQUENCE CHARACTERISTICS:
        ( A ) LENGTH: 1557 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:26:

| | | | | | |
|---|---|---|---|---|---|
| CGCGCTCTCC | TCGCCTCCTG | TGCTTTCCCC | GCCGCGGCGA | TGCCAGGGCC | TTCGCCAGGG | 60
| CTGCGCCGGG | CGCTACTCGG | CCTCTGGGCT | GCTCTGGGCC | TGGGGCTCTT | CGGCCTCTCA | 120
| GCGGTCTCGC | AGGAGCCCTT | CTGGGCGGAC | CTGCAGCCTC | GCGTGGCGTT | CGTGGAGCGC | 180
| GGGGGCTCGC | TGTGGCTGAA | TTGCAGCACC | AACTGCCCTC | GGCCGGAGCG | CGGTGGCCTG | 240
| GAGACCTCGC | TGCGCCGAAA | CGGGACCCAG | AGGGGTTTGC | GTTGGTTGGC | GCGGCAGCTG | 300
| GTGGACATTC | GCGAGCCGGA | GACTCAGCCC | GTCTGCTTCT | TCCGCTGCGC | GCGGCGCACA | 360
| CTACAGGCGC | GTGGGCTCAT | TCGCACTTTC | CAGCGACCAG | ATCGCGTAGA | GCTGATGCCG | 420
| CTGCCTCCCT | GGCAGCCGGT | GGGCGAGAAC | TTCACCCTGA | GCTGTAGGGT | CCCCGGCGCC | 480
| GGGCCCCGTG | CGAGCCTCAC | GCTGACCCTG | CTGCGGGGCG | CCCAGGAGCT | GATCCGCCGC | 540
| AGCTTCGCCG | GTGAACCACC | CCGAGCGCGG | GGCGCGGTGC | TCACAGCCAC | GGTACTGGCT | 600
| CGGAGGGAGG | ACCATGGAGC | CAATTTCTCG | TGTCGCGCCG | AGCTGGACCT | GCGGCCGCAC | 660
| GGACTGGGAC | TGTTTGAAAA | CAGCTCGGCC | CCAGAGAGC | TCCGAACCTT | CTCCCTGTCT | 720
| CCGGATGCCC | CGCGCCTCGC | TGCTCCCCGG | CTCTTGGAAG | TTGGCTCGGA | AAGGCCCGTG | 780
| AGCTGCACTC | TGGACGGACT | GTTTCCAGCC | TCAGAGGCCA | GGGTCTACCT | CGCACTGGGG | 840
| GACCAGAATC | TGAGTCCTGA | TGTCACCCTC | GAAGGGACG | CATTCGTGGC | CACTGCCACA | 900
| GCCACAGCTA | GCGCAGAGCA | GGAGGGTGCC | AGGCAGCTGG | TCTGCAACGT | CACCCTGGGG | 960
| GGCGAAAACC | GGGAGACCCG | GGAGAACGTG | ACCATCTACA | GCTTCCCGGC | ACCACTCCTG | 1020
| ACCCTGAGCG | AACCCAGCGT | CTCCGAGGGG | CAGATGGTGA | CAGTAACCTG | CGCAGCTGGG | 1080
| GCCCAAGCTC | TGGTCACACT | GGAGGGAGTT | CCAGCCGCGG | TCCCGGGGCA | GCCCGCCCAG | 1140
| CTTCAGCTAA | ATGCCACCGA | GAACGACGAC | AGACGCAGCT | TCTTCTGCGA | CGCCACCCTC | 1200
| GATGTGGACG | GGAGACCCT | GATCAAGAAC | AGGAGCGCAG | AGCTTCGTGT | CCTATACGCT | 1260
| CCCCGGCTAG | ACGATTCGGA | CTGCCCCAGG | AGTTGGACGT | GGCCCGAGGG | CCCAGAGCAG | 1320
| ACGCTGCGCT | GCGAGGCCCG | CGGGAACCCA | GAACCCTCAG | TGCACTGTGC | GCGCTCCGAC | 1380
| GGCGGGGCCG | TGCTGGCTCT | GGGCCTGCTG | GGTCCAGTCA | CTCGGGCGCT | CTCAGGCACT | 1440
| TACCGCTGCA | AGGCGGCCAA | TGATCAAGGC | GAGGCGGTCA | AGGACGTAAC | GCTAACGGTG | 1500
| GAGTACGCAC | CAGCGCTGGA | CAGCGTGGGC | TGCCCAGAAC | GCATTACTTG | GCTGGAG | 1557

( 2 ) INFORMATION FOR SEQ ID NO:27:

( i ) SEQUENCE CHARACTERISTICS:
        ( A ) LENGTH: 2927 base pairs ( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: CDS
( B ) LOCATION: 40..2814

( x i ) SEQUENCE DESCRIPTION: SEQ ID NO:27:

```
CGCGCTCTCC  TCGCCTCCTG  TGCTTTCCCC  GCCGCGGCG  ATG  CCA  GGG  CCT  TCG        54
                                              Met  Pro  Gly  Pro  Ser
                                               1                    5

CCA  GGG  CTG  CGC  CGG  GCG  CTA  CTC  GGC  CTC  TGG  GCT  GCT  CTG  GGC  CTG   102
Pro  Gly  Leu  Arg  Arg  Ala  Leu  Leu  Gly  Leu  Trp  Ala  Ala  Leu  Gly  Leu
               10                     15                          20

GGG  CTC  TTC  GGC  CTC  TCA  GCG  GTC  TCG  CAG  GAG  CCC  TTC  TGG  GCG  GAC   150
Gly  Leu  Phe  Gly  Leu  Ser  Ala  Val  Ser  Gln  Glu  Pro  Phe  Trp  Ala  Asp
                    25                     30                     35

CTG  CAG  CCT  CGC  GTG  GCG  TTC  GTG  GAG  CGC  GGG  GGC  TCG  CTG  TGG  CTG   198
Leu  Gln  Pro  Arg  Val  Ala  Phe  Val  Glu  Arg  Gly  Gly  Ser  Leu  Trp  Leu
               40                     45                          50

AAT  TGC  AGC  ACC  AAC  TGC  CCT  CGG  CCG  GAG  CGC  GGT  GGC  CTG  GAG  ACC   246
Asn  Cys  Ser  Thr  Asn  Cys  Pro  Arg  Pro  Glu  Arg  Gly  Gly  Leu  Glu  Thr
          55                          60                     65

TCG  CTG  CGC  CGA  AAC  GGG  ACC  CAG  AGG  GGT  TTG  CGT  TGG  TTG  GCG  CGG   294
Ser  Leu  Arg  Arg  Asn  Gly  Thr  Gln  Arg  Gly  Leu  Arg  Trp  Leu  Ala  Arg
 70                     75                     80                          85

CAG  CTG  GTG  GAC  ATT  CGC  GAG  CCG  GAG  ACT  CAG  CCC  GTC  TGC  TTC  TTC   342
Gln  Leu  Val  Asp  Ile  Arg  Glu  Pro  Glu  Thr  Gln  Pro  Val  Cys  Phe  Phe
                         90                     95                      100

CGC  TGC  GCG  CGG  CGC  ACA  CTA  CAG  GCG  CGT  GGG  CTC  ATT  CGC  ACT  TTC   390
Arg  Cys  Ala  Arg  Arg  Thr  Leu  Gln  Ala  Arg  Gly  Leu  Ile  Arg  Thr  Phe
              105                         110                       115

CAG  CGA  CCA  GAT  CGC  GTA  GAG  CTG  ATG  CCG  CTG  CCT  CCC  TGG  CAG  CCG   438
Gln  Arg  Pro  Asp  Arg  Val  Glu  Leu  Met  Pro  Leu  Pro  Pro  Trp  Gln  Pro
              120                         125                       130

GTG  GGC  GAG  AAC  TTC  ACC  CTG  AGC  TGT  AGG  GTC  CCC  GGC  GCC  GGG  CCC   486
Val  Gly  Glu  Asn  Phe  Thr  Leu  Ser  Cys  Arg  Val  Pro  Gly  Ala  Gly  Pro
              135                         140                       145

CGT  GCG  AGC  CTC  ACG  CTG  ACC  CTG  CTG  CGG  GGC  GCC  CAG  GAG  CTG  ATC   534
Arg  Ala  Ser  Leu  Thr  Leu  Thr  Leu  Leu  Arg  Gly  Ala  Gln  Glu  Leu  Ile
150                         155                         160                165

CGC  CGC  AGC  TTC  GCC  GGT  GAA  CCA  CCC  CGA  GCG  CGG  GGC  GCG  GTG  CTC   582
Arg  Arg  Ser  Phe  Ala  Gly  Glu  Pro  Pro  Arg  Ala  Arg  Gly  Ala  Val  Leu
                         170                         175                  180

ACA  GCC  ACG  GTA  CTG  GCT  CGG  AGG  GAG  GAC  CAT  GGA  GCC  AAT  TTC  TCG   630
Thr  Ala  Thr  Val  Leu  Ala  Arg  Arg  Glu  Asp  His  Gly  Ala  Asn  Phe  Ser
              185                         190                       195

TGT  CGC  GCC  GAG  CTG  GAC  CTG  CGG  CCG  CAC  GGA  CTG  GGA  CTG  TTT  GAA   678
Cys  Arg  Ala  Glu  Leu  Asp  Leu  Arg  Pro  His  Gly  Leu  Gly  Leu  Phe  Glu
              200                         205                       210

AAC  AGC  TCG  GCC  CCC  AGA  GAG  CTC  CGA  ACC  TTC  TCC  CTG  TCT  CCG  GAT   726
Asn  Ser  Ser  Ala  Pro  Arg  Glu  Leu  Arg  Thr  Phe  Ser  Leu  Ser  Pro  Asp
     215                         220                         225

GCC  CCG  CGC  CTC  GCT  GCT  CCC  CGG  CTC  TTG  GAA  GTT  GGC  TCG  GAA  AGG   774
Ala  Pro  Arg  Leu  Ala  Ala  Pro  Arg  Leu  Leu  Glu  Val  Gly  Ser  Glu  Arg
230                         235                         240                245

CCC  GTG  AGC  TGC  ACT  CTG  GAC  GGA  CTG  TTT  CCA  GCC  TCA  GAG  GCC  AGG   822
Pro  Val  Ser  Cys  Thr  Leu  Asp  Gly  Leu  Phe  Pro  Ala  Ser  Glu  Ala  Arg
              250                         255                       260
```

| | | | | | | | | | | | | | | | | |
|---|---|---|---|---|---|---|---|---|---|---|---|---|---|---|---|---|
| GTC | TAC | CTC | GCA | CTG | GGG | GAC | CAG | AAT | CTG | AGT | CCT | GAT | GTC | ACC | CTC | 870 |
| Val | Tyr | Leu | Ala | Leu | Gly | Asp | Gln | Asn | Leu | Ser | Pro | Asp | Val | Thr | Leu | |
| | | | 265 | | | | 270 | | | | | | 275 | | | |
| GAA | GGG | GAC | GCA | TTC | GTG | GCC | ACT | GCC | ACA | GCC | ACA | GCT | AGC | GCA | GAG | 918 |
| Glu | Gly | Asp | Ala | Phe | Val | Ala | Thr | Ala | Thr | Ala | Thr | Ala | Ser | Ala | Glu | |
| | | 280 | | | | | 285 | | | | | 290 | | | | |
| CAG | GAG | GGT | GCC | AGG | CAG | CTG | GTC | TGC | AAC | GTC | ACC | CTG | GGG | GGC | GAA | 966 |
| Gln | Glu | Gly | Ala | Arg | Gln | Leu | Val | Cys | Asn | Val | Thr | Leu | Gly | Gly | Glu | |
| | 295 | | | | | 300 | | | | | 305 | | | | | |
| AAC | CGG | GAG | ACC | CGG | GAG | AAC | GTG | ACC | ATC | TAC | AGC | TTC | CCG | GCA | CCA | 1014 |
| Asn | Arg | Glu | Thr | Arg | Glu | Asn | Val | Thr | Ile | Tyr | Ser | Phe | Pro | Ala | Pro | |
| 310 | | | | | 315 | | | | | 320 | | | | | 325 | |
| CTC | CTG | ACC | CTG | AGC | GAA | CCC | AGC | GTC | TCC | GAG | GGG | CAG | ATG | GTG | ACA | 1062 |
| Leu | Leu | Thr | Leu | Ser | Glu | Pro | Ser | Val | Ser | Glu | Gly | Gln | Met | Val | Thr | |
| | | | | 330 | | | | | 335 | | | | | 340 | | |
| GTA | ACC | TGC | GCA | GCT | GGG | GCC | CAA | GCT | CTG | GTC | ACA | CTG | GAG | GGA | GTT | 1110 |
| Val | Thr | Cys | Ala | Ala | Gly | Ala | Gln | Ala | Leu | Val | Thr | Leu | Glu | Gly | Val | |
| | | | 345 | | | | 350 | | | | | | 355 | | | |
| CCA | GCC | GCG | GTC | CCG | GGG | CAG | CCC | GCC | CAG | CTT | CAG | CTA | AAT | GCC | ACC | 1158 |
| Pro | Ala | Ala | Val | Pro | Gly | Gln | Pro | Ala | Gln | Leu | Gln | Leu | Asn | Ala | Thr | |
| | | 360 | | | | | 365 | | | | | 370 | | | | |
| GAG | AAC | GAC | GAC | AGA | CGC | AGC | TTC | TTC | TGC | GAC | GCC | ACC | CTC | GAT | GTG | 1206 |
| Glu | Asn | Asp | Asp | Arg | Arg | Ser | Phe | Phe | Cys | Asp | Ala | Thr | Leu | Asp | Val | |
| | 375 | | | | | 380 | | | | | 385 | | | | | |
| GAC | GGG | GAG | ACC | CTG | ATC | AAG | AAC | AGG | AGC | GCA | GAG | CTT | CGT | GTC | CTA | 1254 |
| Asp | Gly | Glu | Thr | Leu | Ile | Lys | Asn | Arg | Ser | Ala | Glu | Leu | Arg | Val | Leu | |
| 390 | | | | | 395 | | | | | 400 | | | | | 405 | |
| TAC | GCT | CCC | CGG | CTA | GAC | GAT | TCG | GAC | TGC | CCC | AGG | AGT | TGG | ACG | TGG | 1302 |
| Tyr | Ala | Pro | Arg | Leu | Asp | Asp | Ser | Asp | Cys | Pro | Arg | Ser | Trp | Thr | Trp | |
| | | | | 410 | | | | | 415 | | | | | 420 | | |
| CCC | GAG | GGC | CCA | GAG | CAG | ACG | CTG | CGC | TGC | GAG | GCC | CGG | GGA | AAC | CCA | 1350 |
| Pro | Glu | Gly | Pro | Glu | Gln | Thr | Leu | Arg | Cys | Glu | Ala | Arg | Gly | Asn | Pro | |
| | | | 425 | | | | | 430 | | | | | 435 | | | |
| GAA | CCC | TCA | GTG | CAC | TGT | GCG | CGC | TCC | GAC | GGC | GGG | GCC | GTG | CTG | GCT | 1398 |
| Glu | Pro | Ser | Val | His | Cys | Ala | Arg | Ser | Asp | Gly | Gly | Ala | Val | Leu | Ala | |
| | | 440 | | | | 445 | | | | | 450 | | | | | |
| CTG | GGC | CTG | CTG | GGT | CCA | GTC | ACT | CGG | GCG | CTC | TCA | GGC | ACT | TAC | CGC | 1446 |
| Leu | Gly | Leu | Leu | Gly | Pro | Val | Thr | Arg | Ala | Leu | Ser | Gly | Thr | Tyr | Arg | |
| | 455 | | | | | 460 | | | | | 465 | | | | | |
| TGC | AAG | GCG | GCC | AAT | GAT | CAA | GGC | GAG | GCG | GTC | AAG | GAC | GTA | ACG | CTA | 1494 |
| Cys | Lys | Ala | Ala | Asn | Asp | Gln | Gly | Glu | Ala | Val | Lys | Asp | Val | Thr | Leu | |
| 470 | | | | | 475 | | | | | 480 | | | | | 485 | |
| ACG | GTG | GAG | TAC | GCA | CCA | GCG | CTG | GAC | AGC | GTG | GGC | TGC | CCA | GAA | CGC | 1542 |
| Thr | Val | Glu | Tyr | Ala | Pro | Ala | Leu | Asp | Ser | Val | Gly | Cys | Pro | Glu | Arg | |
| | | | | 490 | | | | | 495 | | | | | 500 | | |
| ATT | ACT | TGG | CTG | GAG | GGA | ACA | GAA | GCC | TCG | CTG | AGC | TGT | GTG | GCG | CAC | 1590 |
| Ile | Thr | Trp | Leu | Glu | Gly | Thr | Glu | Ala | Ser | Leu | Ser | Cys | Val | Ala | His | |
| | | | 505 | | | | | 510 | | | | | 515 | | | |
| GGG | GTA | CCG | CCG | CCT | GAT | GTG | ATC | TGC | GTG | CGC | TCT | GGA | GAA | CTC | GGG | 1638 |
| Gly | Val | Pro | Pro | Pro | Asp | Val | Ile | Cys | Val | Arg | Ser | Gly | Glu | Leu | Gly | |
| | | 520 | | | | 525 | | | | | 530 | | | | | |
| GCC | GTC | ATC | GAG | GGG | CTG | TTG | CGT | GTG | GCC | CGG | GAG | CAT | GCG | GGC | ACT | 1686 |
| Ala | Val | Ile | Glu | Gly | Leu | Leu | Arg | Val | Ala | Arg | Glu | His | Ala | Gly | Thr | |
| | | 535 | | | | | 540 | | | | | 545 | | | | |
| TAC | CGC | TGC | GAA | GCC | ACC | AAC | CCT | CGG | GGC | TCT | GCG | GCC | AAA | AAT | GTG | 1734 |
| Tyr | Arg | Cys | Glu | Ala | Thr | Asn | Pro | Arg | Gly | Ser | Ala | Ala | Lys | Asn | Val | |
| 550 | | | | | 555 | | | | | 560 | | | | | 565 | |
| GCC | GTC | ACG | GTG | GAA | TAT | GGC | CCC | AGG | TTT | GAG | GAG | CCG | AGC | TGC | CCC | 1782 |
| Ala | Val | Thr | Val | Glu | Tyr | Gly | Pro | Arg | Phe | Glu | Glu | Pro | Ser | Cys | Pro | |
| | | | | 570 | | | | | 575 | | | | | 580 | | |

| | | | | | | | | | | | | | | | | |
|---|---|---|---|---|---|---|---|---|---|---|---|---|---|---|---|---|
| AGC | AAT | TGG | ACA | TGG | GTG | GAA | GGA | TCT | GGG | CGC | CTG | TTT | TCC | TGT | GAG | 1830 |
| Ser | Asn | Trp | Thr 585 | Trp | Val | Glu | Gly | Ser 590 | Gly | Arg | Leu | Phe | Ser 595 | Cys | Glu | |
| GTC | GAT | GGG | AAG | CCA | CAG | CCA | AGC | GTG | AAG | TGC | GTG | GGC | TCC | GGG | GGC | 1878 |
| Val | Asp | Gly 600 | Lys | Pro | Gln | Pro | Ser 605 | Val | Lys | Cys | Val | Gly 610 | Ser | Gly | Gly | |
| ACC | ACT | GAG | GGG | GTG | CTG | CTG | CCG | CTG | GCA | CCC | CCA | GAC | CCT | AGT | CCC | 1926 |
| Thr | Thr 615 | Glu | Gly | Val | Leu 620 | Leu | Pro | Leu | Ala | Pro 625 | Pro | Asp | Pro | Ser | Pro | |
| AGA | GCT | CCC | AGA | ATC | CCT | AGA | GTC | CTG | GCA | CCC | GGT | ATC | TAC | GTC | TGC | 1974 |
| Arg 630 | Ala | Pro | Arg | Ile 635 | Pro | Arg | Val | Leu | Ala 640 | Pro | Gly | Ile | Tyr | Val 645 | Cys | |
| AAC | GCC | ACC | AAC | CGC | CAC | GGC | TCC | GTG | GCC | AAA | ACA | GTC | GTC | GTG | AGC | 2022 |
| Asn | Ala | Thr | Asn 650 | Arg | His | Gly | Ser | Val 655 | Ala | Lys | Thr | Val | Val 660 | Val | Ser | |
| GCG | GAG | TCG | CCA | CCG | GAG | ATG | GAT | GAA | TCT | ACC | TGC | CCA | AGT | CAC | CAG | 2070 |
| Ala | Glu | Ser | Pro 665 | Pro | Glu | Met | Asp | Glu 670 | Ser | Thr | Cys | Pro | Ser 675 | His | Gln | |
| ACG | TGG | CTG | GAA | GGG | GCT | GAG | GCT | TCC | GCG | CTG | GCC | TGC | GCC | GCC | CGG | 2118 |
| Thr | Trp | Leu 680 | Glu | Gly | Ala | Glu | Ala 685 | Ser | Ala | Leu | Ala | Cys 690 | Ala | Ala | Arg | |
| GGT | CGC | CCT | TCC | CCA | GGA | GTG | CGC | TGC | TCT | CGG | GAA | GGC | ATC | CCA | TGG | 2166 |
| Gly | Arg 695 | Pro | Ser | Pro | Gly 700 | Val | Arg | Cys | Ser | Arg 705 | Glu | Gly | Ile | Pro | Trp | |
| CCT | GAG | CAG | CAG | CGC | GTG | TCC | CGA | GAG | GAC | GCG | GGC | ACT | TAC | CAC | TGT | 2214 |
| Pro 710 | Glu | Gln | Gln | Arg | Val 715 | Ser | Arg | Glu | Asp | Ala 720 | Gly | Thr | Tyr | His | Cys 725 | |
| GTG | GCC | ACC | AAT | GCG | CAT | GGC | ACG | GAC | TCC | CGG | ACC | GTC | ACT | GTG | GGC | 2262 |
| Val | Ala | Thr | Asn | Ala 730 | His | Gly | Thr | Asp | Ser 735 | Arg | Thr | Val | Thr | Val 740 | Gly | |
| GTG | GAA | TAC | CGG | CCA | GTG | GTG | GCC | GAA | CTT | GCT | GCC | TCG | CCC | CCT | GGA | 2310 |
| Val | Glu | Tyr | Arg 745 | Pro | Val | Val | Ala | Glu 750 | Leu | Ala | Ala | Ser | Pro 755 | Pro | Gly | |
| GGC | GTG | CGC | CCA | GGA | GGA | AAC | TTC | ACG | TTG | ACC | TGC | CGC | GCG | GAG | GCC | 2358 |
| Gly | Val | Arg 760 | Pro | Gly | Gly | Asn | Phe 765 | Thr | Leu | Thr | Cys | Arg 770 | Ala | Glu | Ala | |
| TGG | CCT | CCA | GCC | CAG | ATC | AGC | TGG | CGC | GCG | CCC | CGG | GCC | CTC | AAC | 2406 | |
| Trp 775 | Pro | Pro | Ala | Gln | Ile 780 | Ser | Trp | Arg | Ala | Pro 785 | Arg | Ala | Leu | Asn | | |
| ATC | GGC | CTG | TCG | AGC | AAC | AAC | AGC | ACA | CTG | AGC | GTG | GCA | GGC | GCC | ATG | 2454 |
| Ile 790 | Gly | Leu | Ser | Ser | Asn 795 | Asn | Ser | Thr | Leu | Ser 800 | Val | Ala | Gly | Ala | Met 805 | |
| GGA | AGC | CAC | GGC | GGC | GAG | TAC | GAG | TGC | GCA | CGC | ACC | AAC | GCG | CAC | GGG | 2502 |
| Gly | Ser | His | Gly | Gly 810 | Glu | Tyr | Glu | Cys | Ala 815 | Arg | Thr | Asn | Ala | His 820 | Gly | |
| CGC | CAC | GCG | CGG | CGC | ATC | ACG | GTG | CGC | GTG | GCC | GGT | CCG | TGG | CTA | TGG | 2550 |
| Arg | His | Ala | Arg 825 | Arg | Ile | Thr | Val | Arg 830 | Val | Ala | Gly | Pro | Trp 835 | Leu | Trp | |
| GTC | GCC | GTG | GGC | GGC | GCG | GCG | GGG | GCG | GCG | CTG | CTG | GCC | GCG | GGG | 2598 | |
| Val | Ala | Val 840 | Gly | Gly | Ala | Ala | Gly 845 | Gly | Ala | Ala | Leu | Leu 850 | Ala | Ala | Gly | |
| GCC | GGC | CTG | GCC | TTC | TAC | GTG | CAG | TCC | ACC | GCC | TGC | AAG | AAG | GGC | GAG | 2646 |
| Ala | Gly | Leu | Ala 855 | Phe | Tyr | Val | Gln | Ser 860 | Thr | Ala | Cys | Lys | Lys 865 | Gly | Glu | |
| TAC | AAC | GTG | CAG | GAG | GCC | GAG | AGC | TCA | GGC | GAG | GCC | GTG | TGT | CTG | AAC | 2694 |
| Tyr 870 | Asn | Val | Gln | Glu | Ala 875 | Glu | Ser | Ser | Gly | Glu 880 | Ala | Val | Cys | Leu | Asn 885 | |
| GGA | GCG | GGC | GGC | GGC | GCT | GGC | GGG | GCG | GCA | GGC | GCG | GAG | GGC | GGA | CCC | 2742 |
| Gly | Ala | Gly | Gly | Gly 890 | Ala | Gly | Gly | Ala | Ala 895 | Gly | Ala | Glu | Gly | Gly 900 | Pro | |

-continued

```
GAG  GCG  GCG  GGG  GGC  GCG  GCC  GAG  TCG  CCG  GCG  GAG  GGC  GAG  GTC  TTC         2790
Glu  Ala  Ala  Gly  Gly  Ala  Ala  Glu  Ser  Pro  Ala  Glu  Gly  Glu  Val  Phe
               905                      910                      915

GCC  ATA  CAG  CTG  ACA  TCG  GCG  TGAGCCCGCT  CCCCTCTCCG  CGGGCCGGGA                  2841
Ala  Ile  Gln  Leu  Thr  Ser  Ala
               920                      925

CGCCCCCCAG  ACTCACACGG  GGGCTTATTT  ATTGCTTTAT  TTATTTACTT  ATTCATTTAT                 2901

TTATGTATTC  AACTCCAAGG  GAATTC                                                         2927
```

( 2 ) INFORMATION FOR SEQ ID NO:28:

( i ) SEQUENCE CHARACTERISTICS:
        ( A ) LENGTH: 924 amino acids
        ( B ) TYPE: amino acid
        ( D ) TOPOLOGY: linear ( i i ) MOLECULE TYPE: protein ( x i ) SEQUENCE DESCRIPTION: SEQ ID NO:28:

```
Met  Pro  Gly  Pro  Ser  Pro  Gly  Leu  Arg  Arg  Ala  Leu  Leu  Gly  Leu  Trp
 1                    5                      10                      15

Ala  Ala  Leu  Gly  Leu  Gly  Leu  Phe  Gly  Leu  Ser  Ala  Val  Ser  Gln  Glu
               20                      25                      30

Pro  Phe  Trp  Ala  Asp  Leu  Gln  Pro  Arg  Val  Ala  Phe  Val  Glu  Arg  Gly
               35                      40                      45

Gly  Ser  Leu  Trp  Leu  Asn  Cys  Ser  Thr  Asn  Cys  Pro  Arg  Pro  Glu  Arg
      50                      55                      60

Gly  Gly  Leu  Glu  Thr  Ser  Leu  Arg  Arg  Asn  Gly  Thr  Gln  Arg  Gly  Leu
 65                      70                      75                      80

Arg  Trp  Leu  Ala  Arg  Gln  Leu  Val  Asp  Ile  Arg  Glu  Pro  Glu  Thr  Gln
                    85                      90                      95

Pro  Val  Cys  Phe  Phe  Arg  Cys  Ala  Arg  Arg  Thr  Leu  Gln  Ala  Arg  Gly
               100                     105                     110

Leu  Ile  Arg  Thr  Phe  Gln  Arg  Pro  Asp  Arg  Val  Glu  Leu  Met  Pro  Leu
               115                     120                     125

Pro  Pro  Trp  Gln  Pro  Val  Gly  Glu  Asn  Phe  Thr  Leu  Ser  Cys  Arg  Val
     130                     135                     140

Pro  Gly  Ala  Gly  Pro  Arg  Ala  Ser  Leu  Thr  Leu  Thr  Leu  Leu  Arg  Gly
145                     150                     155                     160

Ala  Gln  Glu  Leu  Ile  Arg  Arg  Ser  Phe  Ala  Gly  Glu  Pro  Pro  Arg  Ala
               165                     170                     175

Arg  Gly  Ala  Val  Leu  Thr  Ala  Thr  Val  Leu  Ala  Arg  Arg  Glu  Asp  His
               180                     185                     190

Gly  Ala  Asn  Phe  Ser  Cys  Arg  Ala  Glu  Leu  Asp  Leu  Arg  Pro  His  Gly
               195                     200                     205

Leu  Gly  Leu  Phe  Glu  Asn  Ser  Ser  Ala  Pro  Arg  Glu  Leu  Arg  Thr  Phe
     210                     215                     220

Ser  Leu  Ser  Pro  Asp  Ala  Pro  Arg  Leu  Ala  Ala  Pro  Arg  Leu  Leu  Glu
225                     230                     235                     240

Val  Gly  Ser  Glu  Arg  Pro  Val  Ser  Cys  Thr  Leu  Asp  Gly  Leu  Phe  Pro
               245                     250                     255

Ala  Ser  Glu  Ala  Arg  Val  Tyr  Leu  Ala  Leu  Gly  Asp  Gln  Asn  Leu  Ser
               260                     265                     270

Pro  Asp  Val  Thr  Leu  Glu  Gly  Asp  Ala  Phe  Val  Ala  Thr  Ala  Thr  Ala
               275                     280                     285

Thr  Ala  Ser  Ala  Glu  Gln  Glu  Gly  Ala  Arg  Gln  Leu  Val  Cys  Asn  Val
     290                     295                     300
```

| | | | | | | | | | | | | | | |
|---|---|---|---|---|---|---|---|---|---|---|---|---|---|---|
|Thr|Leu|Gly|Gly|Glu|Asn|Arg|Glu|Thr|Arg|Glu|Asn|Val|Thr|Ile|Tyr|
|305| | | | |310| | | |315| | | | | |320|
|Ser|Phe|Pro|Ala|Pro|Leu|Leu|Thr|Leu|Ser|Glu|Pro|Ser|Val|Ser|Glu|
| | | | |325| | | |330| | | | |335| | |
|Gly|Gln|Met|Val|Thr|Val|Thr|Cys|Ala|Ala|Gly|Ala|Gln|Leu|Val|
| | | |340| | | |345| | | |350| | | |
|Thr|Leu|Glu|Gly|Val|Pro|Ala|Ala|Val|Pro|Gly|Gln|Pro|Ala|Gln|Leu|
| | |355| | | |360| | | | |365| | | | |
|Gln|Leu|Asn|Ala|Thr|Glu|Asn|Asp|Arg|Arg|Ser|Phe|Phe|Cys|Asp|
| | |370| | | |375| | | |380| | | | |
|Ala|Thr|Leu|Asp|Val|Asp|Gly|Glu|Thr|Leu|Ile|Lys|Asn|Arg|Ser|Ala|
|385| | | |390| | | |395| | | | | | |400|
|Glu|Leu|Arg|Val|Leu|Tyr|Ala|Pro|Arg|Leu|Asp|Asp|Ser|Asp|Cys|Pro|
| | | | |405| | | |410| | | | |415| | |
|Arg|Ser|Trp|Thr|Trp|Pro|Glu|Gly|Pro|Glu|Gln|Thr|Leu|Arg|Cys|Glu|
| | | |420| | | |425| | | |430| | | | |
|Ala|Arg|Gly|Asn|Pro|Glu|Pro|Ser|Val|His|Cys|Ala|Arg|Ser|Asp|Gly|
| | |435| | | |440| | | |445| | | | | |
|Gly|Ala|Val|Leu|Ala|Leu|Gly|Leu|Leu|Gly|Pro|Val|Thr|Arg|Ala|Leu|
| |450| | | |455| | | |460| | | | | | |
|Ser|Gly|Thr|Tyr|Arg|Cys|Lys|Ala|Ala|Asn|Asp|Gln|Gly|Glu|Ala|Val|
|465| | | |470| | | |475| | | | | | |480|
|Lys|Asp|Val|Thr|Leu|Thr|Val|Glu|Tyr|Ala|Pro|Ala|Leu|Asp|Ser|Val|
| | | |485| | | |490| | | | |495| | | |
|Gly|Cys|Pro|Glu|Arg|Ile|Thr|Trp|Leu|Glu|Gly|Thr|Glu|Ala|Ser|Leu|
| | |500| | | |505| | | |510| | | | | |
|Ser|Cys|Val|Ala|His|Gly|Val|Pro|Pro|Pro|Asp|Val|Ile|Cys|Val|Arg|
| |515| | | |520| | | |525| | | | | | |
|Ser|Gly|Glu|Leu|Gly|Ala|Val|Ile|Glu|Gly|Leu|Leu|Arg|Val|Ala|Arg|
|530| | | |535| | | |540| | | | | | | |
|Glu|His|Ala|Gly|Thr|Tyr|Arg|Cys|Glu|Ala|Thr|Asn|Pro|Arg|Gly|Ser|
|545| | | |550| | | |555| | | | | | |560|
|Ala|Ala|Lys|Asn|Val|Ala|Val|Thr|Val|Glu|Tyr|Gly|Pro|Arg|Phe|Glu|
| | | |565| | | |570| | | | |575| | | |
|Glu|Pro|Ser|Cys|Pro|Ser|Asn|Trp|Thr|Trp|Val|Glu|Gly|Ser|Gly|Arg|
| | |580| | | |585| | | |590| | | | | |
|Leu|Phe|Ser|Cys|Glu|Val|Asp|Gly|Lys|Pro|Gln|Pro|Ser|Val|Lys|Cys|
| |595| | | |600| | | |605| | | | | | |
|Val|Gly|Ser|Gly|Gly|Thr|Thr|Glu|Gly|Val|Leu|Leu|Pro|Leu|Ala|Pro|
|610| | | |615| | | |620| | | | | | | |
|Pro|Asp|Pro|Ser|Pro|Arg|Ala|Pro|Arg|Ile|Pro|Arg|Val|Leu|Ala|Pro|
|625| | | |630| | | |635| | | | | | |640|
|Gly|Ile|Tyr|Val|Cys|Asn|Ala|Thr|Asn|Arg|His|Gly|Ser|Val|Ala|Lys|
| | | |645| | | |650| | | | |655| | | |
|Thr|Val|Val|Val|Ser|Ala|Glu|Ser|Pro|Pro|Glu|Met|Asp|Glu|Ser|Thr|
| | |660| | | |665| | | |670| | | | | |
|Cys|Pro|Ser|His|Gln|Thr|Trp|Leu|Glu|Gly|Ala|Glu|Ala|Ser|Ala|Leu|
| |675| | | |680| | | |685| | | | | | |
|Ala|Cys|Ala|Ala|Arg|Gly|Arg|Pro|Ser|Pro|Gly|Val|Arg|Cys|Ser|Arg|
| |690| | | |695| | | |700| | | | | | |
|Glu|Gly|Ile|Pro|Trp|Pro|Glu|Gln|Gln|Arg|Val|Ser|Arg|Glu|Asp|Ala|
|705| | | |710| | | |715| | | | | | |720|
|Gly|Thr|Tyr|His|Cys|Val|Ala|Thr|Asn|Ala|His|Gly|Thr|Asp|Ser|Arg|

|       | 725 |       |       |       |       |       |       | 730 |       |       |       |       |       | 735 |       |
|-------|-----|-------|-------|-------|-------|-------|-------|-----|-------|-------|-------|-------|-------|-----|-------|
| Thr   | Val | Thr   | Val   | Gly   | Val   | Glu   | Tyr   | Arg | Pro   | Val   | Val   | Ala   | Glu   | Leu | Ala   |
|       |     |       | 740   |       |       |       |       | 745 |       |       |       |       | 750   |     |       |
| Ala   | Ser | Pro   | Pro   | Gly   | Gly   | Val   | Arg   | Pro | Gly   | Gly   | Asn   | Phe   | Thr   | Leu | Thr   |
|       |     | 755   |       |       |       |       | 760   |     |       |       |       | 765   |       |     |       |
| Cys   | Arg | Ala   | Glu   | Ala   | Trp   | Pro   | Pro   | Ala | Gln   | Ile   | Ser   | Trp   | Arg   | Ala | Pro   |
| 770   |     |       |       |       |       | 775   |       |     |       |       | 780   |       |       |     |       |
| Pro   | Arg | Ala   | Leu   | Asn   | Ile   | Gly   | Leu   | Ser | Ser   | Asn   | Asn   | Ser   | Thr   | Leu | Ser   |
| 785   |     |       |       |       | 790   |       |       |     |       | 795   |       |       |       |     | 800   |
| Val   | Ala | Gly   | Ala   | Met   | Gly   | Ser   | His   | Gly | Gly   | Glu   | Tyr   | Glu   | Cys   | Ala | Arg   |
|       |     |       |       | 805   |       |       |       |     | 810   |       |       |       | 815   |     |       |
| Thr   | Asn | Ala   | His   | Gly   | Arg   | His   | Ala   | Arg | Arg   | Ile   | Thr   | Val   | Arg   | Val | Ala   |
|       |     |       | 820   |       |       |       |       | 825 |       |       |       |       | 830   |     |       |
| Gly   | Pro | Trp   | Leu   | Trp   | Val   | Ala   | Val   | Gly | Gly   | Ala   | Ala   | Gly   | Gly   | Ala | Ala   |
|       |     | 835   |       |       |       |       | 840   |     |       |       |       | 845   |       |     |       |
| Leu   | Leu | Ala   | Ala   | Gly   | Ala   | Gly   | Leu   | Ala | Phe   | Tyr   | Val   | Gln   | Ser   | Thr | Ala   |
|       | 850 |       |       |       |       | 855   |       |     |       |       | 860   |       |       |     |       |
| Cys   | Lys | Lys   | Gly   | Glu   | Tyr   | Asn   | Val   | Gln | Glu   | Ala   | Glu   | Ser   | Ser   | Gly | Glu   |
| 865   |     |       |       |       | 870   |       |       |     |       | 875   |       |       |       |     | 880   |
| Ala   | Val | Cys   | Leu   | Asn   | Gly   | Ala   | Gly   | Gly | Gly   | Ala   | Gly   | Gly   | Ala   | Ala | Gly   |
|       |     |       |       | 885   |       |       |       |     | 890   |       |       |       |       | 895 |       |
| Ala   | Glu | Gly   | Gly   | Pro   | Glu   | Ala   | Ala   | Gly | Gly   | Ala   | Ala   | Ala   | Glu   | Ser | Pro   | Ala   |
|       |     |       | 900   |       |       |       |       | 905 |       |       |       |       |       | 910 |       |
| Glu   | Gly | Glu   | Val   | Phe   | Ala   | Ile   | Gln   | Leu | Thr   | Ser   | Ala   |       |       |     |       |
|       |     |       | 915   |       |       |       | 920   |     |       |       |       |       |       |     |       |

( 2 ) INFORMATION FOR SEQ ID NO:29:

( i ) SEQUENCE CHARACTERISTICS:
        ( A ) LENGTH: 65 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:29:

GTACTTACAG GATCCGCGGT CTCGCAGGAG CCCTTCTGGG CGGACCTACA GCCTGCGTGG     60

CGTTC     65

( 2 ) INFORMATION FOR SEQ ID NO:30:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:30:

ATTTCTCTCG AGGATGGTCA CGTTCTCCCG G     31

( 2 ) INFORMATION FOR SEQ ID NO:31:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: cDNA -continued (xi) SEQUENCE DESCRIPTION: SEQ ID NO:31:

ATTTCTGGAT CCTACAGCTT CCCGGCACCA CTC　　33

(2) INFORMATION FOR SEQ ID NO:32:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:32:

ATTTCTCTCG AGTTCCACGC CCACAGTGAC GG　　32

ANTI-ICAM-4 ANTIBODIES AND HYBRIDOMAS

This application is a continuation-in-part of U.S. patent application Ser. No. 08/245,295, filed May 18, 1994 now U.S. Pat. No. 5,700,658, which in turn is a continuation-in-part of U.S. patent application Ser. No. 08/102,852, filed Aug. 5, 1993, now abandoned as a continuation-in-part of U.S. patent application Ser. No. 08/009,266, filed Jan. 22, 1993, now abandoned as a continuation-in-part of U.S. patent application Ser. No. 07/894,061, filed Jun. 5, 1992, now abandoned as a continuation-in-part of U.S. patent application Ser. No. 07/889,724, filed May 26, 1992, now abandoned as a continuation-in-part of U.S. patent application Ser. No. 07/827,689, filed Jan. 27, 1992, now abandoned.

FIELD OF THE INVENTION

The present invention relates generally to cellular adhesion molecules and more particularly to the cloning and expression of DNA encoding a heretofore unknown polypeptide designated "ICAM-4" which possesses structural relatedness to the intercellular adhesion molecules ICAM-1, ICAM-2, and ICAM-R.

BACKGROUND OF THE INVENTION

Research spanning the last decade has significantly elucidated the molecular events attending cell-cell interactions in the body, especially those events involved in the movement and activation of cells in the immune system, and more recently, those involved in development and normal physiological function of cells in the nervous system. See generally, Springer, *Nature*, 346: 425–434 (1990) regarding cells of the immune system, and Yoshihara, et al. *Neurosci. Res.* 10:83–105 (1991) and Sonderegger and Rathjen, *J. Cell Biol.* 119:1387–1394 (1992) regarding cells of the nervous system. Cell surface proteins, and especially the so-called Cellular Adhesion Molecules ("CAMs") have correspondingly been the subject of pharmaceutical research and development having as its goal intervention in the processes of leukocyte extravasation to sites of inflammation and leukocyte movement to distinct target tissues, as well as neuronal differentiation and formation of complex neuronal circuitry. The isolation and characterization of cellular adhesion molecules, the cloning and expression of DNA sequences encoding such molecules, and the development of therapeutic and diagnostic agents relevant to inflammatory processes and development and function of the nervous system have also been the subject of numerous U.S. and foreign applications for Letters Patent. See Edwards, *Current Opinion in Therapeutic Patents,* 1(11): 1617–1630 (1991) and particularly the published "patent literature references" cited therein.

Of fundamental interest to the background of the present invention are the prior identification and characterization of certain mediators of cell adhesion events, the "leukointegrins," LFA-1, MAC-1 and gp 150.95 (referred to in WHO nomenclature as CD18/CD11a, CD18/CD11b, and CD18/CD11c, respectively) which form a subfamily of heterodimeric "integrin" cell surface proteins present on B lymphocytes, T lymphocytes, monocytes and granulocytes. See, e.g., Table 1 of Springer, supra, at page 429. Also of interest are other single chain adhesion molecules (CAMs) that have been implicated in leukocyte activation, adhesion, motility and the like, which are events attendant to the inflammatory process. For example, it is presently believed that prior to the leukocyte extravasation which characterizes inflammatory processes, activation of integrins constitutively expressed on leukocytes occurs and is followed by a tight ligand/receptor interaction between the integrins (e.g., LFA-1) and one or both of two distinct intercellular adhesion molecules (ICAMs) designated ICAM-1 and ICAM-2 which are expressed on blood vessel endothelial cell surfaces and on other leukocytes.

Like the other CAMs characterized to date, [e.g., vascular adhesion molecule (VCAM-1) as described in PCT WO 90/13300 published Nov. 15, 1990; and platelet endothelial cell adhesion molecule (PECAM-1) as described in Newman et al., *Science,* 247: 1219–1222 (1990) and PCT WO 91/10683 published Jul. 25, 1991], ICAM-1 and ICAM-2 are structurally homologous to other members of the immunoglobulin gene superfamily in that the extracellular portion of each is comprised of a series of domains sharing a similar carboxy terminal motif. A "typical" immunoglobulin-like domain contains a loop structure usually anchored by a disulfide bond between two cysteines at the extremity of each loop. ICAM-1 includes five immunoglobulin-like domains; ICAM-2, which differs from ICAM-1 in terms of cell distribution, includes two such domains; PECAM-1 includes six; VCAM includes six or seven, depending on splice variations, and so on. Moreover, CAMs typically include a hydrophobic "transmembrane" region believed to participate in orientation of the molecule at the cell surface and a carboxy terminal "cytoplasmic" region. Graphic models of the operative disposition of CAMs generally show the molecule anchored in the cell membrane at the transmembrane region with the cytoplasmic "tail" extending into the cell cytoplasm and one or more immunoglobulin-like loops extending outward from the cell surface.

A number of neuronal cells express surface receptors with extracellular Ig-like domains, structurally similarity to the ICAMs. See for example, Yoshihara, et al., supra. In addition to Ig-like domains, many adhesion molecules of the nervous system also contain tandemly repeated fibronectin-like sequences in the extracellular domain.

A variety of therapeutic uses has been projected for intercellular adhesion molecules, including uses premised on the ability of ICAM-1 to bind human rhinovirus. European Patent Application 468 257 A published Jan. 29, 1992, for example, addresses the development of multimeric configurations and forms of ICAM-1 (including full length and truncated molecular forms) proposed to have enhanced ligand/receptor binding activity, especially in binding to viruses, lymphocyte associated antigens and pathogens such as *Plasmodium falciparum.*

In a like manner, a variety of uses has been projected for proteins immunologically related to intercellular adhesion molecules. WO91/16928, published Nov. 14, 1991, for example, addresses humanized chimeric anti-ICAM-1 antibodies and their use in treatment of specific and non-specific inflammation, viral infection and asthma. Anti-ICAM-1 antibodies and fragments thereof are described as useful in treatment of endotoxic shock in WO92/04034, published Mar. 19, 1992. Inhibition of ICAM-1 dependent inflammatory responses with anti-ICAM-1 anti-idiotypic antibodies and antibody fragments is addressed in WO92/06119, published Apr. 16, 1992.

Despite the fundamental insights into cell adhesion phenomena which have been gained by the identification and characterization of intercellular adhesion proteins such as ICAM-1 and lymphocyte interactive integrins such as LFA-1, the picture is far from complete. It is generally believed that numerous other proteins are involved in inflammatory processes and in targeted lymphocyte movement throughout the body. For example, U.S. patent application Ser. Nos. 07/827,689, 07/889,724, 07/894,061 and 08/009,266 and corresponding published PCT Application WO 93/14776 (published Aug. 5, 1993) disclose the cloning and expression of an ICAM-Related protein, ICAM-R. The disclosures of these applications are specifically incorporated by reference herein and the DNA and amino acid sequences of ICAM-R are set out in SEQ ID NO. 4 herein. This new ligand has been found to be expressed on human lymphocytes, monocytes and granulocytes.

Of particular interest to the present application, still another ICAM-like surface molecule was identified which has a tissue specific expression unlike that of any known ICAM molecule. Mori, et al., [*Proc. Natl. Acad. Sci. (USA)* 84:3921–3925 (1987)] reported identification of a telencephalon-specific antigen in rabbit brain, specifically immunoreactive with monoclonal antibody 271A6. This surface antigen was named telencephalin. Imamura, et al., [*Neurosci. Letts.* 119:118–121 (1990)], using a polyclonal antibody to assess localized expression, asserted that expression of telencephalin in visual cortex of cats showed variation in layers of the tissue, and also reported telencephalin expression was variable as a function of development. Oka, et al., [*Neuroscience* 35:93–103 (1990)] subsequently reported isolation of telencephalin using monoclonal antibody 271A6. The publication reports a molecular weight for the surface molecule of about 500 kD and that the molecule was composed of four subunits, each with a native molecular weight of 130 kD and approximately 100 kD following N-glycanase treatment. Yoshihiro, et al., [Neuroscience, Research Supplement 18, p. S83 (1994)], reported the cDNA and amino acid sequences for rabbit telencephalin at the 17th Annual Meeting of the Japan Neuroscience Society in Nagoya, Japan, Dec. 7–9, 1993, and the 23rd Annual Meeting of the Society for Neuroscience in Washington, D.C., Nov. 9, 1993 [Society for Neuroscience Abstracts 19 (1–3) p. 646 (1993)]. The deduced amino acid sequence reported suggested that the 130 kD telencephalon is an integral membrane protein with nine extracellular immunoglobulin (Ig)-like domains. The distal eight of these domains showed homology to other ICAM Ig-like domains. This same information was reported by Yoshihara, et al., in *Neuron* 12:543–553 (1994).

There thus continues to be a need in the art for the discovery of additional proteins participating in human cell-cell interactions and especially a need for information serving to specifically identify and characterize such proteins in terms of their amino acid sequence. Moreover, to the extent that such molecules might form the basis for the development of therapeutic and diagnostic agents, it is essential that the DNA encoding them be elucidated. Such seminal information would inter alia, provide for the large scale production of the proteins, allow for the identification of cells naturally producing them, and permit the preparation of antibody substances or other novel binding proteins specifically reactive therewith and/or inhibitory of ligand/receptor binding reactions in which they are involved.

BRIEF SUMMARY OF THE INVENTION

In one of its aspects, the present invention provides purified and isolated polynucleotides (e.g., DNA sequences, RNA transcripts and anti-sense oligonucleotides thereof) encoding a novel polypeptide, "ICAM-4," as well as polypeptide variants (including fragments and deletion, substitution, and addition analogs) thereof which display one or more ligand/receptor binding biological activities and/or immunological properties specific to ICAM-4. ICAM-4-specific ligand/receptor binding biological activities encompass interactions of both the ICAM-4 extracellular and cytoplasmic domains with other molecules (e.g., in processes of cell-cell adhesion and/or signal transduction). Preferred DNA sequences of the invention include genomic and cDNA sequences as well as wholly or partially chemically synthesized DNA sequences. A presently preferred polynucleotide is set out in SEQ ID NO: 1 and encodes rat species ICAM-4. Biological replicas (i.e., copies of isolated DNA sequences made in vivo or in vitro) of DNA sequences of the invention are contemplated. Also provided are autonomously replicating recombinant constructions such as plasmid and viral DNA vectors incorporating ICAM-4 sequences and especially vectors wherein DNA encoding ICAM-4 or an ICAM-4 variant is operatively linked to an endogenous or exogenous expression control DNA sequence.

According to another aspect of the invention, host cells, especially unicellular host cells such as procaryotic and eucaryotic cells, are stably transformed with DNA sequences of the invention in a manner allowing the desired polypeptides to be expressed therein. Host cells expressing such ICAM-4 and ICAM-4 variant products can serve a variety of useful purposes. To the extent that the expressed products are "displayed" on host cell surfaces, the cells may constitute a valuable immunogen for the development of antibody substances specifically immunoreactive with ICAM-4 and ICAM-4 variants. Host cells of the invention are conspicuously useful in methods for the large scale production of ICAM-4 and ICAM-4 variants wherein the cells are grown in a suitable culture medium and the desired polypeptide products are isolated from the cells or from the medium in which the cells are grown.

Novel ICAM-4 of the invention may be obtained as isolates from natural cell sources, but, along with ICAM-4 variant products, are preferably produced by recombinant procedures involving host cells of the invention. A presently preferred amino acid sequence for an ICAM-4 polypeptide is set out in SEQ ID NO: 2. The products may be obtained in fully or partially glycosylated, partially or wholly de-glycosylated, or non-glycosylated forms, depending on the host cell selected for recombinant production and/or post-isolation processing. ICAM-4 variants of the invention may comprise water soluble or insoluble monomeric, multimeric or cyclic ICAM-4 fragments which include all or part of one or more of the domain regions specified above and having a biological or immunological property of ICAM-4 including, e.g., the ability to bind to a binding partner of ICAM-4 and/or inhibit binding of ICAM-4 to a natural binding partner. ICAM-4 variants of the invention may also comprise polypeptide analogs wherein one or more of the specified amino acids is deleted or replaced: (1) without loss, and preferably with enhancement, of one or more biological activities or immunological characteristics specific for ICAM-4; or (2) with specific disablement of a particular ligand/receptor binding function. Analog polypeptides including additional amino acid (e.g., lysine or cysteine) residues that facilitate multimer formation are contemplated.

Also comprehended by the present invention are antibody substances (e.g., monoclonal and polyclonal antibodies, antibody fragments, single chain antibodies, chimeric antibodies, CDR-grafted antibodies and the like) and other binding proteins (e.g., polypeptides and peptides) which are specific (i.e., non-reactive with the ICAM-1, ICAM-2, and ICAM-R intercellular adhesion molecules to which ICAM-4 is structurally related) for ICAM-4 or ICAM-4 variants. Antibody substances can be developed using isolated natural or recombinant ICAM-4 or ICAM-4 variants or cells expressing such products on their surfaces. Binding proteins of the invention are additionally useful for characterization of binding site structure(s) (e.g., epitopes and/or sensitivity of binding properties to modifications in ICAM-4 amino acid sequence).

Binding proteins are useful, in turn, in compositions for immunization as well as for purifying polypeptides of the invention and identifying cells displaying the polypeptides on their surfaces. They are also manifestly useful in modulating (i.e., blocking, inhibiting or stimulating) ligand/receptor binding biological activities involving ICAM-4, especially those ICAM-4 effector functions involved in specific and non-specific immune system responses. Anti-idiotypic antibodies specific for anti-ICAM-4 antibody substances and uses of such anti-idiotypic antibody substances in modulating immune responses are also contemplated. Assays for the detection and quantification of ICAM-4 on cell surfaces and in body fluids, such as serum or cerebrospinal fluid, may involve, for example, a single antibody substance or multiple antibody substances in a "sandwich" assay format.

The scientific value of the information contributed through the disclosures of DNA and amino acid sequences of the present invention is manifest. As one series of examples, knowledge of the sequence of a cDNA for ICAM-4 makes possible the isolation by DNA/DNA hybridization of genomic DNA sequences encoding ICAM-4 and specifying ICAM-4 expression control regulatory sequences such as promoters, operators and the like. DNA/DNA hybridization procedures carried out with DNA sequences of the invention and under stringent conditions are likewise expected to allow the isolation of DNAs encoding allelic variants of ICAM-4, other structurally related proteins sharing one or more of the biological and/or immunological properties specific to ICAM-4, and proteins homologous to ICAM-4 from other species. DNAs of the invention are useful in DNA/RNA hybridization assays to detect the capacity of cells to synthesize ICAM-4. Also made available by the invention are anti-sense polynucleotides relevant to regulating expression of ICAM-4 by those cells which ordinarily express the same. As another series of examples, knowledge of the DNA and amino acid sequences of ICAM-4 makes possible the generation by recombinant means of ICAM-4 variants such as hybrid fusion proteins (sometimes referred to as "immunoadhesions") characterized by the presence of ICAM-4 protein sequences and immunoglobulin heavy chain constant regions and/or hinge regions. See, Capon et al., *Nature*, 337: 525–531 (1989); Ashkenazi et al., *P.N.A.S.* (*USA*), 88: 10535–10539 (1991); and PCT WO 89/02922, published Apr. 6, 1989. ICAM-4 variant fusion proteins may also include, for example, selected extracellular domains of ICAM-4 and portions of other cell adhesion molecules.

The DNA and amino acid sequence information provided by the present invention also makes possible the systematic analysis of the structure and function of ICAM-4 and definition of those molecules with which it will interact on extracellular and intracellular levels. The idiotypes of anti-ICAM-4 monoclonal antibodies of the invention are representative of such molecules and may mimic natural binding proteins (peptides and polypeptides) through which ICAM-4 intercellular and intracellular activities are modulated or by which ICAM-4 modulates intercellular and intracellular events. Alternately, they may represent new classes of modulators of ICAM-4 activities. Anti-idiotypic antibodies, in turn, may represent new classes of biologically active ICAM-4 equivalents. In vitro assays for identifying antibodies or other compounds that modulate the activity of ICAM-4 may involve, for example, immobilizing ICAM-4 or a natural ligand to which ICAM-4 binds, detectably labelling the nonimmobilized binding partner, incubating the binding partners together and determining the effect of a test compound on the amount of label bound wherein a reduction in the label bound in the presence of the test compound compared to the amount of label bound in the absence of the test compound indicates that the test agent is an inhibitor of ICAM-4 binding. The DNA sequence information provided by the present invention also makes possible the development, by homologous recombination or "knockout" strategies [see, e.g., Kapecchi, *Science*, 244: 1288–1292 (1989)], of rodents that fail to express a functional ICAM-4 protein or that express a variant ICAM-4 protein. Such rodents are useful as models for studying the activities of ICAM-4 and ICAM-4 modulators in vivo.

DETAILED DESCRIPTION OF THE INVENTION

The disclosures of parent U.S. patent application Ser. No. 08/102,852, filed Aug. 5, 1993, are specifically incorporated by reference. The examples of that application address, inter alia: design and construction of oligonucleotide probes for PCR amplification of ICAM related DNAs; use of the probes to amplify a human genomic fragment homologous to, but distinct from DNAs encoding ICAM-1 and ICAM-2; screening of cDNA libraries with the genomic fragment to isolate additional ICAM-R coding sequences; screening of cDNA libraries to isolate a full length human cDNA sequence encoding ICAM-R; characterization of DNA and amino acid sequence information for ICAM-R, especially as related to ICAM-1 and ICAM-2; development of mammalian host cells expressing ICAM-R; assessment of indications of ICAM-R participation in adhesion events involving CD18-dependent and CD18-independent pathways; inhibition of cell adhesion to ICAM-R by ICAM-R-derived peptides; expression of variants of ICAM-R; preparation and characterization of anti-ICAM-R antibodies and fragments thereof; mapping of ICAM-R epitopes recognized by anti-ICAM-R monoclonal antibodies; assessment of the distribution and biochemical characterization of ICAM-R and RNA encoding the same; assessment of ICAM-R in homotypic cell-cell adhesion and immune cell activation/proliferation; characterization of ICAM-R monoclonal antibodies; and assessment of differential phosphorylation and cytoskeletal associations of the cytoplasmic domain of ICAM-R. Also disclosed was the identification of a rodent ICAM-encoding DNA that, at the time, appeared to be the rat homolog of human ICAM-R, and the use of this DNA to construct and express DNAs encoding glutathione-S-transferase fusion proteins. The detailed description of how this rodent DNA was identified can be found in the parent application (U.S. Ser. No. 08/102,852) in Example 6, and is reproduced herein as Example 1. As more of the rodent ICAM-coding sequence was identified, it became apparent that the rodent ICAM DNA did not encode a rat species homolog of human ICAM-R, but, in fact, encoded a novel ICAM polypeptide, herein named ICAM-4. In order to appreciate the events which led to the identification of ICAM-4, a chronology is provided which is followed by a detailed description of the invention.

A first rodent genomic ICAM-4 sequence was identified which encoded a region homologous to domain 2 (herein SEQ ID NO: 3, and SEQ ID NO: 23 of U.S. Ser. No. 08/102,852) of human ICAM-R (herein as SEQ ID NO: 4). A second, overlapping genomic DNA (herein SEQ ID NO: 5, and SEQ ID NO: 26 of U.S. Ser. No. 08/102,852) was also identified which encoded both the domain 2 region of SEQ ID NO: 3, and sequences for ICAM-1. Using SEQ ID NO: 3 as a probe, a rodent spleen cDNA (herein SEQ ID NO: 6, and SEQ ID NO: 25 in U.S. Ser. No. 08/102,852) was identified which encoded domains 2 through 5 as well as a fifth domain not previously observed as an ICAM domain. At this time, these newly identified rodent DNAs appeared to encode a rodent homolog of human ICAM-R, however alignment of 3' regions of these DNAs with other ICAMs proved difficult.

The subsequent isolation of a 1 kb cDNA clone from a rat spleen library, and amplification of an RT-PCR fragment indicated that a portion of both the cDNA and genomic clones had not been sequenced. Another RT-PCR amplification product (SEQ ID NO: 7) confirmed this omission. It was determined that a fragment of 177 bp was excised from the genomic and cDNA clones by EcoRI digestion of the clones to isolate these sequences from λ phage for DNA sequencing studies. Reanalysis of SEQ ID NOs: 5 and 6 in light of these other sequences permitted identification of more accurate and complete sequences for the originally isolated genomic and cDNA clones, presented in corrected form herein as SEQ ID NOs: 8 and 9.

In order to identify a complete coding sequence for ICAM-4, a rat brain cDNA (SEQ ID NO: 10) was isolated, and 5' end sequence determined by 5' rapid amplification of cDNA ends (5' RACE), the amplification product set forth in SEQ ID NO: 11. Combining information from the RT-PCR clone (SEQ ID NO: 7), the brain cDNA (SEQ ID NO: 10) and the RACE amplification product (SEQ ID NO: 11) permitted identification of the complete coding sequence for ICAM-4 (SEQ ID NO: 1).

The present invention is thus illustrated by the following examples. More particularly, Example 1 addresses cloning of a partial rodent ICAM-4 DNA. Example 2 describes Northern blot analysis of rodent ICAM-4 transcription. Example 3 describes isolation of a full length rodent ICAM-4 cDNA. Example 4 relates the in situ hybridization of rodent ICAM-4 in brain tissue. Example 5 addresses generation of ICAM-4 fusion proteins in prokaryotes. Example 6 describes production of monoclonal antibodies specific for rat ICAM-4/GST fusion proteins. Example 7 describes expression of soluble rat ICAM-4 proteins in a baculovirus expression system. Example 8 addresses production of monoclonal antibodies specific for rat ICAM-4 expressed in a baculovirus system. Example 9 describes immunocytochemical analysis of rat ICAM-4 expression. Example 10 relates cloning of a human genomic ICAM-4-encoding DNA. Example 11 addresses cloning of a human ICAM-4-encoding cDNA. Example 12 describes Northern analysis of human ICAM-4 expression. Example 13 describes generation of human ICAM-4/GST fusion proteins. Example 14 addresses production of monoclonal antibodies immunospecific for human ICAM-4.

EXAMPLE 1

Cloning of Rat ICAM-Related DNA

A. Isolation of a Rat Genomic ICAM-Related Domain 2 DNA

A rat genomic library constructed in λ EMBL3 was screened a with [$^{32}$P]-labeled probe generated by PCR from DNA encoding human ICAM-3 domain 2 The sequence of the probe is set forth in SEQ ID NO: 12. Library plaques were transferred to Hybond N+ nylon membranes (Amersham, Arlington Heights, Ill.). Screening of all cDNA and genomic libraries was performed according to standard protocols. Prehybridization and hybridizations were carried out in a solution of 40–50% formamide, 5× Denhardt's, 5× SSPE and 1.0% SDS at 42° C. Probes ([$^{32}$P]-labeled) were added at a concentration of $10^5$–$10^6$ cpm/ml of hybridization solution. Following 16–18 hours of hybridization, nylon membranes were washed extensively at room temperature in 2× SSPE with 0.1% SDS and subsequently exposed to X-ray film at −80° C. overnight. Positive plaques were subjected to one or more rounds of hybridization to obtain clonal phage. DNA prepared from lysate of the positive clones was subcloned into pBS+ and sequenced.

A first genomic clone encoding a rat ICAM-related domain 2 was identified that was determined to be homologous to domain 2 regions in other ICAM family members (see for example, Table 1 of U.S. patent application Ser. No. 08/102,852), yet was distinct from the previously reported nucleotide sequences for rat ICAM-1 [Kita, et al., *Biochem. Biophys. Acta* 1131:108–110 (1992)] or mouse ICAM-2 [Xu, et al., *J. Immunol.* 149:2560–2565 (1992)]. The nucleic acid and deduced amino acid sequences for this clone were disclosed in the co-pending parents to the present application as purportedly variant forms of rat ICAM-R and were set forth as SEQ ID NOs: 23 and 24, respectively, in U.S. Ser. No. 08/102,852. Herein, these same sequences are set out in SEQ ID NOs: 3 and 13, respectively.

A second, overlapping clone was also identified with the same probes and was determined to contain the ICAM domain 2 sequence of SEQ ID NO: 3 and 5' DNA encoding at least part of rat ICAM-1. The nucleic acid sequence for this clone was set forth in the co-pending parent to the present application as SEQ ID NO: 26 and is set forth herein as SEQ ID NO: 5. This second clone indicated that the ICAM-related gene fragment of the first clone and the gene encoding rat ICAM-1 are located on the same rat chromosome within 5 kb of each other.

B. Isolation of Rat ICAM-Related cDNA

In order to identify a more complete protein coding sequence for the ICAM-related polypeptide, [$^{32}$P]-labeled DNA encoding the domain 2 sequence from the rat genomic clone identified in Section A (SEQ ID NO: 3), supra, was used to screen a number of cDNA libraries from various rat and mouse cell types, including rat macrophage (Clontech, Palo Alto, Calif.), peripheral blood lymphocyte (PBL) (Clontech), T cell (constructed in-house), and spleen (Clontech), and mouse PBL (Clontech), T cell (constructed in-house), and B cell (constructed in-house).

A single clone was identified in a rat spleen cDNA library (Clontech) which contained five Ig-like domains, four of which were homologous to domains 2 through 5 in both ICAM-1 and ICAM-R. Moreover, this clone included 3' DNA encoding an apparent fifth Ig-like domain which had not been previously identified in any other ICAM polypeptide. In addition, the clone contained an unusual 3' sequence subsequently determined to be a partial intron (discussed infra) located between domains 4 and 5, suggesting that the clone was the product of an immature or aberrantly spliced transcript. The presence of the unique domain and the determination that the 3' region did not properly align with other known ICAMs suggested that the ICAM-related DNA potentially encoded a novel rat ICAM polypeptide. The nucleic acid sequence for this clone was set forth in the parent to the present application as SEQ ID NO: 25; herein the nucleic acid sequence for this spleen cDNA clone is set forth in SEQ ID NO: 6.

C. Re-analysis of Rat cDNA and Genomic DNAs

Subsequent to the Aug. 5, 1993 filing of U.S. patent application Ser. No. 08/102,852, it was determined that the partial rat spleen cDNA clone (SEQ ID NO: 25 in the parent and SEQ ID NO: 6 herein) and the rat liver genomic clone (SEQ ID NO: 26 of the parent and SEQ ID NO: 5 herein) were missing an internal 177 bp EcoRI fragment that was part of each of these clones but lost in a subcloning step when the library inserts were removed from the λ vector with EcoRI digestion and ligated into a sequencing vector. The observation that the cDNA and genomic clones might be missing a coding fragment became apparent upon alignment of the rat genomic and cDNA sequences with various RT-PCR amplification products, including SEQ ID NO: 7, which revealed a gap in the rat sequence.

Subsequent isolation and sequence alignment of a cDNA from a spleen library using the spleen cDNA clone (SEQ ID NO: 6) as a probe provided a first indication that a portion of the spleen cDNA and genomic clones were not sequenced. Further confirmation of this idea became apparent upon amplification of an RT-PCR fragment, spanning domains 3 through 5, using a 5' primer (RRD3 5'Xho, containing a 5' XhoI restriction site to facilitate cloning) set out in SEQ ID NO: 14, and a 3' primer (RRD5 3'Hind, containing a HindIII site to facilitate cloning) set out in SEQ ID NO: 15.

GAACTCGAGGCCATGCCTCCACTTTCC (SEQ ID NO: 14)

CCATAAGCTTTATTCCACCGTGACAGCCAC (SEQ ID NO: 15)

Alignment of these two DNAs clearly revealed that the cDNA and genomic clones had lost a fragment prior to sequencing; this idea was further supported following sequencing of the RT-PCR DNA discussed infra. It was concluded that restriction digestion with EcoRI to remove the cDNA and genomic fragments prior to sequencing resulted in the excision of a 177 bp fragment that was not detected visually in the agarose gel separation of the clones from the λ phage sequences. Subsequent sequence analysis confirmed the location of two EcoRI sites flanking a 177 bp fragment in both of the original clones.

The 177 bp EcoRI fragment is situated between nucleotides 719 and 896 in the rat partial cDNA clone as set out in SEQ ID NO: 9 and between nucleotides 2812 and 2989 in the partial genomic clone as set out in SEQ ID NO: 8.

D. DNA Isolated by RT-PCR Clone

RT-PCR was utilized to generate more complete sequence information for the rat ICAM-related gene. Sequence information from the genomic clone (SEQ ID NO: 3) was used to design sense primers complementary to a region 5' of the protein coding region, as determined from the cDNA clone, and antisense primers designed complementary to coding sequences and regions 3' to the coding sequence in the cDNA clone (SEQ ID NO: 6).

Template cDNA for PCR reactions was prepared as follows. Approximately 2 μg of poly A$^+$ RNA isolated from rat spleen cells was denatured by heating at 65° C. in a 10 μl volume. Following denaturation, 0.1 μl RNasin (Invitrogen, San Diego, Calif.), 5 μl 5× RTase Buffer (BRL, Bethesda, Md.), 2 μl random hexamer (pd(N)6 at 100 μg/ml) (Pharmacia, Piscataway, N.J.), 6 μl dNTPs (2 mM each) and 2 μl AMV RTase (BRL) were added and the reaction was incubated at 42° C. for 60–90 min. Reactions were stored at −20° C. until needed.

An initial series of experiments was conducted to identify oligonucleotides primer pairs that produced an amplification product in PCR reactions using rat spleen cDNA as the template. Various 5' sense primers were paired in PCR with a 3' primer which was designed to be complementary to an internal, coding sequence; the 3' primer was designated RRD2 3-1 and is set forth in SEQ ID NO: 16.

AACGTGCGGAGCTGTCTG (SEQ ID NO: 16)

(In the ultimately isolated RT-PCR product, SEQ ID NO: 7, infra, primer RRD2 3-1 corresponded to nucleotides 719 through 736.) Similarly, various 3' antisense primers were paired with a 5' primer designed complementary to another internal, coding sequence; the 5' primer in these reactions was designated RGen3900S and is set forth in SEQ ID NO: 17.

ACGGAATTCGAAGCCATCAACGCCAGG (SEQ ID NO: 17)

(In SEQ ID NO: 7, infra, primer RGen3900S corresponded to nucleotides 1719 through 1736.) Based on the size of the amplification products and the ability of these products to hybridize with the partial cDNA clone, one pair of primers was determined to be most efficient and was used in subsequent PCR amplifications. The 5' primer was designated RGen780S (SEQ ID NO: 18) and the 3' primer was designated RGen4550AS (SEQ ID NO: 19).

CATGAATTCCGAATCTTGAGTGGGATG (SEQ ID NO: 18)

ATAGAATTCCTCGGGACACCTGTAGCC (SEQ ID NO: 19)

(In SEQ ID NO: 7, infra, primer RGen780S corresponded to nucleotides 1 through 18, and primer RGen4550AS corresponded to nucleotides 2197 through 2214.)

This primer pair was used in PCR under a variety of conditions to optimize amplification. A total of 15 different PCR buffers that varied in pH and Mg$^{++}$ concentration were used at two different annealing temperatures, and a sample of the product from each reaction was separated on a 1% agarose gel. Because no amplification product could be detected by visual inspection of the ethidium bromide stained gel from any of the reaction conditions, more sensitive Southern hybridization was employed to detect the PCR products.

Aliquots of the amplified DNA were separated by electrophoresis, transferred to a Hybond N+ nylon membrane using conventional Southern blotting wicking techniques, and hybridized with the entire rat cDNA which was [$^{32}$P]-labeled. Hybridization conditions were essentially as described for the library screening procedure in Section A, supra. Autoradiography indicated that a small amount of DNA of approximately 2.2 kb had been generated in two of the reactions, and the remainder of the amplification product from the two reactions was separated on an agarose gel. The 2.2 kb region was eluted from the gel, even though no band was evident upon visual inspection, and used as a template in another PCR reaction using the same primers (SEQ ID NOs: 18 and 19), Tris-HCl buffer, pH 8.0, containing 1 mM Mg$^{++}$, and 55° C. annealing temperature. The amplification product from the secondary PCR was visible in the gel and was eluted and cloned into a pBS$^+$ plasmid (Stratagene, La Jolla, Calif.) for sequence analysis.

The resulting RT-PCR clone was determined to contain 2214 bp as set forth in SEQ ID NO: 7. The clone encoded domains 2 through 6 found in the rat spleen cDNA clone, an additional amino terminal domain 1, an additional carboxy terminal domain 7, and 164 bp of what appeared to be a further carboxy terminal domain 8. Immediately 5' to domain 1 was an additional 144 bp sequence presumed to have been derived from an intron between the leader and the first domain. This clone did not contain a 5' leader sequence or 3' transmembrane and cytoplasmic regions. In addition to the previously identified domain 6 in the spleen cDNA clone, the 7th and 8th domains in the RT-PCR clone supported the hypothesis that this clone was a novel rodent ICAM.

EXAMPLE 2

Northern Blot Analysis

In order to further investigate the possibility that the ICAM-related clones identified in Example 1 encoded a novel ICAM polypeptide as suggested by the unique Ig-like domains, tissue specific expression was examined by Northern blot analysis to permit comparison with the previously reported expression patterns of human ICAMs [ICAM-1, Dustin, et al., *J. Immunol.* 137:245–254 (1986); ICAM-2, Staunton, et al., *Nature* 339:61–64 (1989); ICAM-R, de Fourgerolles and Springer, *J. Exp. Med.* 175:185–190 (1992)].

Total cellular RNA from rat lung, brain, spinal cord, liver, digestive tract, thymus, lymph nodes, and spleen was prepared using STAT60 RNA isolation reagents (Tel-test "B", Inc, Friendswood, Tex.) according to the manufacturer's suggested protocol. Poly A+ RNA was purified from total RNA using oligo dT cellulose columns. Approximately 5 µg of RNA derived from each tissue was separated on a 1% formaldehyde agarose gel, and transferred to hybond-C nitrocellulose membranes (Amersham).

A fragment of the rat spleen cDNA from Example 1 corresponding to domains 2 through 4 (nucleotides 1 through 724 in SEQ ID NO: 6) was subcloned into pBluescript SK+ (Stratagene) and an antisense riboprobe was generated by in vitro transcription using $^{32}$P-labeled UTP and approximately 500 ng of linearized template according to a manufacturer's (Boehringer Mannheim, Indianapolis, Ind.) suggested protocol. The membrane-bound RNA was prehybridized in a solution containing 50% formamide, 5× SSC, 1× PE (50 mM Tris-HCl, pH 7.5, 0.1% sodium pyrophosphate, 0.2% polyvinylpyrrolidone, 0.2% ficoll, 5 mM EDTA, 1% SDS) and 150 µg/ml denatured salmon sperm DNA. The radiolabeled probe was denatured by boiling and added to the prehybridization solution to a final concentration of 1×10$^6$ cpm/ml. Hybridization was allowed to proceed for 16–18 hours at 65° C. The membranes were then washed at 65° C. in 2× SSC containing 0.1% SDS and subsequently exposed to X-ray film for 3–16 hours.

The Northern blot analysis indicated that the ICAM-related cDNA identified in Example 1 was expressed only in rat brain, a tissue specificity not previously reported for any other ICAM polypeptides. This expression pattern, in combination with the unique Ig-like domains not known to exist in other ICAM polypeptides, indicated that the ICAM-related clone was a novel member of the ICAM family of proteins, and was named ICAM-4.

The fact that the initially identified cDNA clones were detected in a rat spleen library suggested that a subset of cells in the spleen may express ICAM-4 at low levels. However, a properly spliced clone could not be detected in numerous hemopoietic cDNA libraries which led to doubt if ICAM-4 protein is actually expressed in tissue other than brain. One explanation for the detection of ICAM-4 cDNA in spleen is that the sensitivity of PCR may have amplified a trace amount of transcript even though these tissues do not express the encoded protein.

EXAMPLE 3

Isolation of Full Length Rat ICAM-4 cDNA

A. Identification of a Rat Brain cDNA Clone

In view of the tissue specific expression of ICAM-4, brain tissue mRNA was utilized in an attempt to isolate a full length cDNA encoding ICAM-4. Two probes, one complementary to domains 1 through 2 and a second complementary to domains 3 through 5 of the spleen cDNA clone identified in Example 1 (SEQ ID NO: 7), were radiolabeled and used to screen a rat brain cDNA library in λgt10 which was previously constructed in-house. Hybridization conditions were as described in Example 1, and positive plaques were subjected to one or more rounds of screening to obtain clonal phage.

Nine positive clones were identified, two of which hybridized to both probes. The longest of the two clones, designated clone 7, contained 2550 bp encoding four of the five Ig-like domains found in the probe cDNA. In addition, clone 7 encoded four other Ig-like domains not found in the probe. Putative transmembrane and cytoplasmic domains were identified which were followed by a stop codon, a polyadenylation signal, and a poly A tail. Clone 7 was lacking at least one 5' Ig-like domain as determined by comparison to the RT-PCR clone (SEQ ID NO: 7), and also lacked a leader sequence; re-screening of the library did not yield any longer clones which contained these sequences. The nucleic acid sequence for clone 7 is set forth in SEQ ID NO: 10.

B. Determination of the 5' End

In order to isolate domain 1 and other 5' sequences, a PCR technique termed 5' Rapid Amplification of cDNA Ends (RACE) [*PCR Protocols: A Guide to Methods and Applications,* Innis, et al., (eds) Academic Press: New York (1990) pp: 28–38] was employed using a 5' RACE kit (Clontech). This technique utilizes an internal primer paired with a second primer complementary to an adapter sequence ligated to the 5' end of cDNA library molecules. PCR with this primer pair will therefore amplify and facilitate identification of the intervening sequences. Overlapping sequence information can then be used to generate a complete sequence of the gene.

RACE-ready cDNA from rat brain (supplied with kit) was used in a PCR with the kit oligonucleotide and an antisense primer based on an internal ICAM-4 sequence. The 3' antisense primer, designated Spot714AS, was designed according to an ICAM-4 domain 4 sequence and is set forth in SEQ ID NO: 20.

CARGGTGACAAGGGCTCG (SEQ ID NO: 20)

The amplification product resulting from this primer pair was subsequently subjected to a secondary PCR using the same 5' kit primer paired with a 3' primer complementary to a region in ICAM-4 domain 1. The second 3' primer was designated RRACE2 and is set forth in SEQ ID NO: 21.

TATGAATTCAGTTGAGCCACAGCGAGC (SEQ ID NO: 21)

Each primer used in the secondary PCR contained an EcoR1 site to facilitate cloning of the resulting amplification products into pBS+ (Stratagene). The resulting plasmid DNA which contained the 5' end of the gene was identified by hybridization to a rat ICAM-4 domains 1 and 2 probe, corresponding to nucleotides 1 through 736 in SEQ ID NO: 7. Partial sequence information for domain 1 and the hydrophobic leader was determined from the resulting amplification product.

The product from the 5' RACE method was a DNA fragment 222 bp long containing 60 bp upstream of the initiating methionine residue, an 82 bp leader sequence, and an 80 bp sequence from domain 1. The amplification product is set forth in SEQ ID NO: 11.

C. Full Length Sequence of Rat ICAM-4

A composite clone of the full length ICAM-4 was constructed from the sequence information derived from the 5' RACE method (SEQ ID NO: 11), the RT-PCR clone (SEQ ID NO: 7) and the brain cDNA clone 7 (SEQ ID NO: 10). The full length gene for rat ICAM-4 was determined to contain 2985 bp with a single open reading frame encoding a deduced 917 amino acid protein. A putative Kozak sequence is located upstream of the methionine residue in the leader sequence. A 27 amino acid hydrophobic leader sequence is followed by nine Ig-like domains, a transmembrane region and a 58 amino acid cytoplasmic tail. The composite ICAM-4 cDNA is set for in SEQ ID NO: 1, and the deduced amino acid sequence is set forth in SEQ ID NO: 2.

Like other ICAM polypeptides, ICAM-4 contains extracellular, transmembrane, and cytoplasmic domains. In the extracellular domain, the amino terminus of ICAM-4 is a leader sequence comprising amino acids 1 through 27 which is followed by nine immunoglobulin (Ig)-like domains, a characteristic unique to ICAM-4 in that ICAM-1, ICAM-2, and ICAM-R contain five, two, and five extracellular Ig-like domain, respectively. In ICAM-4, domain 1 comprises amino acids 28 through 118; domain 2 comprises amino acids 119 through 224; domain 3 comprises amino acids 225 through 321; domain 4 comprises amino acids 322 through 405; domain 5 comprises amino acids 406 through 488; domain 6 comprises amino acids 489 through 569; domain 7 comprises amino acids 570 through 662; domain 8 comprises amino acids 663 through 742; and domain 9 comprises amino acids 743 through 830. Within each domain, a characteristic "loop" structure is formed by a disulfide bond between cysteine residues located generally at opposite ends of the domain amino acid sequence. Other structural features of ICAM-4 include the transmembrane region comprising amino acids 831 through 859 and the cytoplasmic region comprising amino acids 860 through 917.

Comparison of amino acid sequence homology of each domain in rat ICAM-4 with the other members of the ICAM family was limited to the corresponding sequences of human ICAM-1, ICAM-2, and ICAM-R since sequence information for all three rodent homologs has not been previously reported. In the first domain, the rodent ICAM-4 shows 21, 30, and 28 percent identity with human ICAM-1, ICAM-2, and ICAM-R, respectively. The second domain is more conserved, with the amino acid percent identities being 60, 42 and 62 with ICAM-1, -2, and -3, respectively. Domains 3–5 show percent identities of 48, 49, and 40 with ICAM-1 and 60, 59 and 29 respectively for ICAM-R. Interestingly, rat ICAM-4 domains 6 through 8 are most homologous with domain 5 (ranging from 29–42% identical), possibly arising from a gene segment duplication event. The ninth and final extracellular domain aligns poorly with other ICAM domains but has 22% identity with the 3rd and 6th domains of human VCAM-1, another member of the Ig family of protein which participate in cell adhesion. The cytoplasmic tail is 58 amino acids long. This is longer than the other members of the ICAM family wherein human ICAM-1, -2, and -3 contain 28, 26, and 37 amino acids, respectively. As with the ninth domain, rat ICAM-4 cytoplasmic tail is most homologous with the cytoplasmic tail of human VCAM-1, which contains only 19 amino acids. The membrane proximal 19 amino acids of rat ICAM-4 share 7 amino acid residues with VCAM-1 (37%).

Finally, functional binding to LFA-1 (CD11a/CD18) maps to the first domain in the ICAMs. Vonderheide et al., [*J. Cell. Biol.*, 125:215–222 (1994)] identified a sequence motif purportedly involved in integrin binding. Despite the relatively low homology between rat ICAM-4 and other ICAMs in domain 1, this binding sequence motif is conserved, suggesting that rat ICAM-4 may be a ligand for LFA-1 and perhaps other integrins.

EXAMPLE 4

In situ Hybridization in Brain Tissue

In order to localize the specific brain tissue which expressed ICAM-4, in situ hybridization with ICAM-4 domain 1 and ICAM-4 domains 3 through 4 anti-sense riboprobes was employed. The probes were labeled by in vitro transcription using $^{35}$S-labeled UTP.

Frozen tissue sections of normal rat brain were fixed in 4% paraformaldehyde for 20 minutes, rinsed and dehydrated, and the fixed RNA denatured for 2 minutes in 2× SSC, 70% formamide at 70° C. prior to hybridization. Tissue sections were hybridized overnight at 50° C. in a solution containing 50% formamide, 0.3M NaCl, 20 mM Tris-HCl, pH 7.4, 5 mM EDTA, 10% dextran sulfate, 1× Denhardt, 0.5 mg/ml yeast RNA, 100 mM DTT and a probe concentration of 50,000 cpm/μl. Slides were washed once in 4× SSC, 10 mM DTT at room temperature for 60 minutes, once in 50% formamide, 2× SSC, 10 mM DTT at 60° C. for 40 minutes, and once in each 2× SSC and 1× SSC for 30 minutes each at room temperature. Specificity of hybridization was determined in parallel experiments performed with the same protocol but also including a more stringent wash in 50% formamide, 1× SSC, 10 mM DTT at 60° C. for 40 minutes. After washing, the slides were dipped in NTB2 emulsion (Kodak, Rochester, N.Y.) and exposed from 2 to 21 days before being developed and counter-stained. Negative controls included sense probes generated from ICAM-4 domain 1 and ICAM-4 domain 3 through 4 sense riboprobes, in addition to a human immunodeficiency virus (HIV-1) riboprobe.

The signal detected in brain tissue was primarily localized in the gray matter with the strongest signal in the cerebral cortex and hippocampus. The hybridization profile was consistent with ICAM-4 expression primarily in cerebral neurons.

EXAMPLE 5

Generation of ICAM-4 Fusion Proteins

Rat ICAM-4/glutathione S-transferase (GST) fusion proteins were generated using the prokaryote expression vector pGEX (Pharmacia, Alameda, Calif.) in order to generate monoclonal antibodies against specific ICAM-4 polypeptide fragments.

PCR primers corresponding to the 5' and 3' ends of domain 1 and the 5' and 3 ends of domain 2 were used to amplify DNA fragments encoding the individual domains. The resulting fragments were separately cloned into an EcoRI site of pGEX-2T; DNA sequence analysis confirmed the correct orientation and reading frame. Transformants were subsequently screened for their ability to produce fusion protein of the appropriate molecular weight.

Both ICAM-4 domain 1/GST and ICAM-4 domain 2/GST fusion proteins remained in the insoluble fraction after the bacteria were lysed by sonication in PBS containing 1% SDS. The insoluble protein fraction from 100 ml cultures were boiled in SDS loading dye and separated on a 10% preparative polyacrylamide-SDS gel. The gel was stained in ice cold 0.4M KCl and the fusion protein bands were excised. Fusion proteins were electroeluted from the gel slices in dialysis tubing in buffer containing 25 mM Tris-HCl and 192 mM glycine. Approximate protein concentration was determined by $OD_{280}$ and purity of the preparation was determined on SDS-PAGE stained with Coomasie blue.

EXAMPLE 6

Production of Monoclonal Antibodies Against Rat ICAM-4/GST Fusion Proteins

Balb/c mice were immunized by subcutaneous injection with 40–50 µg ICAM-4 domain-2/GST fusion protein (described in Example 5) emulsified in Freund's complete adjuvant (FCA). Two weeks later, the mice were again immunized by subcutaneous injection with the same protein, emulsified however in Freund's incomplete adjuvant. Two final intraperitoneal immunizations given two weeks after the second immunization included soluble antigen with no adjuvant given at two week intervals. Serum from each immunized mouse was assayed by ELISA for its ability to specifically react with rat ICAM-4 produced by the baculovirus expression system described infra.

The spleen from mouse #1654 was sterilely removed and placed in 10 ml serum-free RPMI 1640. A single-cell suspension was formed by grinding the spleen tissue between frosted ends of two glass microscope slides submerged in serum free RPMI 1640 (Gibco, Burlington, Ottawa, Canada) supplemented with 2 mM L-glutamine, 1 mM sodium pyruvate, 100 units/ml penicillin, and 100 µg/ml streptomycin. The cell suspension was filtered through a sterile 70-mesh Nitex cell strainer (Becton Dickinson, Parsippany, N.J.), and washed twice with RPMI followed by centrifuging at 200×g for 5 minutes. The resulting pellet from the final wash was resuspended in 20 ml serum-free RPMI. Thymocytes taken from three naive Balb/c mice were prepared in an identical manner.

Prior to fusion, NS-1 myeloma cells were maintained in log phase growth in RPMI with 11% Fetalclone serum (FBS) (Hyclone Laboratories, Logan, Utah) for three days. Once harvested, the cells were centrifuged at 200×g for 5 minutes, and the pellet was washed twice as described in the foregoing paragraph. After washing, the cell suspension was brought to a final volume of 10 ml in serum free RPMI. A 20 µl aliquot was removed and diluted 1:50 with serum free RPMI, and a 20 µl aliquot of this dilution was removed, mixed with 20 µl 0.4% trypan blue stain in 0.85% saline (Gibco), loaded onto a hemacytometer (Baxter Healthcare, Deerfield, Ill.) and the cells counted. Approximately 2.425× $10^8$ spleen cells were combined with 4.85×$10^7$ NS-1 cells, the mixture centrifuged and the supernatant removed. The resulting pellet was dislodged by tapping the tube and 2 ml of 50% PEG 1500 in 75 mM Hepes, pH 8.0, (Boehringer Mannheim, Indianapolis, Ind.) was added with stirring over the course of 1 minute. Subsequently, an additional 14 ml serum free RPMI was added over 7 minutes. The cell suspension was centrifuged at 200×g for 10 minutes and the supernatant discarded. The pellet was resuspended in 200 ml RPMI containing 15% FBS, 100 µM sodium hypoxanthine, 0.4 µM aminopterin, 16 µM thymidine (HAT) (Gibco), 25 units/ml IL-6 (Boehringer Mannheim) and 1.5×$10^6$ thymocytes/ml. The suspension was first placed in a 225 cm² flask (Corning, Essex, United Kingdom) at 37° C. for four hours before being dispensed into ten 96-well flat bottom tissue culture plates (Corning) at 200 µl/well. Cells in the plates were fed on days 3, 4, 5, and 6 post fusion by aspirating approximately 100 µl from each well with a 20 G needle (Becton Dickinson), and adding 100 µl/well plating medium described above except containing 10 units/ml IL-6 and lacking thymocytes.

The fusion plates were screened initially by antigen capture ELISA as follows. Immulon 4 plates (Dynatech, Cambridge, Mass.) were coated overnight at 4° C. with 100 ng/well of either domain 1-GST or domain 2-GST fusion protein in 50 mM carbonate buffer. The plates were blocked with 100 µl/well 0.5% fish skin gelatin (Sigma, St. Louis, Mo.) in PBS for 30 minutes at 37° C. After blocking, the plates were washed 3× with PBS containing 0.05% Tween 20 (PBST) and 50 µl/well of hybridoma supernatant from each fusion was added. After incubation at 37° C. for 30 minutes, the plates were washed as described above, and 50 µl of a 1:3500 dilution of horseradish peroxidase-conjugated goat anti-mouse IgG (Fc) (Jackson ImmunoResearch, West Grove, Pa.) was added. Plates were again incubated for 30 minutes and washed 4× with PBST. Substrate, 100 µl/well, consisting of 1 mg/ml o-phenylene diamine (Sigma) and 0.1 µl/ml 30% $H_2O_2$ in 100 mM citrate, pH 4.5, was added. The color reaction was allowed to proceed 10 minutes and quenched with the addition of 50 µl/well of 15% $H_2SO_4$. Absorbance at 490 nm was then determined on an automated plate reader (Dynatech).

Wells which were positive for domain 2-GST protein, but not for domain 1-GST protein, were then screened by ELISA against a Baculovirus supernatant (described infra). ELISA was performed as described above except that the Immulon 4 plates were initially coated overnight with Baculovirus supernatant diluted 1:4 in 50 mM carbonate buffer. Three wells (103A, 103B and 103F) were cloned two to three times, successively, by doubling dilution in RPMI, 15% FBS, 100 µM sodium hypoxanthine, 16 µM thymidine, and 10 units/ml IL-6. Wells of clone plates were scored visually after 4 days and the number of colonies in the least dense wells was recorded. Selected wells of each cloning were again assayed by ELISA after 7 to 10 days against either domain 1-GST protein and domain 2-GST protein, or Baculovirus supernatant.

The monoclonal antibodies produced by the hybridomas were isotyped by ELISA. Immulon 4 plates (Dynatech) were coated at 4° C. with 50 µl/well goat anti-mouse IgA, IgG, or IgM (Organon Teknika, Durham, N.C.) diluted 1:5000 in 50 mM carbonate buffer, pH 9.6. Wells were blocked for 30 minutes at 37° C. with 1% BSA in PBS, washed 3× with PBST. A 1:10 dilution of hybridoma culture supernatant (50 Al) was added to each plate, incubated, and washed as above. After removal of the last wash, 50 µl horseradish peroxidase-conjugated rabbit anti-mouse $IgG_1$, $G_{2a}$, $G_{2b}$, or $G_3$ (Zymed, San Francisco, Calif.) (diluted 1:1000 in PBST with 1% normal goat serum) was added. Plates were incubated as above, washed 4× with PBST and 100 µl substrate, was added. The color reaction was quenched after 5 minutes with addition of 50 µl 15% $H_2SO_4$, and absorbance at 490 nm determined on a plate reader (Dynatech).

Results indicated that antibodies 103A, 103B, and 103F were all $IgG_1$ isotype. These antibodies were subsequently used in immunocytochemical analyses, Western blotting, and for purification of protein expressed in baculovirus.

EXAMPLE 7

Baculovirus Expression of Rat ICAM-4

A baculovirus expression system (Invitrogen) was used to generate soluble protein corresponding to domains 1 through 6 of ICAM-4. Because the leader sequence for ICAM-4 was not known at the time, the expression construct was made containing the coding sequence for ICAM-4 fused 3' to the ICAM-1 leader sequence in proper reading frame. Specific details regarding construction of the ICAM-1/ICAM-4 expression plasmid is as follows.

Rat ICAM-1 DNA encoding the five Ig-like domains was amplified by PCR using primers which incorporated several features to facilitate construction of the fusion plasmid. The 5' oligonucleotide primer included HindIII and BglII sites, in addition to a consensus Kozak sequence upstream of the first methionine in the leader sequence. The 3' oligonucleotide primer included a coding sequence for six histidines followed by a stop codon and a HindIII cloning site. The PCR amplification product was cloned into a HindIII-digested pBS+ vector and sequence analysis confirmed the appropriate construction. An internal SmaI site in the ICAM-1 leader sequence and another SmaI site in the vector's multiple cloning region (3' to ICAM-1 Ig-like domain 5) were digested which removed most of the ICAM-1 coding sequence. After these manipulations, the linearized, blunt-ended vector contained a portion of the upstream multiple cloning region (those restriction sites 5 of the original HindIII site in the multiple cloning region), the Kozak sequence and most of the ICAM-1 leader sequence.

The coding sequence for rat ICAM-4 domains 1 through 6 was amplified by PCR utilizing primers designed to permit cloning of this sequence into the linearized vector described above. The 5' oligonucleotide primer included an EcoRV site and the codons needed to complete the ICAM-1 leader sequence. The 3' oligonucleotide primer included codons for six histidine residues, a stop codon, and HindIII and EcoRV restriction sites. The amplification product from this PCR was digested with EcoRV to produce a blunt-ended sequence which was then ligated into the blunt-ended SmaI-digested pBS+ linearized vector. The entire sequence containing the ICAM-1 leader sequence 5' to the ICAM-4 domains 1 through 6 was removed from the construct with BglII and HindIII digestion and the purified ICAM-1I/ICAM-4 fusion sequence cloned directly into a BglII/HindIII-digested pBluesac III vector (Invitrogen).

Protein production by the recombinant virus was assayed for by ELISA, initially using immune sera from mice immunized with rat ICAM-4 domain-2/GST fusion protein described in Example 5. In later work, monoclonal antibodies generated from those mice were used to purify ICAM-4 protein produced by the recombinant baculovirus in SF9 cells.

EXAMPLE 8

Production of Monoclonal Antibodies Against Baculovirus-expressed Rat ICAM-4

Rat ICAM-4 domains 1–6 were expressed in the baculovirus expression system as described in Example 7. The recombinant protein was purified using monoclonal antibody 103A (as described in Example 6).

Briefly, 30 mg of purified monoclonal 103A (in 100 mM sodium borate, 500 mM sodium chloride) were coupled to three grams of Activated Cyanogen Bromide Sepharose 4B (Pharmacia, Piscataway, N.J.). Baculovirus supernatant containing recombinant rat ICAM-4 (domains 1–6) was loaded on the Sepharose column overnight at 4° C. The column was washed in calcium-magnesium-free phosphate buffered saline (CMF-PBS) and bound material was eluted in 50 mM citric acid, 500 mM NaCl pH 4.0. The sample was neutralized with 1/10 volume Tris pH 10 and stored at −20° C. The purified protein separated on SDS-PAGE appeared greater than 90% pure and migrated at approximately 80 kD.

Mice were immunized with the purified recombinant rat ICAM-4 domains 1–6 protein in a similar manner as described in Example 6. The spleen from mouse #1945 was used for fusion #127. The fusion protocol was as described in Example 6. The fusion wells were screened by ELISA on the recombinant ICAM-4 protein. The secondary screen included immunocytochemistry on rat brain sections (as below described in Example 9). Four additional antibodies specific for rat ICAM-4 were cloned out of this fusion: 127A, 127E, 127F and 127H. The immunocytochemical staining pattern of each antibody on rat brain sections was the same as observed with monoclonal antibody 103A (see Example 9). The monoclonal antibodies were tested for their ability to bind the D1I/GST and D2/GST fusion proteins (described in Example 5). Monoclonal antibody 127A recognized the D1/GST fusion protein and 127H recognized the D2/GST fusion protein. These two distinct binding specificities along with the others that did not bind either GST protein suggest that at least 3 different epitopes were being recognized by the panel of antibodies. Hybridomas 127A and 127H were deposited May 31, 1995 and Jun. 1, 1995, respectively, with the American Type Culture Collection, 12301 Parklawn Drive, Rockville, Md. 20852, and assigned Accession Numbers HB11905 and HB11911, respectively.

EXAMPLE 9

Immunocytochemistry of Rat ICAM-4 Expression

Immunocytochemistry with monoclonal antibody 103A was performed to localize the protein production within the rat brain.

A brain was harvested from a normal adult female Lewis rat, sagittally sectioned, and washed in RNase-free 1× PBS on ice for 30 min. The brain sections were then placed in Tissue Tek II cryomolds (Miles Laboratories, Inc., Naperville, Ill.) with a small amount of O.C.T. compound (Miles, Inc., Elkhart, Ind.). The brains were centered in the cryomold, the cryomold filled with OCT compound, then placed in a container with 2-methylbutane (Aldrich Chemical Company, Inc., Milwaukee, Wis.) and the container placed in liquid nitrogen. Once the tissue and OCT compound in the cryomold were frozen, the blocks were stored at −80° C. until sectioning.

The tissue was sectioned at 6 μm thickness, adhered to Vectabond (Vector Laboratories, Inc., Burlingame, Calif.) coated slides and allowed to air-dry at room temperature overnight until use. The sections were fixed in ethyl ether (Malinckrodt, Paris, Ky.) for 5 minutes at room temperature. Once the slides were removed from the ether, the reagent was allowed to evaporate. Each tissue section was blocked with 150 μl 50% Normal rat serum (Sigma) and 2% bovine serum albumin (BSA) (Sigma) in 1× PBS (made with sodium phosphates only) for 30 minutes at room temperature. After blocking, the solution was gently blotted from the sections and the purified supernatant antibody 103A (1.65 mg/ml) was diluted 1:10 in the blocking solution and 150 μl applied to each tissue section. The slides were placed in a humidity chamber and incubated at 4° C. overnight.

The next day the antibody solution was blotted gently from the section and the slides washed three times in 1× PBS for four minutes in each wash. The excess PBS was aspirated from the slide and 100 μl of the secondary, rat anti mouse-biotin conjugated antibody (Jackson ImmunoResearch Laboratories), diluted 1:100 in a solution of 10% normal rat serum and 2% BSA in 1× PBS, applied to the tissues. Incubation was allowed to proceed for one hour at room temperature. The sections were washed two times in 1× PBS for four minutes in each wash, then 100 μl of ABC reagent from an Elite Rat IgG Vectastain ABC kit (Vector Laboratories, Inc., Burlingame, Calif.), prepared according to the product insert, was applied to each section. Incubation was allowed to proceed for 30 minutes at room temperature. After incubation, the slides were washed two times in 1× PBS (four minutes each wash) and 150 μl of Vector VIP Peroxidase Substrate Solution (Vector laboratories, Inc., Burlingame, Calif.) applied to each section for approximately ten minutes. After color development, the sections were rinsed under running tap water for five minutes, counterstained with Mayer's hematoxylin (Sigma) for 20 seconds, and rinsed again in gently running tap water for five minutes. The slides were dehydrated across a graded series of ethanols, passed through xylene and mounted with Accumount 60 (Stephens Scientific, Riverdale, N.J.).

Immunohistochemistry of rat brain sections strained with mAb 103A indicated that rat ICAM-4 is expressed in the neuronal cells of the hippocampus. Staining pattern suggested that the protein might be limited to the neuronal processes (dendrites). Brain sections stained in a similar manner with an irrelevant antibody or second step reagent alone do not show the distinct expression pattern seen with MAb 103A.

EXAMPLE 10

Cloning of a Human ICAM-4 Genomic DNA

During the cloning of rat ICAM-4 from genomic DNA, it was discovered that ICAM-4 and ICAM-1 were located within 5 kb of each other and this information was utilized in an attempt to clone the human homologue of ICAM-4.

Genome Systems Inc. (St. Louis, Mo.) amplified fragments in a human P1 library by PCR using human ICAM-1 domain 3 primers, a sense primer designed complementary to human ICAM-1 domain 3 (H-1/D3 S) and an antisense primer designed complementary to human ICAM-1 domain 3 (H-1/D3 AS). These primers are set forth in SEQ ID NOs: 22 and 23, respectively.

CCGGGTCCTAGAGGTGGACACGCA (SEQ ID NO: 22)

TGCAGTGTCTCCTGGCTCTGGTTC (SEQ ID NO: 23)

Two clones, designated 1566 and 1567, were identified and subjected to further analysis. Both P1 clones contained approximately 75–95 kb genomic DNA inserts. The clones were digested with BamH1, separated with agarose gel electrophoresis, and blotted onto nylon membranes. Southern blots hybridization were performed under either low stringency (30% formamide) or high stringency (60% formamide) at 42° C. with human ICAM-1, ICAM-3 or rat ICAM-4 radiolabeled probes; other constituents of the hybridization solution were as described in Example 1. The low stringency hybridization series was washed at room temperature in 2× SSPE containing 0.1% SDS. The high stringency hybridization was washed at 65° C. in 0.2× SSPE containing 0.1% SDS. The washed membranes were exposed to X-ray film for 3.5 hours.

The differential hybridization indicated that human ICAM-1 was contained on a 5.5 kb BamH1 fragment while human ICAM-3 was located on a 4.0 kb and a 1.5 kb BamH1 fragment. The human ICAM-1 and ICAM-R fragments were subcloned into pBS+ and their identity confirmed by limited sequence analysis.

A 7.0 kb BamH1 fragment that hybridized with rat ICAM-4 under high stringency conditions was subcloned and further fragmented with RsaI restriction digestion. Three RsaI fragments that hybridized with rat ICAM-4 were identified and their sequences determined. Based on homology to rat ICAM-4, these fragments appeared to contain domains 2, 3, 4, 5 and part of domain 6.

EXAMPLE 11

Cloning of a Human ICAM-4 cDNA

The fragments of genomic DNA corresponding to domains 2–5 of human ICAM-4 (described in Example 10) were used as probes to screen a λgt10 Human hippocampus cDNA library (Clontech, Palo Alto, Calif.). The library screening protocol was essentially as described in Example 1.

The longest human ICAM-4 clone (#18) that was found in that library was only 992 bp (SEQ ID: 24) and corresponded to roughly the middle of the predicted 3 kb gene. The 992 bp DNA insert from clone 18 (SEQ ID: 24) was used as a probe to screen a λZAPII human hippocampus cDNA library (Stratagene, La Jolla, Calif.). This library yielded a number of positive clones. The longest clone, #34, was 2775 bp (SEQ ID: 25). Based on alignments to the full length rat ICAM-4, it was predicted that this clone was missing the leader sequence and approximately 30 bp at the 5' end of domain 1. The poly $A^+$ tail at the 3' end was missing, but the translation stop codon was present.

A fragment of DNA corresponding to the first 3 domains (nucleotides 1 to 840 in clone #34) was used as a probe to screen a λgt10 cDNA library derived from human cerebral cortex (Clontech, Palo Alto, Calif.). One clone, 16-1 (SEQ ID: 26), was identified as having 1557 bp, and included 39 bp of 5 untranslated DNA, a leader sequence and sequence information through the fifth domain. Overlapping clones #34 (SEQ ID: 25) and 16-1 (SEQ ID: 26) were used to generate a composite of the full length human ICAM-4 sequence (SEQ ID: 27).

The full length gene is 2927 bp long and encodes a 924 amino acid protein. The ICAM-4 nucleotide sequence is set out in SEQ ID NO: 27 and the amino acid sequence is set out in SEQ ID NO: 28. Sequence alignment with the full length rat ICAM-4 gene (SEQ ID: 11) revealed an overall DNA sequence identity of 82% and 85% identity at the amino acid level. The apparent 9 Ig like extracellular domain structure of the protein is conserved between rat and human. The leader sequence extends from amino acid 1 to 28; domain 1 from amino acid 29 to 117; domain 2 from amino acid 118 to 224; domain 3 from amino acid 225 to 320; domain 4 from amino acid 321 to 405; domain 5 from amino acid 406 to 488; domain 6 from amino acid 489 to 570; domain 7 from amino acid 571 to 663; domain 8 from amino acid 664 to 743; domain 9 from amino acid 744 to 837; the transmembrane region from amino acid 838 to 857 and the cytoplasmic tail from amino acid 858 to 924.

Human ICAM-4 (HuICAM-4), in addition to being genetically linked to ICAM-1 and ICAM-R, also showed certain common structural features that group them together as a family of molecules. A domain by domain alignment of HuICAM-4 with the other members of the ICAM family shows varying degrees of homology. Domain 1 amino acid sequence of HuICAM-4 is 21, 30 and 26% identical to domain 1 of ICAMs 1, 2 and 3 respectively. Domain 2 of HuICAM-4 is 61, 39 and 62% identical to ICAMs 1, 2 and 3 respectively. Domain 3 of HuICAM-4 is 50 and 65% identical to ICAMs 1 and 3 respectively. Domain 4 of HuICAM-4 is 54 and 64% identical to ICAMs 1 and 3 respectively. Domains 5–8 of HuICAM-4 are most homologous to the fifth domains of ICAM-1 and 3, with percent identities ranging from 33–47 for ICAM-1 domain 5 and 21–31 for ICAM-R domain 5. The ninth domain of HuICAM-4 aligns poorly with the other members of the ICAM family but is homologous to domains 3 (24% identical) and 6 (23% identical) of HuICAM-1.

EXAMPLE 12

Northern Analysis of Human ICAM-4 Expression

Two human multiple tissue Northern (MTN) blots were purchased from Clontech (Palo Alto, Calif.). These contained at least 2 μg of poly A$^+$ RNA from 16 different human tissues (as shown in Table 1) run on a denaturing formaldehyde 1.2% agarose gel and transferred to nylon membrane. The blots were prehybridized for three hours at 42° C. in 10 ml of a solution containing 5× SSPE, 10× Denhardts solution, 50% formamide, 2% SDS and 100 μg/ml denatured salmon sperm DNA. The blots were hybridized in the above solution with a radiolabeled human ICAM-4 probe (clone #18, SEQ ID: 24) for 16 hours at 42° C. The following day, the blots were washed in a solution of 0.1× SSC/0.1% SDS at room temperature followed by a wash at 50° C. The blots were exposed to x-ray film at −80° C for 24 hours. Results of the analysis are shown below in Table 1.

Only the lane containing RNA from the brain hybridized to the ICAM-4 probe, giving a single band at approximately 3 kb. Longer exposure (five days) confirmed that only the brain had a detectable level of message. In order to determine if all lanes contained comparable amounts of RNA of comparable quality, the same blot was hybridized with a control β-actin probe. Blots were stripped of the ICAM-4 probe by treatment with a boiling solution of 0.1% SDS for 15 minutes, and subsequently probed in a similar manner with a β actin probe provided by the manufacturer. Except for minor variation in amounts, all lanes were shown to have good quality RNA.

TABLE 1

Northern Tissue Analysis of Human ICAM-4 Expression

| | PROBE | |
|---|---|---|
| Tissue | ICAM-4 | β-Actin |
| Heart | − | +++ |
| Brain | + | ++ |
| Placenta | − | +++ |
| Lung | − | +++ |
| Liver | − | +++ |
| Skeletal muscle | − | ++++ |
| Kidney | − | +++ |
| Pancreas | − | ++ |
| Spleen | − | +++ |
| Thymus | − | +++ |
| Prostate | − | +++ |
| Testis | − | +++ |
| Ovary | − | +++ |
| Small intestine | − | +++ |
| Colon | − | +++ |
| Peripheral blood leukocyte | − | +++ |

Two additional Northern blots were purchased from Clontech that contained poly A$^+$ RNA from 16 different sub-regions of human brain (as shown in Table 2). Blots were probed in a manner similar to that used for tissue analysis and results are shown in Table 2. RNA quality and quantity loaded was checked by probing the blots with a β actin probe.

All of the regions that showed ICAM-4 expression are part of the telencephalon, with the exception of the thalamus which is considered part of the diencephalon. The hippocampus and cerebral cortex appeared to have the highest level of expression. The transcript size in all cases was the same, 3 kb. The exquisite tissue distribution of the ICAM-4 expression suggests that the promoter region may contain elements that confer the observed developmental and spatial expression of the gene product. The utility of such information may provide insight into the understanding of control of neural gene expression in general.

TABLE 2

Northern Brain Cell Type Analysis of Human ICAM-4 Expression

| | PROBE | |
|---|---|---|
| Brain Region | ICAM-4 | β-Actin |
| Amygdala | ++ | +++ |
| Caudate nucleus | ++ | +++ |
| Corpus callosum | + | +++ |
| Hippocampus | ++ | +++ |
| Hypothalamus | − | +++ |
| Substantia nigra | − | +++ |
| Subthalamic nucleus | + | +++ |
| Thalamus | + | +++ |
| Cerebellum | − | +++ |
| Cerebral cortex | +++ | +++ |
| Medulla | − | +++ |
| Spinal cord | − | +++ |
| Occipital pole | ++ | +++ |
| Frontal lobe | ++ | +++ |
| Temporal lobe | ++ | +++ |
| Putamen | ++ | +++ |

EXAMPLE 13

Generation of Human ICAM-4/IgG Fusion Proteins

Human ICAM-4/IgG1 fusion proteins expression plasmids were constructed to produce proteins for generating monoclonal antibodies and for use in adhesion assays to identify potential ICAM-4 ligands. Two constructs were made; the first included DNA encoding domains 1–3 of HuICAM-4 and the second, domains 4–8. Both were linked to the Fc region of human IgG1 in vector pDCS1 that uses the cytomegalovirus (CMV) promoter to drive expression and the signal sequence from IgG4 to facilitate secretion of the molecules.

PCR primers (shown below as SEQ ID NOs: 29–32) were designed to generate the necessary DNA fragments for sub-cloning. The "sense" primer for the 5' end of domain 1 (HI4-D1(s), SEQ ID NO: 29) was designed to fill in 30 base pairs of domain 1 missing in clone #34. Primers HI4-D1(S) (SEQ ID NO: 29) and HI4-D3(AS) (SEQ ID NO: 30) were used to generate a DNA fragment encoding domains 1–3 of human ICAM-4, corresponding to a region in SEQ ID NO: 1 from nucleotide 130 to nucleotide 996. Primers HI4-D3(S) (SEQ ID NO: 31) and HI4-D8(AS) (SEQ ID NO: 32) were used to generate a DNA fragment encoding domains 4–8 of human ICAM-4, corresponding to a region in SEQ ID NO: 30 from nucleotide 997 to nucleotide 2268. Each 5' primer encoded a BamHI restriction site (GGATCC, indicated in bold below) and each 3' (antisense) primer contained a XhoI site (CTCGAG, indicated in bold below) to facilitate subcloning 5' to the IgG1 gene. All oligonucleotides contain spacer nucleotides (underlined, below) at the 5' end to permit restriction digestion.

HI4-D1(S) (SEQ ID NO: 29)
GTACTTAC<u>AGGATCC</u>GCGGTCTCGCAG-
GAGCCCTTCTGGGCGGACCTACAGCCTGCGTGGCGTTC
HI4-D3(AS) (SEQ ID NO: 30)
ATTTCT<u>CTCGAG</u>GATGGTCACGTTCTCCCGG
HI4-D4(S) (SEQ ID NO: 31)
ATTTCT<u>GGATCC</u>TACAGCTTCCCGGCACCACTC
HI4-D8(AS) (SEQ ID NO: 32)
ATTTCT<u>CTCGAG</u>TTCCACGCCCACAGTGACGG

PCR reactions were carried out in a 50 μl volume using buffers supplied by Perkin Elmer with the AmpliTaq enzyme. Primers were added at a final concentration of 10 μg/ml and all four dNTPs were included at 2 mM. The reactions were continued through 30 cycles of denaturation (94° C. for four minutes), annealing (50° C. for two minutes) and extension (72° C. for one minute). PCR products were visualized on agarose gels and an aliquot of each reaction was used to subclone the PCR products into vector pCRII (Invitrogen, San Diego, Calif.). Sequence analysis was performed to detect possible errors resulting from the amplification process and to confirm proper orientation. Appropriate clones were digested with BamHI and XhoI and fragments separated with agarose gel electrophoresis. Purified fragments were ligated into a pDCS 1 vector previously digested with BamHI and XhoI and the resulting plasmids were sequenced to confirm proper orientation and reading frame.

Human ICAM-4 domains 1–3 and 4–8/IgG1 fusion proteins were obtained following transient transfection of the expression plasmids into COS7 cells and isolation of the secreted protein from the culture media. Transfection was carried out as follows. Adherent COS7 cells at approximately 50–60% confluence were washed with CMF-PBS and subsequently contacted with 10–15 μg of plasmid DNA in 7.5 ml serum-free DMEM media (Gibco, Gaithersburg, Md.) containing 6 μl of 0.25M chloroquine (Sigma, St. Louis, Mo.). An additional 7.5 ml of serum-free media containing 150 μl of DEAE dextran (50 mg/ml) (Sigma, St. Louis, Mo.) were added and the plates incubated 2–3 hours before the media was removed and replaced with 10% DMSO (Mallinckrodt, McGaw Park, Ill.) in PBS. After a one minute incubation, the DMSO solution was removed and replaced with fresh media containing 5% FBS. Each transfection included multiple plates, and media from cells expressing the same protein were pooled for protein isolation.

Media were collected every three days over the course of 3–4 harvests. Proteins were purified using a 0.4–0.8 ml Procep A column (Bioprocessing Ltd, England) pre-equilibrated with 35 mM Tris, 150 mM NaCl, pH 7.5. Culture media was loaded onto the column two times at a flow rate of less than 60 column volumes per hour. The column was washed one time with each of 20 column volumes of Tris/NaCl buffer, 20 column volumes of 0.55M diethanolamine, pH 8.5, and 20 column volumes of 50 mM citric acid, pH 5.0. The fusion proteins were eluted into one ml fractions using 50 mM citric acid pH 3.0 and each fraction was neutralized with 1/10 volume 1M Tris, pH 9.5. Protein concentration was determined by $OD_{280}$, and purity was determined using SDS-PAGE.

A significant contamination from bovine IgG (present in the FBS) was noted. Even though the domains 1–3 fusion protein was predicted to be smaller than the domains 4–8 fusion protein, both migrated at approximately 90 kD. One possible explanation for the observation is that the smaller domains 1–3 fusion protein may be more heavily glycosylated than the larger domains 4–8 fusion protein.

In addition to use of the purified proteins for monoclonal antibody production, described below, the proteins will also be used in adhesion assays to identify ICAM-4 ligands.

EXAMPLE 14

Monoclonal Antibody Production

The purified protein described in Example 13 was utilized to generate monoclonal antibodies using an immunization protocol as described in Example 6.

The spleen from mouse #2250 (immunized with HuICAM-4 D1-3/IgG1) was used for fusion 172 and the spleen from mouse #2272 (immunized with HuICAM-4 D4-8/IgG1) was used for fusion 173. The fusion protocol utilized was as described in Example 6. Fusion plates were screened by ELISA (essentially as described in Example 6) using each HuICAM-4/IgG1 fusion protein. Fusion well supernatants that recognized the immunogen protein, and no other, were considered for cloning. Immunocytochemistry on human hippocampus sections was used as a secondary screen.

One primary clone from each fusion was positive by immunocytochemistry and was cloned. One of the two clones failed to grow upon cloning, leaving only one candidate to pursue, clone 173E which was derived from the HuICAM-4 D4-8/IgG1 immunized mouse. Hybridoma 173E was deposited Jun. 1, 1995 with the American Type Culture Collection, 12301 Parklawn Drive, Rockville, Md. 20852, and assigned Accession Number HB11912.

Additional fusions are similarly performed to generate other antibodies specifically immunoreactive with particular ICAM-4 fragments.

What is claimed is:

1. A hybridoma designated 127A (A.T.C.C. Accession Number HB11905).

2. A monoclonal antibody secreted by the hybridoma of claim 1.

3. A hybridoma designated 127H (A.T.C.C. Accession. Number HB11911).

4. A monoclonal antibody secreted by the hybridoma of claim 3.

5. A hybridoma designated 173E (A.T.C.C. Accession Number HB 11912).

6. A monoclonal antibody secreted by the hybridoma of claim 5.

* * * * *

UNITED STATES PATENT AND TRADEMARK OFFICE
CERTIFICATE OF CORRECTION

PATENT NO. : 5,773,293
DATED : June 30, 1998
INVENTOR(S) : Kilgannon et al

Page 1 of 2

It is certified that error appears in the above-identified patent and that said Letters Patent is hereby corrected as shown below:

On the title page: Item [56]

col. 2: Newmann, et al.: Please delete "Newmann", and insert - -Newman- -.

col. 2, Yoshihiro, et al.: Please delete "brian", and insert - -brain- -.

Col. 13, line 15: Please delete "for", and insert - -forth- -.

Col. 16, line 22: Please delete "µ/ml", and insert - -µl/ml- -.

Col. 16, line 49: Please delete "Al)", and insert - -µl)- -.

Col. 17, line 23: Please delete "sites 5", and insert - -sites 5'- -.

Col. 17, line 39: Please delete "ICAM-1I/ICAM-4", and insert - -ICAM-1/ICAM-4- -

Col. 18, line 11: Please delete "below described", and insert - -described below- -.

Col. 18, line 17: Please delete "D1I/GST", and insert - -D1/GST- -.

UNITED STATES PATENT AND TRADEMARK OFFICE
CERTIFICATE OF CORRECTION

PATENT NO. : 5,773,293
DATED : June 30, 1998
INVENTOR(S) : Kilgannon et al.

It is certified that error appears in the above-identified patent and that said Letters Patent is hereby corrected as shown below:

Col. 20, line 38: Please delete "bp of 5", and insert - -bp of 5'- -.

Col. 21, line 66: Please delete "Poly A⁻ RNA", and insert - -Poly A⁺ RNA- -.

Col. 31, SEQ ID NO:2: After "...(B) Type: amino acid", please insert "(C) Strandedness: single- -.

Col. 75, SEQ ID NO:28: After "...(B) Type: amino acid", please insert "(C) Strandedness: single- -.

Signed and Sealed this

Twenty-eighth Day of November, 2000

Attest:

Q. TODD DICKINSON

*Attesting Officer*

*Director of Patents and Trademarks*